US007951906B2

(12) United States Patent  
Bock et al.

(10) Patent No.: US 7,951,906 B2  
(45) Date of Patent: May 31, 2011

(54) COMPOUNDS CAPABLE OF INTERACTING WITH A CELL-SURFACE FIBROBLAST GROWTH FACTOR RECEPTOR

(75) Inventors: Elisabeth Bock, Charlottenlund (DK); Vladimir Berezin, Copenhagen N (DK); Morten Albrechtsen, Charlottenlund (DK)

(73) Assignee: Enkam Pharmaceuticals A/S, Copenhagen O (DK)

( * ) Notice: Subject to any disclaimer, the term of this patent is extended or adjusted under 35 U.S.C. 154(b) by 0 days.

(21) Appl. No.: 12/370,003

(22) Filed: Feb. 12, 2009

(65) Prior Publication Data

US 2009/0202554 A1 Aug. 13, 2009

Related U.S. Application Data

(63) Continuation of application No. 10/539,440, filed as application No. PCT/DK03/000901 on Dec. 18, 2003, now abandoned.

(30) Foreign Application Priority Data

Dec. 20, 2002 (DK) .................................. 2002 01982  
Mar. 3, 2003 (DK) .................................. 2003 00330

(51) Int. Cl.  
*C07K 4/00* (2006.01)  
*G01N 33/53* (2006.01)

(52) U.S. Cl. ........................................ 530/300; 435/7.1

(58) Field of Classification Search .................. None  
See application file for complete search history.

(56) References Cited

U.S. PATENT DOCUMENTS 5,596,071 A * 1/1997 Payne et al. ................... 530/350  
5,989,554 A * 11/1999 Knuth et al. ................ 424/192.1  
6,255,454 B1    7/2001 Keifer et al.

FOREIGN PATENT DOCUMENTS

| WO | 9100916     | 1/1991  |
| WO | 9738708     | 10/1997 |
| WO | 98/49302 A1 | 11/1998 |
| WO | 99/10364 A1 | 3/1999  |
| WO | 99/63088 A2 | 12/1999 |
| WO | 0011204     | 3/2000  |
| WO | 00/24756 A1 | 5/2000  |
| WO | 01/49715 A2 | 7/2001  |
| WO | 0196364     | 12/2001 |
| WO | 03016351    | 2/2003  |

OTHER PUBLICATIONS

Wells, 1990, Biochemistry 29:8509-8517.*  
Kiselyov et al., Structural basis for a direct interaction between FGFR1 and NCAM and evidence for a regulatory role of ATP Structure. 11(6):691-701, Jun. 2003.

"Fibroblast Growth Factor 2; FGFS", http://www.ncbi.nlm.nih.gov/entrez/dispomim.cgi?cmd=entry&id=134920, (2007).  
Berezin, V., Bock, E., and Poulsen, F.M. (2000). The neural cell adhesion molecule. Curr. Opin. Drug. Disc. Dev. 3, 605-9.  
Bodenhausen, G., and Ruben, D.J. (1980). Natural abundance nitrogen-15 NMR by enhanced heteronuclear spectroscopy. Chem. Phys. Lett. 69, 185-9.  
Braunsweiler, L., and Ernst, R.R. (1983). Coherence transfer by isotropic mixing: application to proton correlation spectroscopy. J. Magn. Reson. 53, 521-8.  
Chan, A.W., Hutchinson, E.G., Harris, D., Thornton, J.M. (1993). Identification, classification, and analysis of beta-bulges in proteins. Protein Sci. 2, 1574-90.  
Dzhandzhugazyan, K., Bock, E. (1993). Demonstration of (Ca(2+)-Mg2+)-ATPase activity of the neural cell adhesion molecule. FEBS Lett. 336, 279-83.  
Dzhandzhugazyan, K., Bock, E. (1997). Demonstration of an extracellular ATP-binding site in NCAM: functional implications of nucleotide binding. Biochemistry 36, 15381-95.  
Eriksson, A.E., Cousens, L.S., Matthews, B.W. (1993). Refinement of the structure of human basic fibroblast growth factor at 1.6 A resolution and analysis of presumed heparin binding sites by selenate substitution. Protein Sci. 2, 1274-84.  
Hatten, M.E., Lynch, M., Rydel, R.E., Sanchez, J., Joseph-Silverstein, J., Moscatelli, D., Rifkin, D.B. (1988). In vitro neurite extension by granule neurons is dependent upon astroglial-derived fibroblast growth factor. Dev. Biol. 125, 280-9. Kiselyov, V.V., Berezin, V., Maar, T.E., Soroka, V., Edvardsen, K., Schousboe, A., Book, E. (1997). The first immunoglobulin-like neural cell adhesion molecule (NCAM) domain is Involved in double-reciprocal interaction with the second immunoglobulin-like NCAM domain and in heparin binding. J. Biol. Chem. 272, 10125-34.  
Kjær, M., Andersen, M.K., and Poulsen, F.M. (1994). Automated and semiautomated analysis of homo- and heteronuclear multidimensional nuclear magnetic resonance spectra of proteins: the program Pronto. Methods Enzymol. 239, 288-307.

(Continued)

*Primary Examiner* — Robert Landsman  
*Assistant Examiner* — Gyan Chandra  
(74) *Attorney, Agent, or Firm* — Iver P. Cooper

(57) ABSTRACT

The present invention relates to a method for modulating the interaction between at least two proteins, wherein at least one of the two proteins is a functional cell-surface receptor and the other protein is the receptor ligand. The invention features a binding site of said functional cell-surface receptor on the receptor ligand and discloses a series of amino acid sequences, which are part of the structure of said binding site and/or involved in the interaction between the receptor and the ligand. Moreover, the present invention features methods for molecular design and screening of a candidate compound capable of modulating the interaction between the functional cell-surface receptor and receptor ligand through the described binding site, and provides a screening assay for identification of such a compound. The invention further describes an antibody capable of binding to the above binding site and/or to an epitope comprising an amino acid sequence essential for executing the receptor ligand interaction through said binding site. The invention also concerns a variety of uses of the disclosed methods, peptide sequences and antibodies. The invention in preferred embodiments concerns the binding site of the fibroblast growth factor receptor (FGFR) on FGFR ligands, compounds capable of modulating the receptor ligand interaction through said binding site, and antibody capable of recognition of said binding site.

20 Claims, 11 Drawing Sheets

OTHER PUBLICATIONS

Kumar, A., Wagner, G., Ernst, R.R., and Wüthrich, K. (1981). Buildup rates of the nuclear Overhauser effect measured by two-dimensional proton magnetic resonance spectroscopy: implications for studies of protein conformation. J. Am. Chem. Soc. 103, 3654-8.

Piantini, U., Sørensen, O.W., and Ernst, R.R. (1982). Multiple quantum filters for elucidating NMR coupling networks. J. Am. Chem. Soc. 104, 6800-1.

Powers, C.J., McLeskey, S.W., Wellstein, A. (2000). Fibroblast growth factors, their receptors and signaling. Endocr. Relat. Cancer 7, 165-97.

Skladchlkova, G., Ronn, L.C., Berezin, V., Bock, E. (1999). Extracellular adenosine triphosphate affects neural cell adhesion molecule (NCAM)-mediated cell adhesion and neurlte outgrowth. J. Neurosci. Res, 57, 207-18.

Thomsen, N.K., Soroka, V., Jensen, P.H., Berezin, V., Kiselyov, V.V., Bock, E., Poulsen, F.M. (1996). The three-dimensional structure of the first domain of neural cell adhesion molecule. Nat. Struct. Biol. 3, 581-5.

Williams, E.J., Furness, J., Walsh, F.S., Doherty, P. (1994). Activation of the FGF receptor underlies neurite outgrowth stimulated by L1, N-CAM, and N-cadherin. Neuron 13, 583-94.

Zhang, O., Kay, L.E., Oliver, J.P., and Forman-Kay, J.D. (1994). Backbone 1H and 15N resonance assignments of the N-terminal SH3 domain of drk in folded and unfolded states using enhanced-sensitivity pulsed field gradient NMR techniques. J. Biomol. NMR. 4, 845-58.

Rønn L.C.B., Doherty P., Holm A., Berezin V., Bock E. "Neurite Outgrowth induced by a Synthetic Peptide Ligand of Neural Cell Adhesion Molecule Requires Fibroblast Growth Factor Receptor Activation" Journal of Neurochemistry 75:665-671 (2000).

Niethammer P., Dolling M., Sytnyk V., Dityatev A., Fukami K., Schachner M. "Cosignaling of NCAM via lipid rafts and the FGF receptor is required for nouritogenesis" The Journal of Cell Biology, 157, No. 3, Apr. 29, 2002. 521-532.

Kos F.J., Chin C.S. "Costimulation of T cell receptor-triggered IL-2 production by Jurkat T cells via fibroblast growth factor receptor 1 upon Its engagement by C056" Immunology and Cell Biology (2002) 80:364-369.

Stauber, D.J., et al. "Structural interactions of fibroblast growth factor receptor with its ligands" PNAS, Jan. 4, 2000, vol. 97, No. 1, pp. 49-54.

Ito, C., et al. "Decapeptide with fibroblast growth factor (FGF)-5 partial sequence inhibits hair growth suppressing activity of FGF-5" Journal of cellular physiology 197:272-283, 2003.

Springer, B.A., et al. "Identification and concerted function of two receptor binding surfaces on basic fibroblast growth factor required for mitogenesis" Thr journal of Biological chemistry, vol. 269, No. 43, Issue of Oct. 28, pp. 26679-26884, 1994.

* cited by examiner

COMPOUNDS CAPABLE OF INTERACTING WITH A CELL-SURFACE FIBROBLAST GROWTH FACTOR RECEPTOR

FIELD OF INVENTION

The present invention relates to a method for modulating the interaction between at least two proteins, wherein at least one of the two proteins is a functional cell-surface receptor and the other protein is the receptor ligand. The invention preferably concerns interaction of the fibroblast growth factor receptor (FGFR) and FGFR ligands. The invention further relates to a series of amino acid sequences involved in forming a binding site for FGFR in a FGFR ligand. Moreover, the present invention features the methods for molecular design and screening of a candidate compound capable of modulating the interaction between FGFR and a protein having the above binding site, and provides a screening assay for identification of such a compound.

BACKGROUND OF INVENTION

Neural cell adhesion molecules (CAMs) of the immunoglobulin superfamily nucleate and maintain groups of cells at key sites during early development and in the adult. In addition to their adhesive properties, CAMs homophylic and heterophylic interactions can affect intracellular signaling. Their ability to influence developmental events, including cell migration, proliferation, and differentiation may therefore result both from their adhesive as well as their signaling properties.

The neural cell adhesion molecule, NCAM, was the first discovered neural CAM. Since the discovery NCAM has been intensively studied and now it is well characterised.

NCAM belongs to the immunoglobulin (Ig) superfamily. Its extracellular part consists of five Ig-like and two fibronectin type III (F3) modules (Berezin et al., 2000). NCAM assists both the cell-cell and cell-substratum interactions. NCAM binds to various extracellular matrix components such as heparin/heparan sulfate, chondroitin sulfate proteoglycans, and different types of collagen. Cell-cell interactions are mostly assisted by the NCAM homophilic interaction.

The different modules of NCAM have been shown to perform distinct functions. Thus, NCAM homophilic binding is believed now to depend on the first three Ig modules. The heparin binding sequence is localized to the Ig2 module. NCAM also binds to the neural cell adhesion molecule L1. This interaction is believed to take place between the fourth Ig module of NCAM and an oligomannosidic moiety expressed on L1. The two membrane-proximal F3 modules of NCAM has been suggested to be involved in FGFR binding. Among a number of ligands of NCAM the most intriguing remain to be ATP. NCAM has been demonstrated to hydrolyze extracellularly adenosine triphosphate (ATP) (Dzhandzhugazyan and Bock, 1993 and 1997), and the proximal F3 modules have been suggested to be involved in this activity of NCAM. Recently, ATP has been demonstrated to be a modulator of NCAM induced neuritogenesis (Skladchikova et al., 1999). However, the role extracellular ATP, which is one of the most abundant neurotransmitters in the brain, in relation to known biological functions of NCAM is not well understood.

A number of research groups has now accumulated a large body of evidence indicating that intracellular signaling cascades underlying the NCAM-mediated axonal outgrowth are similar to signal transduction cascades which are activated due to stimulation of the fibtoblast growth factor receptor (FGFR).

Fibroblast growth factor receptors (FGFRs) are a family of four closely related receptor protein tyrosine kinases consisting extracellularly of three Ig-like modules and intracellularly of a split tyrosine-kinase module (Powers et al., 2000). The receptors are known as key regulators of morphogenesis, development, angiogenesis, and wound healing. FGFR activation and signaling are dependent on dimerization of the receptor which is induced by a high affinity binding of its ligand, fibroblast growth factor (FGF), and it also requires participation of cell surface heparin or heparan sulphate proteoglycans.

The major neural CAMs, NCAM, L1 and N-cadherin, all have been regarded as a new class of putative alternative ligands of FGFR, although there have not been so far obtained any evidence for a direct interaction between these CAMs and the receptor so far. The identification of a common structural motif which might be a prerequisite for the interaction with FGFR seems to be very advantageous in view of the development of new drugs for the treatment of a variety of pathologic disorders where the regulation of activity of FGFR may play the key role.

SUMMARY OF INVENTION

The present invention is directed to a method of modulating the interaction between at least two different proteins, wherein one of the at least two different proteins is represented by a functional cell-surface receptor, or a fragment, or a variant thereof, and the other of the at least two different proteins is represented by a polypeptide having a binding site to said receptor, wherein at least a part of said binding site comprises at least one of the sequences set forth in SEQ ID NOS: 1-146 or fragments, or variants, or homologues of said sequences, or fragments or variants of said homologues, comprising i) providing a compound capable of interacting with the receptor and/or the polypeptide thereby interfering with said receptor and said polypeptide interaction,
ii) presenting the compound of step (i) to the at least two different proteins.

The invention is also directed to a method of modulating the interaction between at least two different proteins, wherein one of the at least two different proteins is represented by a functional cell-surface receptor, or a fragment, or a variant thereof, and another of the at least two different proteins is represented by a polypeptide having a binding site to said receptor, wherein said binding site is essentially consisting of one or more "strand-loop-strand" structural motifs, comprising i) providing a compound capable of interacting with the receptor and/or polypeptide thereby interfering with said receptor and said polypeptide interaction,
ii) presenting the compound of step (i) to the at least two different proteins.

An another aspect of the invention concerns a screening method for a candidate compound capable of modulating the interaction between at least two different proteins, wherein one of the at least two different proteins is represented by a functional cell-surface receptor, or a fragment, or a variant thereof, and the other of the at least two different proteins is represented by a polypeptide having a binding site to said receptor, wherein at least a part of said binding site comprises at least one of the sequences set forth in SEQ ID NOS: 1-146 or fragments, or variants, or homologues of said sequences, or fragments or variants of said homologues, comprising i) providing the at least two different proteins;
ii) providing a compound;

iii) presenting the compound of (ii) to the at least two different proteins of (i);
iv) determining the interaction between the at least two different proteins before and after the presenting the compound to said proteins;
v) determining whether the interaction between the at least two different proteins has been modulated by the presented compound,
vi) selecting a candidate compound capable of modulating the interaction between the at least two different proteins.

Furthermore, the invention discloses an assay for sequential screening of a candidate compound capable of modulating the interaction between at least two different proteins, wherein one of the least two different proteins is represented by a functional cell-surface receptor, or a fragment or a variant thereof, and the other of the at least two different proteins is represented by a polypeptide having a binding site to said receptor, wherein at least a part of said binding site comprises at least one of the sequences set forth in SEQ ID NOS: 1-146 or fragments, or variants, or homologues of said sequences, or fragments or variants of said homologues, comprising the steps of
i) providing the at least one functional cell-surface receptor molecule, or a fragment, or a variant thereof, and the at least one polypeptide having a binding site to said receptor, wherein at least a part of said binding site comprises at least one of the sequences set forth in SEQ ID NOS: 1-146 or fragments, or variants, or homologues of said sequences, or a fragments or a variants of said homologues,
ii) presenting the at least one receptor molecule of step (i) to the at least one polypeptide of step (i), or presenting the at least one polypeptide of step (i) to the at least one receptor molecule of step (i) and permitting the interaction between the said receptor and said polypeptide, followed by the
iii) recording the interaction between the molecules of step (ii),
iv) presenting the candidate compound to the molecules of step (ii);
v) recording the interaction between the molecules of step (iv), followed by the
vi) assessment of at least one effect of the candidate compound on the interaction between the molecules of step (iv), followed by the
vii) selection of a compound capable of modulating the interaction between the at least one functional cell-surface receptor molecule and the at least one polypeptide of step (i).

The method(s) and the assay of the invention are all preferably designated to the modulation of interaction between FGFR and a protein comprising the FGFR binding site, said site comprising at least one of the sequences set forth in SEQ ID NOS: 1-146 or fragments, or variants, or homologues of said sequences, by a compound capable of this modulation. Therefore, it is an important aspect of the invention to provide a method for molecular design of such a compound, said method comprising the structural data on the binding FGFR with a protein comprising the above binding site, said data comprising a molecular model of interaction between FGFR and NCAM.

Furthermore, it is another important aspect of the invention to provide a method A method for isolating a candidate compound capable of modulating the interaction between at least two different proteins, wherein one of the least two different proteins is represented by a functional cell-surface receptor, or a fragment, or a variant thereof, and the other of the at least two different proteins is represented by a polypeptide having a binding site to said receptor, wherein at least a part of said binding site comprises at least one of the sequences set forth in SEQ ID NOS: 1-146 or fragments, or variants, or homologues of said sequences, or fragments or variants of said homologues, comprising the steps of
i) providing a method for sequential screening the candidate compound as the defined above and/or
ii) providing a method for molecular design of the candidate compound as the defined above,
i) isolating the candidate compound The invention further discloses a series of peptide fragments having the sequences set forth in SEQ ID NOS: 2-146, said fragments i) being involved in a direct interaction with FGFR, or being representing a part of an FGFR binding site on a FGFR ligand, and/or ii) being capable of modulating the interaction between at least two different proteins, wherein one of the least two different proteins is represented by a functional cell-surface receptor, or a fragment, or a variant thereof, and the other of the at least two different proteins is represented by a polypeptide having a binding site to said receptor, wherein at least a part of said binding site comprises at least one of the sequences set forth in SEQ ID NOS: 1-146, or fragments, or variants, or homologues of said sequences, or fragments or variants of said homologues.

The invention also relates to a compound comprising the above peptide fragments and use of said compound for the preparation of a medicament.

Furthermore, the invention relates to
i) an antibody capable of binding to an epitope comprising a binding site for a cell surface receptor, wherein at least a part of said binding site comprises at least one of the sequences set forth in SEQ ID NOS: 1-146, or fragments, or variants, or homologues of said sequences, or a fragment or a variant of said antibody;
ii) an antibody capable of binding to an epitope comprising at least one of the sequences set forth in SEQ ID NOS: 1-146, or a fragment, or a variant of said antibody.

The invention also provides a method for the production of the above antibody. Furthermore, the invention also concerns the use of an antibody as the defined above for
1) the modulation of interaction between a cell surface receptor, or a fragment or variant thereof, and a polypeptide having a binding site to said receptor, wherein at least a part of said binding site comprises at least one of the sequences set forth in SEQ ID NOS: 1-146, or fragments, or variants, or homologues of said sequences, or fragments or variants of said homologues,
2) for the manufacture of a medicament
3) for determining the presence of a substance comprising an epitope comprising at least one of the sequences set forth in SEQ ID NOS: 1-146, or fragments, or variants, or homologues of said sequences, or fragments or variants of said homologues in a sample.

Finally, the invention relates to a method for producing a pharmaceutical composition comprising the steps of identifying of a candidate compound and further the step of formulating the compound capable of modulating modulation of interaction between a cell surface receptor, or a fragment or variant thereof, and a polypeptide having a binding site to said receptor, wherein at least a part of said binding site comprises at least one of the sequences set forth in SEQ ID NOS: 1-146, or fragments, or variants, or homologues of said sequences, or fragments or variants of said homologues with pharmaceutically acceptable carrier or solvent.

DESCRIPTION OF DRAWINGS

Table 1 presents a summary of NOE statistics, energy terms and deviations from the idealized geometry calculated from the NMR measurements.

with polyclonal antibody raised against the intact FGL-peptide measured by competitive ELISA.

Figure 11:
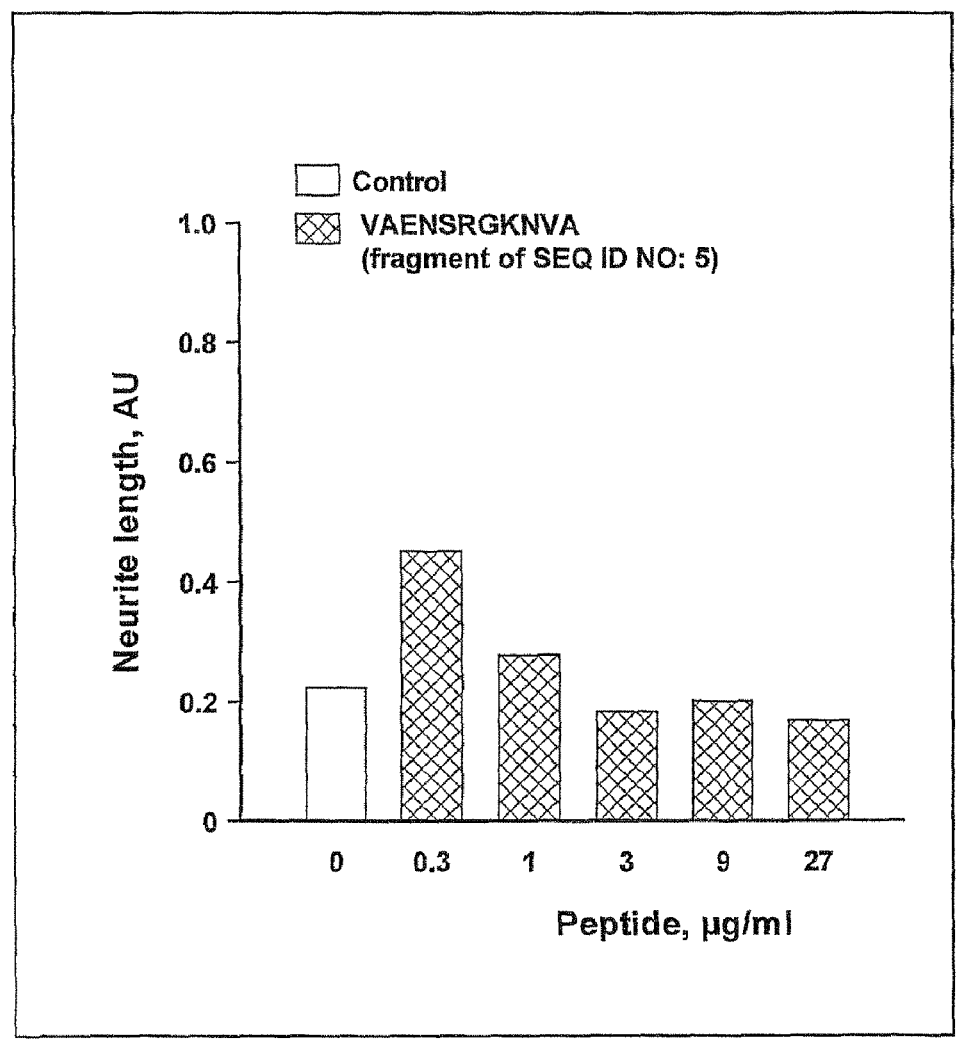

FIG. 11 presents the results of in vitro stimulation the neurite outgrowth of rat hippocampal neurons by a fragment (SEQ ID NO:171) of the sequence set forth in SEQ ID NO: 5 derived from the axonal-associated cell adhesion molecule. Treated cells are compared with cell received no treatment.

REFERENCES

Berezin, V., Bock, E., and Poulsen, F. M. (2000). The neural cell adhesion molecule. Curr. Opin. Drug. Disc. Dev. 3, 605-9.

Bodenhausen, G., and Ruben, D. J. (1980). Natural abundance nitrogen-15 NMR by enhanced heteronuclear spectroscopy. Chem. Phys. Lett. 69, 185-9.

Braunsweiler, L., and Ernst, R. R. (1983). Coherence transfer by isotropic mixing: application to proton correlation spectroscopy. J. Magn. Reson. 53, 521-8.

Chan, A. W., Hutchinson, E. G., Harris, D., Thornton, J. M. (1993). Identification, classification, and analysis of beta-bulges in proteins. Protein Sci. 2, 1574-90. for extracellular ATP and other nucleotides. Am. J. Physiol. 265, C577-606.

Dzhandzhugazyan, K., Bock, E. (1993). Demonstration of (Ca(2+)-Mg2+)-ATPase activity of the neural cell adhesion molecule. FEBS Lett. 336, 279-83.

Dzhandzhugazyan, K., Bock, E. (1997). Demonstration of an extracellular ATP-binding site in NCAM: functional implications of nucleotide binding. Biochemistry 36, 15381-95.

Eriksson, A. E., Cousens, L. S., Matthews, B. W. (1993). Refinement of the structure of human basic fibroblast growth factor at 1.6 A resolution and analysis of presumed heparin binding sites by selenate substitution. Protein Sci. 2, 1274-84.

Hatten, M. E., Lynch, M., Rydel, R. E., Sanchez, J., Joseph-Silverstein, J., Moscatelli, D., Rifkin, D. B. (1988). In vitro neurite extension by granule neurons is dependent upon astroglial-derived fibroblast growth factor. Dev. Biol. 125, 280-9.

Kiselyov, V. V., Berezin, V., Maar, T. E., Soroka, V., Edvardsen, K., Schousboe, A., Bock, E. (1997). The first immunoglobulin-like neural cell adhesion molecule (NCAM) domain is involved in double-reciprocal interaction with the second immunoglobulin-like NCAM domain and in heparin binding. J. Biol. Chem. 272, 10125-34.

Kjaer, M., Andersen, M. K., and Poulsen, F. M. (1994). Automated and semiautomated analysis of homo- and heteronuclear multidimensional nuclear magnetic resonance spectra of proteins: the program Pronto. Methods Enzymol. 239, 288-307.

Kumar, A., Wagner, G., Ernst, R. R., and Wüthrich, K. (1981). Buildup rates of the nuclear Overhauser effect measured by two-dimensional proton magnetic resonance spectroscopy: implications for studies of protein conformation. J. Am. Chem. Soc. 103, 3654-8.

Piantini, U., Sørensen, O. W., and Ernst, R. R. (1982). Multiple quantum filters for elucidating NMR coupling networks. J. Am. Chem. Soc, 104, 6800-1.

Powers, C. J., McLeskey, S. W., Wellstein, A. (2000). Fibroblast growth factors, their receptors and signaling. Endocr. Relat. Cancer 7, 165-97.

Skladchikova, G., Ronn, L. C., Berezin, V., Bock, E. (1999). Extracellular adenosine triphosphate affects neural cell adhesion molecule (NCAM)-mediated cell adhesion and neurite outgrowth. J. Neurosci. Res. 57, 207-18.

Thomsen, N. K., Soroka, V., Jensen, P. H., Berezin, V., Kiselyov, V. V., Bock, E., Poulsen, F. M. (1996). The three-dimensional structure of the first domain of neural cell adhesion molecule. Nat. Struct. Biol. 3, 581-5.

Williams, E. J., Furness, J., Walsh, F. S., Doherty, P. (1994). Activation of the FGF receptor underlies neurite outgrowth stimulated by L1, N-CAM, and N-cadherin. Neuron 13, 583-94.

Zhang, O., Kay, L. E., Oliver, J. P., and Forman-Kay, J. D. (1994). Backbone 1H and 15N resonance assignments of the N-terminal SH3 domain of drk in folded and unfolded states using enhanced-sensitivity pulsed field gradient NMR techniques. J. Biomol. NMR. 4, 845-58.

DETAILED DESCRIPTION OF THE INVENTION

Method for Modulation of Interaction Between Two Proteins

Cells of a multicellular organism communicate to each other and respond to a variety of signals of the cellular environment using an elaborate system of communication. This system enables a single cell to respond adequately to arrays of the signals by employing a finely tuned network of interactions between molecules of cell-surface receptors receiving the signals and the many cell-surface and intracellular proteins adapting and transmitting the signal into the cell. A minor intervention into a single interaction of this network may often lead to a major change in a specific cellular response to the extracellular signal.

Accordingly, the present invention relates in one aspect to a method of modulating the interaction between at least two different proteins, wherein one of the at least two different proteins is represented by a functional cell-surface receptor, or a fragment, or a variant thereof, and the other of the at least two different proteins is represented by a polypeptide having a binding site to said receptor, wherein at least a part of said binding site comprises at least one of the sequences set forth in SEQ ID NOS: 1-146, or fragments, or variants, or homologues of said sequences, or fragments or variants of said homologues, comprising i) providing a compound capable of interacting with the receptor and/or polypeptide thereby interfering with the interaction of said receptor and said polypeptide, ii) presenting the compound of step (i) to the at least two different proteins.

Thus, modulation of interaction between a functional cell-surface receptor and another protein is the first objective of the method of the invention.

In the present context by the term "interaction" is meant that a functional cell-surface receptor has a transient or permanent direct or indirect contact with another protein.

Functional Cell Surface Receptor

A cell-surface receptor is defined in the content of the present invention as any molecule comprising at least one polypeptide chain, said molecule being associated with the plasma membrane of a cell in such a way that enables said molecule to receive a signal at the outer side of the membrane, transduce the signal through the membrane, and convey said signal further by inducing a certain action on molecular level inside the cell, for example by inducing association or dissociation of molecular complexes, or initiating a biochemical reaction, for example auto-phosphorylation of the receptor, or proteolytic cleavage of the receptor leading to initiation of intracellular signal transduction.

The invention designates to a "functional cell-surface receptor". "Functional cell-surface receptor" is meant that the cell-surface receptor of the invention has an identifiable group of ligands, the binding of these ligands to the receptor induces intracellular signal transduction, which results in a physiological response of the cell. The physiological response, such as for example differentiation, proliferation, survival, apoptosis or motility of a cell, depends on the ligand that is involved in the interaction with the receptor, and/or characteristics of said interaction, such as the affinity or duration, and/or a species of the cell which expresses the receptor. By the term "ligand" is defined a compound which is capable to bind to the receptor and thereby to activate said receptor. "Activation" of a receptor is meant that after extracellular binding of a ligand the receptor became capable to transmit the effect of "ligand binding" into a cascade of biochemical reactions collectively termed "receptor signaling" or "signal transduction" inside the cell resulting in one of the above mentioned physiological responses of the cell.

A capability of a cell-surface receptor to induce and/or maintain a cellular process upon the ligand binding is herein termed "biological function" of the receptor.

The functional cell-surface receptor of the invention, which recognises and interacts with another protein, is, in a preferred embodiment, a receptor of the family of fibroblast growth factor receptors (FGFRs) comprising FGFR1, FGFR2, FGFR3 and FGFR4. In the most preferred embodiment a cell-surface receptor of the invention is FGFR1 or a functional homologue thereof.

By the term "functional homologue of the receptor" is meant a molecule which is capable of
i) extracellular binding of a ligand of FGFR and thereby activating the receptor dependent signal transduction cascade in the cell, and/or
ii) intracellular binding of an adaptor molecule of FGFR and thereby activating the receptor dependent signal transduction cascade in the cell.

The term "binding" refers to a direct or indirect interaction between an FGFR homologue and a counter molecule having a binding site for FGFR. In the present context the counter molecule is an extracellular ligand of FGFR, or an intracellular adaptor molecule. An "adaptor molecule" is defined in the content of the invention as a molecule, which is capable to recognize an "active state" of the receptor, selectively bind to such receptor and convey the signal of "activated receptor" in the cell by inducing a cascade of reactions of signal transduction. An intracellular adaptor molecule may be represented by for example STN, FRS, Grb, SHP2, PLCγ, or PIP3.

The invention relates to ligands having a relatively low affinity to FGFR. The affinity means the strength of attraction between molecules. The ligand of FGFR in the present context is determined as a molecule, which comprises at least one binding site to FGFR and is capable of low affinity binding to the receptor. Thus, according to the invention, the other protein, which is involved in interaction with the cell-surface receptor is in one aspect a ligand of FGFR.

Binding Site

According to the invention a cell-surface receptor interacts with another protein through a receptor binding site, said binding site being located on said another protein. The binding site of a molecule may be defined as a specific part of said molecule, which is involved in interaction with another molecule. In the present context "binding site" is defined as a fragment of a protein, specific features of which confer on the protein a capacity to interact directly and selectively with another molecule, for example a receptor molecule. Under "specific features" in the present context is understood a particular amino acid sequence or the three-dimensional structure of that fragment of a protein which is referred as the binding site. By the term "selectively" in the present context is meant that the binding site is involved in interaction with the certain molecule or certain group of molecules, said molecule(s) having a specific structure which makes said molecule(s) capable to recognise the binding site and interact with it.

In one embodiment the present invention features a binding site to a cell-surface receptor, wherein at least a part of said binding site comprises at least one of the sequences set forth in SEQ ID NOS: 1-146, or fragments, or variants, or homologues of said sequences, or fragments or variants of said homologues, such as the fragments, variants and homologues defined below.

In another embodiment the binding site comprises, or at least part of said binding site comprises at least one of the sequences set forth in SEQ ID NOS: 1-10, 100, 125, such as for example SEQ ID NOS: 2-10, 100, 125, or fragments or variants, or homologues said sequences, or fragments or variants of said homologues. The present invention relates to fragments having at least 40%, more preferably at least 50%, more preferably at least 60%, more preferably at least 70%, more preferably at least 80%, more preferably at least 90%, more preferably at least 95% of the length of a predetermined sequence set forth in SEQ ID NOS: 1-10, 100, 125, or SEQ ID NOS: 2-10, 100, 125, wherein an amino acid sequence homology between a fragment and the predetermined sequence is 100%. A variant in the present context is defined as an amino acid sequence having at least 60%, more preferably at least 70%, more preferably at least 80%, more preferably at least 90%, more preferably 95% homology to a sequence selected from SEQ ID NOS: 1-10, 100, 125, or SEQ ID NOS: 2-10, 100, 125, or an amino acid sequence having at least 60%, more preferably at least 70%, more preferably at least 80%, more preferably at least 90%, more preferably 95% positive amino acid matches compared to a sequence selected from SEQ ID NOS: 1-10, 100, 125, or SEQ ID NOS: 2-10, 100, 125. A positive amino acid match is defined as an identity or similarity defined by physical and/or chemical properties of the amino acids having the same position in two compared sequences. Preferred positive amino acid matches of the present invention are K to R, E to D, L to M, Q to E, I to V, I to L, A to S, Y to W, K to Q, S to T, N to S and Q to R. The homology of one amino acid sequence with another amino acid is defined as a percentage of identical amino acids in the two collated sequences. A homologue in the present context is defined as an amino acid sequence which has less then 60% and more then 19%, such as 50-59%, for example 55%, such as 40-49%, for example 45%, such as 30-39%, for example 35%, such as 20-29%, for example 25% homology to any of the sequences set forth in SEQ ID NOS: 1-10, 100, 125, or SEQ ID NOS: 2-10, 100, 125 having remained some of the physical properties of the predetermined sequences, such as for example the three-dimensional structure or some of the functional properties, such as for example a capability to interact with another molecule, in particular with a receptor molecule. A variant of a homologue in the present context is defined as an amino acid sequence having at least 60%, more preferably at least 70%, more preferably at least 80%, more preferably at least 90%, more preferably 95% positive amino acid matches compared to a homologue of any of the sequences selected from SEQ ID NOS: 1-10, 100, 125, or SEQ ID NOS: 2-10, 100, 125. Preferred embodiments of the positive amino acid matches is as the defined above. The invention concerns the fragments, variants and homologues, which remain a capability of the predetermined sequences to interact with the cell-surface receptor defined above.

In still another embodiment the invention features a binding site comprising at least one variant, or fragment, or homologue of any of the sequences set forth in SEQ ID NOS: 1-10, 100, 125, or SEQ ID NOS: 2-10, 100, 125, said variant, or fragment, or homologue being preferably selected from the sequences identified in SEQ ID NOS: 11-99, 101-124, 126-146.

The described above binding site is according to invention characterised by specific structural features. The invention preferably features a binding site, which essentially consists of one or more "strand-loop-strand" structural motifs.

Side chains of the amino acids in a contiguous amino acid sequence interact to each other. The numerous interactions-lead to folding the amino acid sequence into a specific structural pattern, such as α-helix and β-strand, which is usually determined by the amino acids of the sequence. Interactions between amino acids of the individual patterns hold the long amino acid sequence of a polypeptide folded in a compact tertiary structure. In a tertiary structure the amino acid sequence of a polypeptide tends to wind its way back and forth across the entire structure, either as an α-helix or β-strand, reversing its direction suddenly by making a turn and creating thus the loop regions. The loop regions, which may vary in length and have irregular shape, often form biding sites for other molecules. The present invention concerns a binding site, which comprises at least one loop region. It is preferred, if the at least one loop region in the binding site connects two interacting β-strands forming thereby a "strand-loop-strand" structural motif. By the term "motif" in the present content is meant a unit of the polypeptide chain of a protein having the defined sequence of amino acids of certain length and/or characterised by specific structural features and/or (optionally) having certain functional capabilities common for a group of proteins.

Polypeptide Comprising a Binding Site

As it has been mentioned above, certain combinations of α-helices and β-strands pack together and form a compactly folded tertiary structure of the protein. If the protein comprises a long amino acid sequence, such as for example more then 100 amino acids, its tertiary structure may consist of several modular units, each of which is called a protein domain. Domains are usually constructed from a section of polypeptide chain that contains between 50 and 350 amino acids. Because there is only a limited number of ways of combining α-helices and β-strands to make a globular structure, certain combinations of these elements may occur repeatedly in the core of related and also unrelated proteins bestowing some common structural features on these proteins. The present invention contemplates both the proteins having common structural characteristics, structurally related proteins, and structurally unrelated proteins. In a preferred embodiment the invention concerns at least two different proteins capable of interacting to each other, wherein at least one of the at least two proteins comprises at least two immunoglobulin (Ig)-like domains and/or at least two fibronectin type 3 (F3) domains, or at least one Ig-like domain and at least one F3 domain.

According to the invention a functional cell-surface receptor interacts with another protein. The invention preferably relates to the interaction between a cell-surface receptor and a heterologous protein. By the term "heterologous" in the present context is meant a protein the amino acid sequence of which has at most 40% homology and/or at most 50% of positive amino acid matches with the amino acid sequence of a polypeptide chain of the receptor. Preferably said heterologous protein itself is not capable to execute any biological function of the receptor. A heterologous protein is preferably an extracellular protein or a protein, at least part of which is exposed to the extracellular space. However, any heterologous protein which has more then 40% homology and/or more then 50% of positive amino acid matches with the amino acid sequence of a polypeptide chain of the receptor is in the scope of the invention, if said protein comprises a binding site to the receptor described above.

The present invention relates to a heterologous protein comprising the above described binding site, which is preferably selected from the group comprising transmembrane, cell-surface associated, extracellular matrix associated or soluble proteins.

A protein is in the present context defined as "transmembrane" if at least one part of the polypeptide chain of said protein is positioned extracellularly, at least one part of the polypeptide chain of said protein is represented by the plasma membrane spanning domain, and at least one part of the polypeptide chain of said protein is positioned intracellularly, wherein the at least one extracellular part is connected with the at least one intracellular part via the at least one membrane spanning domain.

In the present context "plasma membrane associated protein" is defined as a protein having a direct or indirect contact with the plasma membrane. The "direct" contact is meant that the protein has an immediate connection with the membrane assisted by a moiety covalently attached to said protein, such as for example a lipid moiety, for example glycosylphosphatidylinositol or a fatty acid moiety. The "indirect" contact is meant that the protein has a connection with the membrane through another molecule which said protein is associated with in a complex, for example another protein, lipopolysaccharide or proteoglycan molecule.

The extracellular matrix associated protein in the present context is defined as a protein, or a molecule comprising a polypeptide chain, said protein or said molecule being attached to a component of the extracellular matrix through a chemical bond, or said protein or said molecule itself being an immediate component of the extracellular matrix.

The soluble protein in the present context is meant a protein, which is present free in solution in the extracellular space, such as for example a secreted protein, or a shed protein produced due to extracellular proteolysis of the membrane associated protein.

Furthermore, the invention features particular polypeptides from the above groups, which are preferably selected from cell adhesion molecules, cell-surface receptors, proteoglycans, membrane-anchored cell-surface proteolytic enzymes, extracellular matrix molecules, or growth factors.

Thus, in one embodiment the polypeptide of the invention is selected from the group of cell adhesion molecules comprising Neural Cell Adhesion Molecule (NCAM) (Swiss-Prot Ass. Nos: P13591, P13595-01, P13595), Neural cell adhesion molecule L1 (Swiss-Prot Ass. Nos: Q9QYQ7, Q9QY38, P11627, Q05695, P32004), Neural Cell Adhesion Molecule-2 (NCAM-2) (Swiss-Prot Ass. No: P36335)

Neuron-glia Cell Adhesion Molecule (Ng-CAM) (Swiss-Prot Ass. No: Q03696; Q90933), Neural cell adhesion molecule CALL (Swiss-Prot Ass. No: O00533), Neuroglian (Swiss-Prot Ass. No: P91767, P20241), Nr-CAM (HBRAVO, NRCAM, NR-CAM 12) (Swiss-Prot Ass. Nos: Q92823, O15179, Q9QVN3

Axonin-1/TAG-1 (Swiss-Prot Ass. Nos: Q02246, P22063, P28685),

Axonal-associated Cell Adhesion Molecule (AxCAM) (NCBI Ass. No: NP_031544.1; Swiss-Prot Ass. No: Q8TC35), Myelin-Associated Glycoprotein (MAG) (Swiss-Prot Ass. No: P20917),
Neural cell adhesion molecule BIG-1 (Swiss-Prot Ass. No: Q62682),
Neural cell adhesion molecule BIG-2 (Swiss-Prot Ass. No: Q62845),
Fasciclin (FAS-2) (Swiss-Prot Ass. No: P22648),
Neural cell adhesion molecule HNB-3/NB-3 (Swiss-Prot Ass. Nos: Q9UQ52, P97528, Q9JMB8)
Neural cell adhesion molecule HNB-2/NB-2 (Swiss-Prot Ass. Nos: O94779, P07409, P97527),
Cadherin (Swiss-Prot Ass. No: Q9VW71),
Junctional Adhesion Molecule-1 (JAM-1)(Swiss-Prot Ass. Nos: Q9JKD5, O88792),
Neural cell adhesion F3/F11(Contactin) (Swiss-Prot Ass. Nos: Q63198, P1260, Q12860, Q28106, P14781, O93250),
Neurofascin (Swiss-Prot Ass. Nos: Q90924, Q91Z60; O42414),
B-lymphocyte cell adhesion molecule CD22 (Swiss-Prot Ass. Nos: Q9R094, P20273),
Neogenin (NEO1) (Swiss-Prot Ass. Nos: Q92859, P97603, Q90610, P97798),
Intercellular Cell Adhesion Molecule-5 (ICAM-5/telencephalin) (Swiss-Prot Ass. Nos: Q8TAM9, Q60625) or
Galactose binding lectin-12 (galectin-12) (Swiss-Prot Ass. Nos: Q91VD1, Q9JKX2, Q9NZ03),
Galactose binding lectin-4 (galectin-4) (Swiss-Prot Ass. No: Q8K419; P38552) or fragments, or variants thereof.

In another embodiment the polypeptide is selected from the group of functional cell-surface receptors comprising
Fibroblast Growth Factor Receptor 1 (FGFR1) (Swiss-Prot Ass. Nos: Q9QZM7, Q99AVV7, Q9UD50, Q63827),
Fibroblast Growth Factor Receptor 2 (FGFR2) (Swiss-Prot Ass. Nos: Q96KM2, P21802, Q63241),
Fibroblast Growth Factor Receptor 3 (FGFR3) (Swiss-Prot Ass. Nos: Q95M13, AF487554, Q99052),
Fibroblast Growth Factor Receptor 4 (FGFR4) (Swiss-Prot Ass. No: Q91742),
Neurotrophin Tyrosin Kinase Type-2 (NTRKT-2) (Swiss-Prot Ass. No: Q8WXJ5),
Leukocyte Antigen Related Protein-Tyrosine Phosphatase (LAR-PTPRF) (Swiss-Prot Ass. Nos: Q9EQ17, Q64605, Q64604, Q9QW67, Q9VIS8 P10586),
Nephrin (Swiss-Prot Ass. Nos: Q925S5, Q9JIX2, Q9ET59, Q9R044, Q9QZS7, Q06500),
Protein-Tyrosine Phosphatase Receptor type S (PTPRS) (Swiss-Prot Ass. Nos: Q64699, Q13332, O75870),
Protein-Tyrosine Phosphatase Receptor type kappa (R-PTP-kappa) (Swiss-Prot Ass. No: Q15262),
Protein-Tyrosine Phosphatase Receptor type D (PTPRD) (Swiss-Prot Ass. Nos: Q8WX65, Q9IAJ1, P23468, Q64487),
Ephrin type-A receptor 8 (EPHA8/Tyrosine-Protein Kinase Receptor EEK) (Swiss-Prot Ass. Nos: O09127, P29322),
Ephrin type-A receptor 3 (EPHA8/Tyrosine-Protein Kinase Receptor ETK-1/GEK4) (Swiss-Prot Ass. No: P29318),
Ephrin type-A receptor 2 (Swiss-Prot Ass. No: Q8N3Z2)
Insulin Receptor (IR) (Swiss-Prot Ass. No: Q9PWN6)
Insulin-like Growth Factor-1 Receptor (IGF-1) (Swiss-Prot Ass. Nos: Q9QVW4, P08069, P24062, Q60751, P15127, P15208)
Insulin-related Receptor (IRR) (Swiss-Prot Ass. No: P14616),
Tyrosine-Protein Kinase Receptor Tie-1 (Swiss-Prot Ass. Nos: 06805, P35590, Q06806),
Roundabout receptor-1 (robo-1) (Swiss-Prot Ass. Nos: O44924, AF041082, Q9Y6N7),
Neuronal nicotinic acetylcholine receptor alpha 3 subunit (CHRNA3) (Swiss-Prot Ass. Nos: Q8VHH6, P04757, Q8R4G9, P32297)
Neuronal acetylcholine receptor alpha 6 subunit (Swiss-Prot Ass. Nos: Q15825, Q9R0W9)
Platelet-Derived Growth Factor Receptor Beta (PDGFRB) (Swiss-Prot Ass. Nos: Q8R406, Q05030),
Interleukin-6 Receptor (IL-6R) (Swiss-Prot Ass. No: Q00560),
Interleukin-23 Receptor (IL-23R) (Swiss-Prot Ass. No: AF461422),
Beta-common cytokine receptor of IL-3, IL5 and GmCsf (Swiss-Prot Ass. No: P32927)
Cytokine Receptor-Like molecule 3 (CRLF1) (Swiss-Prot Ass. No: Q9JM58),
Class I Cytokine Receptor (ZCYTOR5) (Swiss-Prot Ass. No: Q9UHH5)
Netrin-1 receptor DCC (Swiss-Prot Ass. No: P43146),
Leukocyte Fc Receptor-like Protein (IFGP2) (Swiss-Prot Ass. Nos: Q96PJ6, Q96KM2),
Macrophage Scavenger Receptor 2 (MSR2) (Swiss-Prot Ass. No: Q91YK7), or
Granulocyte Colony Stimulating Factor Receptor (G-CSF-R) (Swiss-Prot Ass. No: Q99062),
or fragments, or variants thereof.

In still another embodiment the polypeptide is selected from the group of proteoglycans. More preferably the proteoglycan is selected from the group comprising heparan sulphate proteoglycans. In the most preferred embodiment the proteoglycan is perlecan (Swiss-Prot Ass. No: P98160), or a fragment, or a variant thereof.

It is also another embodiment to select the polypeptide from the group of membrane-anchored cell-surface proteolytic enzymes. Preferably the polypeptide is selected from the group comprising the pitrilysin family of metalloproteinases or the family of desintegrin and metalloproteases (AD-AMs) comprising
ADAM-8 (Swiss-Prot Ass. No: Q05910),
ADAM-19 (Swiss-Prot Ass. Nos: Q9H013, O35674),
ADAM-8 (Swiss-Prot Ass. No: P78325),
ADAM-12 (Swiss-Prot Ass. Nos: O43184, Q61824),
ADAM-28 (Swiss-Prot Ass. Nos: Q9JLN6, Q61824, Q9XSL6, Q9UKQ2),
ADAM-33 precursor (Swiss-Prot Ass. Nos: Q8R533, Q923W9),
ADAM-9 (Swiss-Prot Ass. Nos: Q13433, Q61072),
ADAM-7 (Swiss-Prot Ass. Nos: Q9H2U9, O35227, Q63180),
ADAM-1A Fertilin alpha (Swiss-Prot Ass. No: Q8R533),
ADAM-15 (Swiss-Prot Ass. Nos: Q9QYV0, O88839, Q13444),
Metalloproteinase-desintegrin domain containing protein (TECAM) (Swiss-Prot Ass. No: AF163291),
Metalloproteinase 1 (Swiss-Prot Ass. Nos: O95204, Q9BSI6),
or fragments, or variants thereof.

In yet another embodiment, the polypeptide is selected from the group of etracellular matrix molecules comprising
Collagen type VII (Swiss-Prot Ass. No: Q63870),
Fibronectin (Swiss-Prot Ass. Nos: Q95 KV4, Q95 KV5, P07589, Q28377, U42594, O95609, P07589, P11276), or Tenascin (Swiss-Prot Ass. Nos: Q15568, O00531, P10039, Q90995), or fragments, or variants thereof.

In still yet another embodiment the polypeptide is selected from the group of growth factors. In the most preferred embodiment the growth factor is Cytokine-like factor-1 (CLF-1) (Swiss-Prot Ass. No: O75462), or a fragment, or a variant thereof.

In further another embodiment the polypeptide is selected from the group of soluble proteins. In the most preferred embodiment the soluble protein is SPLIT (Swiss-Prot Ass. No: Q9XYV4).

In the most preferred embodiment, the polypeptide is the neural cell adhesion molecule, NCAM, having the sequence identified in Swiss-Prot Ass. Nos: P13591, P13595-01 or P13595.

By the wording "fragments, or variants" of the above polypeptides is meant
(i) polypeptide(s) essentially consisting of the amino acid sequence of the predetermined polypeptide, wherein the length of amino acid sequence of said polypeptide(s) being shorter or longer then the length of said predetermined polypeptide, said polypeptide(s) being capable to interact with the functional cell-surface receptor according to invention and/or
(ii) polypeptide(s) comprising at least a fragment of the amino acid sequence of the predetermined polypeptide, or a fragment of a sequence having at least 60% homology to the sequence of said predetermined polypeptide, wherein the length of said fragment consists of at least 25% of the length of the predetermined polypeptide, said polypeptides being capable of interacting with the functional cell-surface receptor according to invention, and/or
(iii) polypeptides essentially having the features described in prior art for the predetermined polypeptide, said features being essential for the interaction of said polypeptides with the cell-surface receptor according to invention, and/or
(iv) polypeptides lacking one or more features described in prior art for the predetermined polypeptide, said polypeptides being capable of interacting with the functional cell-surface receptor according to invention.

Such fragments or variants may be selected from, but not limited by examples of naturally occurring isoforms of the above polypeptides, pro-polypeptides, proteolytic fragments of the above polypeptides, corresponding recombinant polypeptides or fusion proteins containing amino acid sequences derived from the above polypeptides.

Affinity of Interaction

Any interaction between two molecules may be characterised by its affinity, which means the strength of attraction between two molecules. The affinity of interaction is commonly expressed by a value of Kd, a dissociation equilibrium constant. Kd reflects a ratio between the rate of dissociation and the rate of binding between two molecules and thus represents a measure of the strength of binding between two molecules. The stronger the binding, the lower is the value of Kd. The invention relates to a low affinity interaction between a cell-surface receptor and another protein, such as the defined above. The low affinity interaction of the invention is characterised by Kd having a value in the range of $10^{-3}$ to $10^{-10}$, such for example in the range of $10^{-4}$ to $10^{-8}$.

According to the invention affinity of the interaction is determined by surface plasmon resonance analysis (SPR) or nuclear magnetic resonance spectroscopy (NMR).

Modulation of Interaction

By the term "modulation" in relation to interaction between two molecules is meant a change in the strength of interaction, such as either a decrease or increase in the strength of interaction. Modulation of interaction takes place when it is important to adjust the strength of interaction between molecules adequately to a change in the situation dependent on said interaction. For example, modulating the strength of interaction between a receptor and receptor ligand makes possible the modulating the receptor dependent signal transduction and thereby the physiological status of the cell.

By "modulating receptor signalling" is meant activation or inhibition of the production of a cascade of messenger molecules, which normally takes place in the cell in response to activation of the receptor by an extracellular stimulus.

The receptor signaling leads to a physiological response of the cell. Therefore, modulating the strength of interaction between a receptor and the receptor ligand, otherwise termed "strength of receptor stimulation", makes possible to modulate the receptor signaling, and thereby a physiological response of the cell. It has been shown that the cellular response to stimulation of a receptor depends on the strength of receptor stimulation, which may, for example, be characterised by the value of affinity of interaction of the receptor with a ligand, and/or by the duration of such interaction. The both affinity and duration of interaction may be affected if the interacting molecules are exposed to a compound capable of modulating the interaction.

Compound

The present invention relates to a compound, which is capable of
i) interacting with a cell-surface receptor thereby mimicking the interaction of the receptor with a ligand, and/or
ii) interacting with a cell-surface receptor thereby interfering with the interaction of the receptor and the receptor ligand, and/or
iii) interacting with a cell-surface receptor ligand thereby interfering with the interaction of the receptor ligand and the receptor, and/or
iv) simultaneous interacting with a cell-surface receptor and the receptor ligand thereby interfering with the interaction of the receptor and the receptor ligand, and/or
v) interacting with a molecule which is involved in assistance of the interaction between a cell-surface receptor and the receptor ligand thereby interfering with the interaction the receptor and the receptor ligand.

The invention in one aspect relates to compounds that are capable to interact with a site on the receptor, which is involved in interaction of the receptor with a ligand, or are capable to interact with a receptor binding site in the ligand molecule. In another aspect the invention relates to compounds that are capable to bind to another sites in the receptor or ligand presuming that such interaction will interfere with the interaction of the receptor and the ligand.

The invention features any compounds capable of the above bindings. However, preferred compounds of the invention are selected from the group comprising peptides, carbohydrates, lipids or nucleotides. Among the preferred compounds the most preferred are peptide or nucleotide compounds.

Accordingly, in one embodiment, the invention relates to a compound selected from the group comprising nucleotides, nucleotide analogues, nucleotide derivatives, di- or oligomers of nucleotides, or nucleotide comprising substances. Preferably a nucleotide is selected from the group comprising nucleotide triphosphates. More preferably a nucleotide triphosphate is selected from the group comprising UTP, GTP, CTP, TTP and ATP or analogues, derivatives, di- or oligomers thereof, or substances comprising thereof. The most preferred nucleotide of the invention is ATP or an analogue thereof. A nucleotide analogue is defined as a molecule comprising a nucleotide base or a modified nucleotide base, a sugar residue or a modified sugar residue and a mono-, di-, tri-, quadra-, or penta-ester group. It is one of preferred embodiments of the invention if a nucleotide analogue possesses an increased stability in an aquatic solution in vitro and/or an increased stability in an ezymatic system comprising an enzyme capable of utilising a nucleotide as a substrate. The content of a cell is an example of such ezymatic system. The invention preferably relates to stable nucleotide triphosphate analogues, wherein at least one phosphorus group in the triphosphate ester is substituted for another chemical group, such for example CH—, S—, or NH— group.

In another embodiment, the invention relates to a compound, which comprises a nucleotide. In a more preferred embodiment the compound comprises ATP, or an analogue thereof.

A peptide compound of the invention may be any contiguous amino acid sequence, that meets the requirements for a compound defined above. Preferably a peptide compound comprises at least one of the sequences identified in SEQ ID NOS: 2-10, 100, 125, or a peptide fragment derived from any of said sequences. By the term "derived" in the present context is meant that the peptide compound may be represented by an amino acid sequence comprising a variant, or a fragment, or a combination of any of the sequences identified in SEQ ID NOS: 2-10, 100, 125, or a combination of variants, or fragments thereof. The present invention relates to fragments having at least 40%, more preferably at least 50%, more preferably at least 60%, more preferably at least 70%, more preferably at least 80%, more preferably at least 90%, more preferably at least 95% of the length of a predetermined sequence set forth in SEQ ID NOS: 2-10, 100, 125, wherein an amino acid sequence homology between a fragment and the predetermined sequence is 100%. A variant in the present context is defined as an amino acid sequence having at least 60%, more preferably at least 70%, more preferably at least 80%, more preferably at least 90%, more preferably 95% homology to a sequence selected from SEQ ID NOS: 2-10, 100, 125, or an amino acid sequence having at least 60%, more preferably at least 70%, more preferably at least 80%, more preferably at least 90%, more preferably 95% positive amino acid matches compared to a sequence selected from SEQ ID NOS: 2-10, 100, 125. A homology of one amino acid sequence with another amino acid is defined as a percentage of identical amino acids in the two collated sequences. A positive amino acid match is defined as an identity or similarity defined by physical and/or chemical properties of the amino acids having the same position in two collated sequences. Preferred positive amino acid matches of the present invention are K to R, E to D, L to M, Q to E, I to V, I to L, A to S, Y to W, K to Q, S to T, N to S and Q to R. A combination of amino acid sequences may either be represented by a homopolymer or a heteropolymer of said sequences, wherein said homopolymer being represented a sequence comprising one or more repeats of any of the sequences selected from SEQ ID NOS: 2-10, 100, 125, and said homopolymer being represented by a sequence comprising one or more repeats of at least two different sequences selected from SEQ ID NOS: 2-10, 100, 125. A number of repeats in the sequences in a homopolymer, or a heteropolymer may vary from 2 to 20, for example 15, such as 2 to 15, for example 10, such as 2 to 10, for example 3, 4, 5, 6, 7, 8, or 9.

Another preferred peptide compounds of the invention are those that comprise at least one of the sequences selected from SEQ ID NOS: 11-99, 101-124, 126-146, a fragment, variant or homologue thereof.

According to the invention sequences identified as SEQ ID NOS: 1-146 are derived from the sequences of FGFR receptor ligands and involved in interaction of the receptor with said ligands. Therefore, any of the sequences selected from SEQ ID NOS: 1-146 may anticipated being capable of modulating the interaction between FGFR and FGFR ligand, said ligand comprising the binding site of the invention.

The amino acid sequence of the peptide compound of the invention may be of any suitable length, in that the length of the amino acid sequence is dictated by the functionality of the peptide and the formulation of the compound into a pharmaceutical composition. Thus, the compound normally comprises amino acid residues in the range of from 3-100 amino acid residues, such as from 10-90 amino acid residues, for example from 15-85 amino acid residues, such as from 20-80 amino acid residues, for example from 25-75 amino acid residues, such as from 30-70 amino acid residues, for example from 35-65 amino acid residues, such as from 40-60 amino acid residues, for example from 45-55 amino acid residues.

In another aspect the peptide compound comprises amino acid residues in the range of from 3 to 20 amino acid residues, such as from 3-19 amino acid residues, for example from 3-18 amino acid residues, such as from 3-17 amino acid residues, for example from 3-16 amino acid residues, such as from 3-15 amino acid residues, for example from 3-14 amino acid residues, such as from 3-13 amino acid residues.

In still another aspect the peptide compound encompasses a sequence of at least 6 to 16 contiguous amino acids, such as for example 7, 8, 9, 10, 11, 12, 13, 14 or 15 amino acids.

In yet another aspect the amino acid sequence of a peptide compound is capable of forming a strand-loop-strand fold analogous to the strand-loop-strand motif of the described above binding site of the invention.

A compound of the present invention may preferably be in the form of an oligomer (multimer) of monomers, wherein each monomer is as a peptide compound defined above. Particularly, multimeric peptides such as dendrimers may form conformational determinants or clusters due to the presence of multiple flexible peptide monomers. In one embodiment the compound is a dimer. In a more preferred embodiment the compound is a dendrimer, such as four peptides linked to a lysine backbone, or coupled to a polymer carrier, for example a protein carrier, such as BSA. Polymerisation such as repetitive sequences or attachment to various carriers are well-known in the art, e.g. lysine backbones, such as lysine dendrimers carrying 4 peptides, 8 peptides, 16 peptides, or 32 peptides. Other carriers may be lipophilic dendrimers, or micelle-like carriers formed by lipophilic derivatives, or starburst (star-like) carbon chain polymer conjugates.

The individual monomers may be homologous, i.e. identical to one another, or the individual monomers may be heterologous, i.e. different from one another. The latter type of monomers may comprise at least two different monomers. In general dimers and multimers may comprise two or more identical monomers, or two or more monomers different from one another.

Screening Method

It is an important aspect of the invention to provide a screening method for a candidate compound capable of modulating the interaction between at least two different proteins, wherein one of the at least two different proteins is represented by a functional cell-surface receptor, or a fragment, or a variant thereof, and another of the at least two different proteins is represented by a polypeptide having a binding site to said receptors wherein at least a part of said binding site comprises at least one of the sequences set forth in SEQ ID NOS: 1-146, or fragments, or variants, or homologues of said sequences, or fragments or variants of said homologues, comprising
i) providing the at least two different proteins;
ii) providing a compound;
iii) presenting the compound of (ii) to the at least two different proteins of (i);
iv) determining the interaction between the at least two different proteins before and after the presenting the candidate compound to said proteins;
v) determining whether the interaction between the at least two different proteins has been modulated by the presented compound;
vi) selecting a candidate compound capable of modulating the interaction between the at least two different proteins.

The screening method according to invention concerns in a preferred embodiment identification of a candidate compound capable of modulating the interaction between a cell-surface receptor, wherein the receptor is FGFR, and a polypeptide, wherein the polypeptide is a FGFR ligand. More preferably FGFR is FGFR1 having the amino acid sequence identified in Swiss-Prot Seq Nos: Q9QZM7, Q99AVV7, Q9UD50 or Q63827, or fragments, or variants thereof, or a functional homologue of said receptor. The FGFR ligand is preferably selected from the FGFR1 ligands, polypeptide chain of which comprises the described above binding site. Examples of preferred polypeptides are described above. The most preferred polypeptide for the screening method of the invention is the neural cell adhesion molecule, NCAM, having the amino acid sequence identified as Swiss-Prot Ass Nos: P13591, P13595-01 or P13595, or fragments, or variants thereof, a functional homologue thereof.

Screening Assay

Modulation of a receptor-ligand interaction may be assessed by using a number of in vitro assays developed in the art. However, there are no any universal approach in selection of these assays for estimation of the capability of candidate compounds to modulate the interaction between different receptors and their ligands. The present invention provides an assay for sequential screening of a candidate compound capable of modulating the interaction between at least two different proteins, wherein one of the least two different proteins is represented by a functional cell-surface receptor, or a fragment, or a variant thereof, and another of the at least two different proteins is represented by a polypeptide having a binding site to said receptor, wherein at least a part of said binding site comprises at least one of the sequences set forth in SEQ ID NOS: 1-146, or fragments, or variants, or homologues of said sequences, or fragments or variants of said homologues, comprising the steps of
i) providing the at least one functional cell-surface receptor molecule, or a fragment, or a variant thereof, and the at least one polypeptide having a binding site to said receptor, wherein at least a part of said binding site comprises at least one of the sequences set forth in SEQ ID NOS: 1-146, or fragments, or variants, or homologues of said sequences, or a fragments or a variants of said homologues,
ii) presenting the at least one receptor molecule of step (i) to the at least one polypeptide of step (i), or presenting the at least one polypeptide of step (i) to the at least one receptor molecule of step (i) and permitting the interaction between said receptor and said polypeptide, followed by the
iii) recording the interaction between the molecules of step (ii),
iv) presenting the candidate compound to the molecules of step (ii);
v) recording the interaction between the molecules of step (iv), followed by the
vi) assessment of at least one effect of the candidate compound on the interaction between the molecules of step (iv), followed by the
vii) selection of a compound capable of modulating the interaction between the at least one functional cell-surface receptor molecule and the at least one polypeptide of step (i).

By the term "permitting the interaction" in the present content is meant that conditions of step (ii) include a suitable medium in which the interaction is favoured and long enough time interval to allow the molecules to interact.

The steps (ii)-(v) of the above assay may optionally be performed as the following: (ii) presenting the compound to the at least one receptor molecule of step (i) or presenting the compound to the at least one polypeptide of step (i), (iii) presenting at least one polypeptide of step (i) to the compound and receptor of step (ii) or presenting the at least one receptor molecule to the compound and polypeptide of step (i), (iv) recording the interaction between the molecules of step (iii). If the latter option is used, a candidate compound is selected when no interaction between the molecules of step (iii) has been recorded or the recorded interaction has been modulated compared to the interaction between said molecules in the absence of said compound. It is presumed that parameters of interaction between the receptor and the polypeptide in the absence of the compound have been assessed using any of the described below methods before performing the modified assay.

The described above assay is preferably provided by the invention for the sequential screening of a candidate compound capable of modulation of interaction between FGFR1 and the FGFR1 ligand, said ligand being one of the polypeptides described above. In a preferred embodiment the ligand is NCAM.

Assessment of the effect of a candidate compound on the interaction between the molecules for the assay may be done by using a conventional method of the art, such as for example surface plasmon resonance analysis (SPR), nucleic magnetic resonance spectroscopy (NMR), sedimentation analysis, immunoprecipitation, two-hybrid system, or resonance energy transfer (BRET or FRET). A candidate compound capable of modulating the interaction may be selected from compounds decreasing the strength of interaction between the receptor and the receptor ligand or from compounds increasing the strength of the interaction.

After the selection the candidate compound is according to the invention to be tested in an in vivo or in an in vitro cell system to evaluate significance of the recorded modulation for cellular metabolism. In such a system it may in one embodiment be measured a cell-surface receptor associated downstream signaling event, for example activation of a downstream protein. If the protein involved in interaction with a cell-surface receptor is represented by a receptor-like molecule, it may in another embodiment be measured a downstream signaling event associated with said protein. Therefore, the invention further provides a screening method for the compound selected on step (vii) of the above assay, comprising
viii) presenting the selected compound to at least one cell presenting the at least one functional cell-surface receptor molecule, or a fragment, or a variant thereof, and the at least one polypeptide having a binding site to said receptor, wherein at least a part of said binding site comprises at least one of the sequences set forth in SEQ ID NOS: 1-146, or fragments, or variants, or homologues of said sequences, or a fragments or a variants of said homologues with the compound of step (vii) of the above assay, ix) assessing at least one effect of the compound on the cell of step (viii).

The invention preferably concerns an FGFR1-associated downstream signaling event, which may be selected from estimation of i) the FGFR1 tyrosine phosphorylation; ii) the activation of one or more intracellular proteins involved in any of the FGFR-associated signal transduction pathways, such as for example the STAT1, JNK, PLCγ, ERK, STAT5, PI3K, PKC, FRS2 and/or GRB2 proteins; and/or iii) a cell differentiation-related effect.

When the FGFR signalling is measured as a level of phosphorylation of FGFR, the degree of phoshorylation is estimated as at least 20% above the control value, such as at least 20-200%, for example at least 50-200%. The control value in the present content is meant the degree of phosphorylation of FGFR in the medium where a compound capable of activation of FGFR is absent.

When estimating an efficient concentration of a compound with respect to modulating of the FGFR signalling, said concentration may be between 0.1-1000 µM, 1-1000 µM, for example 1-200 µM, for example 10-200 µM, such as 20-180 µM, for example 30-160 µM, such as 40-140 µM, for example 50-130 µM, such as 60-120 µM, for example 70-110 µM, such as 80-100 µM.

When estimating the downstream FGFR signaling effect such as a cell differentiation-related effect the invention preferably relates to cell aggregation, the formation of nodules, formation of cartilage, or two or more of said effects (Listrum, G. P. et al. J. Histochem. Cytochem. 1999, 47:1-6), such effect being detectable by light microscopy, turbidimetry, or flow cytometry. The cell differentiation-related effect may also be measured as a change in expression at RNA or protein levels of bone sialoprotein (J. Bone Miner. Res. 1998, 13:1852-61; Genomics 1998, 53: 391-4), or type X collagen (Cell Tissue Res. 1998, 293: 357-64), the human ILA gene (Osteoarthritis Gartilage 1997, 5: 394-406), or type II collagen/or MGP (J Miner Res. 1997: 1815.23), and the like.

The FGFR tyrosine phosphorylation or activation of any of the molecules of FGFR-associated downstream signaling, such as for example STST1, JNK, PLCγ, ERK, STAT5, PI3K, PKC, FRS2 and/or GRB2 proteins, may be estimated by any conventional methods, such as for example immunocytochemistry, immunoblotting or immunoprecipitation, using commercially available antibody against the activated proteins. The degree of activation is estimated as at least 20% above/below the control value, such as at least 20-200%, for example at least 50-200%. The control value is estimated as a degree of phosphorylation of the protein of interest in the medium where a compound capable of activation of FGFR is absent.

In another preferred embodiment the invention concerns the downstream signaling associated with a protein involved in interaction with FGFR, said protein being the FGFR1 ligand. Such downstream signaling is understood to be associated with a receptor-like ligand FGFR1. Preferred embodiments of such ligands of FGFR1 are disclosed above. It is understood that such ligands comprise the group of proteins, which have been associated with any downstream signal transduction cascade, or can potentially be associated with a downstream signal transduction cascade.

The most preferred a receptor-like ligand of FGFR1 of the invention is NCAM.

Therefore, the assay further concerns any in vitro or in vivo cellular systems comprising at least one cell presenting at least one molecule of functional FGFR1 or a functional homologue thereof and at least one molecule of NCAM or a functional homologue thereof.

NCAM-dependent signal transduction involves the variety of downstream molecules, activation of which upon the signaling may be measured. The invention in particular concerns the assessment of activation of focal adhesion kinase FAK, tyrosine kinase Fyn and/or cyclic-AMP response-binding element protein CREB. The degree of phoshorylation is estimated as at least 20% above/below the control value, such as at least 20-200%, for example at least 50-200%. The control value is estimated as above.

Activation or inhibition of NCAM-dependent signal transduction may also be measured by evaluating the cellular responses on morphological level, in particular cell differentiation-related effects. Accordingly, the assay concerns in another particular embodiment evaluation of the effect of a candidate compound on NCAM-dependent cellular aggregation, cell motility, neuritogenesis, proliferation or survival.

A skilled artisan may select from a number of assays have developed in the art to evaluate the above cellular responses. Cellular aggregation and neuritogenesis may for example be evaluated as described by Skladchikova et al. J. Neurosci. Res 1999, 57: 207-18. Proliferation and apoptosis may be evaluated by using any commercially available assays and kits according to the manufacturer procedure.

It is a preferred embodiment of the invention selecting a compound capable of modulating NCAM-FGFR1 interaction by evaluating the effect of the compound on neuritogenesis. Therefore, cells of neural origin, which are capable of neuronal differentiation, are preferred by the invention. Such cell may be selected from primary cells, which have been extracted from selected areas of the neural system of an organism and maintained in culture according to standard methods, or the cells may be clonal cells, which have been transformed to immortality from different neural tumor or embryonic neural cells. Examples of such cells can be rat pheochromocytoma PC 12, mouse neuroblastoma N2A, human teratocarcinoma NT-2 or mouse carcinoma F9.

In the present invention a compound is considered promising when it is capable of doubling the neurite outgrowth of cultured cells when compared to control cells, such as improving neurite outgrowth three-fold, such as four-fold, for example five fold, such as six-fold.

Further, the present assay in another preferred embodiment concerns the selection of a compound, which is capable of stimulating/promoting survival of cells by modulating the FGFR1-NCAM interaction. In the present context the wording "stimulating/promoting survival" is used synonymously with the wording "preventing cell death" or "neuro-protection". By stimulating/promoting survival it is possible to prevent diseases or prevent further degeneration of the nervous system in individuals suffering from a neuro-degenerative disorder. "Survival" refers to the process, wherein a cell has been traumatised and would under normal circumstances, with a high probability die, if not the compound of the invention was used to prevent said cell from degenerating, and thus promoting or stimulating survival of said traumatised cell. In particular the invention concerns promoting or stimulating the survival of cell of neural origin.

A cell culture of the assay may further comprise mammalian cells of non-neural origin. Examples of such cells may for example include HEK293, COS7, CHO or TREX293. These cells may desirably be transformed to express different variants or homologues of FGFR or NCAM by using the methods well known in art, such as for example methods of stable or transient transfection of cells with DNA constructs encoding different variants or homologues of FGFR and/or NCAM and/or other preferred ligands of FGFR of the invention. Such cells may be useful when using the evaluation of activation of the downstream molecules mentioned above for selection of a candidate compound.

Method for Molecular Design of a Candidate Compound

It is a further aspect of the invention to provide a method for molecular design for a compound capable of modulating the interaction between at least two different proteins, wherein one of the least two different proteins is represented by a functional cell-surface receptor, or a fragment, or a variant thereof, and another of the at least two different proteins is represented by a polypeptide having a binding site to said receptor, wherein at least a part of said binding site comprises at least one of the sequences set forth in SEQ ID NOS: 1-146, or fragments, or variants, or homologues of said sequences, or fragments or variants of said homologues comprising using structural data on the binding site of NCAM with FGFR.

Based on structural data on the binding site of NCAM with FGFR the invention provides a molecular model of interaction of FGFR1 and NCAM. The structural data provided by the invention disclose an amino acid sequence motif and a particular structural motif involved in the interaction these two molecules.

Accordingly, the peptide fragments
i) encompassing a sequence of at least 6 to 16 contiguous amino acids and
ii) having at least 60%, more preferably at least 70%, more preferably at least 80%, more preferably at least 90%, more preferably 95% sequence homology to the SEQ ID NO: 1 and or
iii) peptide fragments having the three-dimensional characteristics, such as for example strand-loop-strand fold, similar to the structural characteristics of the peptide fragment corresponding to SEQ ID NO: 1, wherein the sequences homology between the aligned peptide fragments is at least 40% and/or the positive amino acid match is at least 50%,
are considered by the invention as candidate compounds capable of modulation of interaction between FGFR and NCAM. Furthermore, a peptide fragment having at least 60%, more preferably at least 70%, more preferably at least 80%, more preferably at least 90%, more preferably 95% sequence homology to any of the sequences identified in SEQ ID NOS: 2-146 is considered by the invention as a potential candidate compound and designated by the invention for the screening in the screening assay for a capability of modulation of interaction between FGFR and a protein having the described above FGFR binding site.

Method for Identifying a Candidate Compound

According to the above described methods for screening and molecular design the candidate compound capable of modulating the interaction between at least two different proteins, wherein one of the least two different proteins is represented by a functional cell-surface receptor, or a fragment, or a variant thereof, and the other of the at least two different proteins is represented by a polypeptide having a binding site to said receptor, wherein at least a part of said binding site comprises at least one of the sequences set forth in SEQ ID NOS: 1-146, or fragments, or variants, or homologues of said sequences, or fragments or variants of said homologues can be isolated and used for the formulation of a pharmaceutical composition.

Thus, the invention provides
a method for isolating a candidate compound capable of modulating the interaction between at least two different proteins, wherein one of the least two different proteins is represented by a functional cell-surface receptor, or a fragment, or a variant thereof, and the other of the at least two different proteins is represented by a polypeptide having a binding site to said receptor, wherein at least a part of said binding site comprises at least one of the sequences set forth in SEQ ID NOS: 1-146, or fragments, or variants, or homologues of said sequences, or fragments or variants of said homologues, comprising the steps of
i) providing a method for sequential screening the candidate compound as the defined above and/or
ii) providing a method for molecular design of the candidate compound as the defined above,
iii) isolating the candidate compound;
a method for producing a pharmaceutical composition comprising the steps of identifying of a candidate compound and further the step of formulating of the compound capable of modulating the interaction between a cell surface receptor, or a fragment or variant thereof, and a polypeptide having a binding site to said receptor, wherein at least a part of said binding site comprises at least one of the sequences set forth in SEQ ID NOS: 1-146, or fragments, or variants, or homologues of said sequences, or fragments or variants of said homologues with pharmaceutically acceptable carrier or solvent.

Peptide Fragments

Using the described above method(s) and/or assay of the invention the peptide fragments which are capable of modulating the interaction between FGFR and a protein having the described above FGFR binding site may be identified. According the invention these peptide fragments in one embodiment are having at most about 100 amino acids comprising at least one of the amino acid sequences which are numbered from 2 to 146 and disclosed in the following sequence list:

| | |
|---|---|
| NIEVWVEAENALGKKV, | (SEQ ID NO: 2) |
| ATNRQGKVKAFAHL, | (SEQ ID NO: 3) |
| RYVELYVVADSQEFQK, | (SEQ ID NO: 4) |
| VAENSRGKNVAKG, | (SEQ ID NO: 5) |
| GEYWCVAENQYGQR, | (SEQ ID NO: 6) |
| RLAALNGKGLGEIS, | (SEQ ID NO: 7) |
| KYIAENMKAQNVAKEI, | (SEQ ID NO: 8) |
| TIMGLKPETRYAVR, | (SEQ ID NO: 9) |
| KGLGEISAATEFKT, | (SEQ ID NO: 10) |
| NMGIWVQAENALG, | (SEQ ID NO: 11) |
| IWVQAENMLG, | (SEQ ID NO: 12) |
| EIWVEATNRLG, | (SEQ ID NO: 13) |
| VWVQAANALG, | (SEQ ID NO: 14) |
| EVWIEKDPAKGRI, | (SEQ ID NO: 15) |
| ATNKGGEVKKNGHL, | (SEQ ID NO: 16) |
| KYVELYLVADYLEFQK, | (SEQ ID NO: 17) |
| RYVELYVVVDNAEFQ, | (SEQ ID NO: 18) |
| KYVELVIVADNREFQR, | (SEQ ID NO: 19) |

```
-continued
KYIEYYLVLDNGEFKR,      (SEQ ID NO: 20)
RYLELYIVADHTLF,        (SEQ ID NO: 21)
KYVEMFVVVNHQRFQ,       (SEQ ID NO: 22)
RYVELFIVVDKERY,        (SEQ ID NO: 23)
KYVELFIVADDTVYRR,      (SEQ ID NO: 24)
KFIELFVVADEYVYRR,      (SEQ ID NO: 25)
KIVEKVIVADNSEVRK,      (SEQ ID NO: 26)
VELVIVADHSEAQK,        (SEQ ID NO: 27)
VAENSRGKNIAKG,         (SEQ ID NO: 28)
IAENSRGKNVARG,         (SEQ ID NO: 29)
AENSRGKNSFRG,          (SEQ ID NO: 30)
IASNLRGRNLAKG,         (SEQ ID NO: 31)
IPENSLGKTYAKG,         (SEQ ID NO: 32)
IAENMKAQNEAK,          (SEQ ID NO: 33)
QFIAENMKSHNETKEV,      (SEQ ID NO: 34)
GEYWCVAKNRVGQ,         (SEQ ID NO: 35)
GSYTCVAENMVGK,         (SEQ ID NO: 36)
GKYVCVGTNMVGER,        (SEQ ID NO: 37)
GNYTCVVENEYG,          (SEQ ID NO: 38)
GEYTCLAGNSIG,          (SEQ ID NO: 39)
QYYCVAENGYG,           (SEQ ID NO: 40)
GEYYQEAEQNGYG,         (SEQ ID NO: 41)
GNYTCLVENEYG,          (SEQ ID NO: 42)
GMYQCLAENAYG,          (SEQ ID NO: 43)
GMYQCAENTHG,           (SEQ ID NO: 44)
GIYYCLASNNYG,          (SEQ ID NO: 45)
GGYYCTADNSYG,          (SEQ ID NO: 46)
GEYQCFARNDYG,          (SEQ ID NO: 47)
GEYFCLASNKMG,          (SEQ ID NO: 48)
GEYQCFARNKFG,          (SEQ ID NO: 49)
GEYFCLASNKMG,          (SEQ ID NO: 50)
GGYYCTADNNYG,          (SEQ ID NO: 51)
GNYSCEAENAWGTK,        (SEQ ID NO: 52)
GEYTCLAENSLG,          (SEQ ID NO: 53)
GEYECVAENGRLG,         (SEQ ID NO: 54)
GNYTCVVENKFGR,         (SEQ ID NO: 55)
GEYTCLAGNSIG,          (SEQ ID NO; 56)
GEYFCVASNPIG,          (SEQ ID NO: 57)
EYTCIANNQAGE,          (SEQ ID NO: 58)
GMYQCVAENKHLG,         (SEQ ID NO: 59)
GEYMCTASNTIGQ,         (SEQ ID NO: 60)

-continued
EYVCIAENKAGEQ,         (SEQ ID NO: 61)
GDYTLIAKNEYGK,         (SEQ ID NO: 62)
GFYQCVAENEAG,          (SEQ ID NO: 63)
GKYECVATNSAGTR,        (SEQ ID NO: 64)
GEYFCVYNNSLG,          (SEQ ID NO: 65)
GEYECAATNAHGR,         (SEQ ID NO: 66)
GAYWCQGTNSVGK,         (SEQ ID NO: 67)
GTYSCVAENILG,          (SEQ ID NO: 68)
RVAAVNGKQGDYS,         (SEQ ID NO: 69)
RVAAINGCGIGPFS,        (SEQ ID NO: 70)
AVLNGKGLG,             (SEQ ID NO: 71)
ALNGQGLGATS,           (SEQ ID NO: 72)
RLAAKNRAGLGE,          (SEQ ID NO: 73)
RLGVVTGKDLGEI,         (SEQ ID NO: 74)
TVTGLKPETSYMVK,        (SEQ ID NO: 75)
TLTGLKPSTRYRI,         (SEQ ID NO: 76)
TLTGLQPSTRYRV,         (SEQ ID NO: 77)
TLLGLKPDTTYDIK,        (SEQ ID NO: 78)
TLQGLRPETAYELR,        (SEQ ID NO: 79)
TLRGLRPETAYELR,        (SEQ ID NO: 80)
TLMNLRPKTGYSVR,        (SEQ ID NO: 81)
TVSGLKPGTRY,           (SEQ ID NO: 82)
TISGLKPDTTY,           (SEQ ID NO: 83)
TLQGLKPDTAY,           (SEQ ID NO: 84)
LRGLKPWTQYAV,          (SEQ ID NO: 85)
IDGLEPDTEYIVR,         (SEQ ID NO: 86)
LQGLKPWTQYAI,          (SEQ ID NO: 87)
TITGLEPGTEYTIQ,        (SEQ ID NO: 88)
GLKPWTQYAV,            (SEQ ID NO: 89)
TLASLKPWTQYAV,         (SEQ ID NO: 90)
LMGLQPATEYIV,          (SEQ ID NO: 91)
KGMGPMSEAVQFRT,        (SEQ ID NO: 92)
TLTGLKPDTTYDVK,        (SEQ ID NO: 93)
ISGLQPETSYSL,          (SEQ ID NO: 94)
TLLGLKPDTTYDIK,        (SEQ ID NO: 95)
TISGLTPETTYSI,         (SEQ ID NO: 96)
GNYSCLAENRLGR,         (SEQ ID NO: 97)
GNYTCVVENRVG,          (SEQ ID NO: 98)
GTYHCVATNAHG,          (SEQ ID NO: 99)
LSHNGVLTGYLLSY,        (SEQ ID NO: 100)
```

-continued

| | |
|---|---|
| NGVLTGYVLRY, | (SEQ ID NO: 101) |
| NGVLTGYNLRY, | (SEQ ID NO: 102) |
| NGNLTGYLLQY, | (SEQ ID NO: 103) |
| VDENGVLTGYKIYY, | (SEQ ID NO: 104) |
| THNGALVGYSVRY, | (SEQ ID NO: 105) |
| NGILTEYILKY, | (SEQ ID NO: 106) |
| NGILIGYTLRY, | (SEQ ID NO: 107) |
| THSGQITGYKIRY, | (SEQ ID NO: 108) |
| NGKITGYIIYY, | (SEQ ID NO: 109) |
| LSHNGIFTLY, | (SEQ ID NO: 110) |
| NGILTEYTLKY, | (SEQ ID NO: 111) |
| LDPNGIITQYEISY, | (SEQ ID NO: 112) |
| NGKITGYIIYY, | (SEQ ID NO: 113) |
| HLEVQAFNGRGSGPA, | (SEQ ID NO: 114) |
| HLTVRAYNGAGYGP, | (SEQ ID NO: 115) |
| HLSVKAYNSAGTGPS, | (SEQ ID NO: 116) |
| HLAVKAYNSAGTGPS, | (SEQ ID NO: 117) |
| NLEVRAFNSAGDGP, | (SEQ ID NO: 118) |
| HLTVLAYNSKGAGP, | (SEQ ID NO: 119) |
| LRVLVFNGRGDGP, | (SEQ ID NO: 120) |
| HIDVSAFNSAGYGP, | (SEQ ID NO: 121) |
| HLAVELFNGR, | (SEQ ID NO: 122) |
| LELQSINFLGGQPA, | (SEQ ID NO: 123) |
| HFTVRAYNGAGYGP, | (SEQ ID NO: 124) |
| HLEVQAFNGRGSQPA, | (SEQ ID NO: 125) |
| VIADQPTFVKYLIK, | (SEQ ID NO: 126) |
| TIKGLRPGVVYEGQ, | (SEQ ID NO: 127) |
| TLTELSPSTQYTVK, | (SEQ ID NO: 128) |
| TLDDLAPDTTYLVQ, | (SEQ ID NO: 129) |
| TVSDVTPHAIYTVR, | (SEQ ID NO: 130) |
| IIRGLNASTRYLFR, | (SEQ ID NO: 131) |
| TLMNLRPKTGYSVR, | (SEQ ID NO: 132) |
| TLTGLKPGTEYEVR, | (SEQ ID NO: 133) |
| GPEHLMPSSTYVAR, | (SEQ ID NO: 134) |
| RVTGLTPKKTYEFR, | (SEQ ID NO: 135) |
| LTGLKPGTEYEFR, | (SEQ ID NO: 136) |
| EVRVQAVNGGGNGPP, | (SEQ ID NO: 137) |
| LIKVVAINDRGE, | (SEQ ID NO: 138) |
| VVSIIAVNGREE, | (SEQ ID NO: 139) |
| VVSVYAQNQNGE, | (SEQ ID NO: 140) |

-continued

| | |
|---|---|
| TISLVAEKGRHK, | (SEQ ID NO: 141) |
| HLEVQAFNGRGSGPA, | (SEQ ID NO: 142) |
| HVEVQAFNGRGLGPA, | (SEQ ID NO: 143) |
| HVEVQAFNGRGLGPA, | (SEQ ID NO: 144) |
| EFRVRAVNGAGEG, | (SEQ ID NO: 145) |
| VARVRTRLAPGSRLS | (SEQ ID NO: 146) | or a variant or a fragment, or a homologue thereof.

According to the invention a peptide compound in one embodiment comprises at least one of the above sequences. In another embodiment, the compound is essentially comprising at least one of the above sequences. In still another embodiment, the compound is consisting of at least one of the above sequences.

The fragments, variants and homologues of the above sequences are defined according to the criteria for fragments, variants and homologues of a peptide compound described above.

It is an objective of the present invention to provide one or more the above amino acid sequences for the manufacture of a medicament.

Another objective of the invention is to use the above sequences as antigenic epitopes for the production of antibodies.

Antibodies

It an objective of the present invention to provide an antibody capable of selectively binding to an epitope comprising the binding site of the invention. Therefore, the invention relates to any antibody capable of selectively binding to an epitope comprising 1) any of the sequences set forth in SEQ ID NOS: 1-10, 100, 125, or fragments or variants, or homologues said sequences, or fragments or variants of said homologues, wherein i) a fragment is defined as an amino acid sequence having at least 40%, more preferably at least 50%, more preferably at least 60%, more preferably at least 70%, more preferably at least 80%, more preferably at least 90%, more preferably at least 95% of the length of a predetermined sequence set forth in SEQ ID NOS: 1-10, 100, 125, wherein an amino acid sequence homology between a fragment and the predetermined sequence is 100%, ii) a variant is defined as an amino acid sequence having at least 60%, more preferably at least 70%, more preferably at least 80%, more preferably at least 90%, more preferably 95% homology to a sequence selected from SEQ ID NOS: 1-10, 100, 125 or an amino acid sequence having at least 60%, more preferably at least 70%, more preferably at least 80%, more preferably at least 90%, more preferably 95% positive amino acid matches compared to a sequence selected from SEQ ID NOS: 1-10, 100, 125, wherein a positive amino acid match is defined as an identity or similarity defined by physical and/or chemical properties of the amino acids having the same position in two compared sequences. Preferred positive amino acid matches of the present invention are K to R, E to D, L to M, Q to E, I to V, I to L, A to S, Y to W, K to Q, S to T, N to S and Q to R. The homology of one amino acid sequence with another amino acid is defined as a percentage of identical amino acids in the two collated sequences, iii) a homologue is defined as an amino acid sequence which has less then 60% and more then 19%, such as 50-59%, for example 55%, such as 40-49%, for example 45%, such as 30-39%, for example 35%, such as 20-29%, for example 25% homology to any of the sequences set forth in SEQ ID NOS: 1-10, 100, 125 having remained some of the physical properties of the predetermined sequences, such as for example the three-dimensional structure or some of the functional properties, such as for example a capability to interact with another molecule, particularly with a receptor molecule, iv) a variant of a homologue is defined as an amino acid sequence having at least 60%, more preferably at least 70%, more preferably at least 80%, more preferably at least 90%, more preferably 95% positive amino acid matches compared to a homologue of any of the sequences selected from SEQ ID NO: 1-10, 100, 125 wherein the positive amino acid matches being as the defined above;

and/or 2) any of the sequences identified as SEQ ID NOS: 11-99, 101-124, 126-146 or fragments or variants, or homologues said sequences, or fragments or variants of said homologues, wherein said fragments or variants, or homologues said sequences, or fragments or variants of said homologues being defined as the above, and/or 3) a peptide fragment having structural characteristics, such as for example strand-loop-strand fold, similar to the structural characteristics of a peptide fragment corresponding to SEQ ID NO: 1, wherein the sequences homology between the aligned peptide fragments is at least 40% and/or the positive amino acid match is at least 50%.

In one embodiment the antibody is capable to modulate the cell-surface receptor function by decreasing or increasing the capability of a ligand to activate the receptor by modulating the binding of said ligand to said receptor. By "modulating binding" in the present context is meant a capability of an antibody to increase/decrease the affinity and/or strength of ligand-receptor interaction. In a more preferred embodiment the antibody is capable to bind to the described above epitope in a FGFR ligand and thereby to modulate activating of FGFR. By "modulate" in the present context is meant to promote or inhibit the activating of the receptor. Preferred embodiments for these FGFR ligands are described above.

In another embodiment the antibody is capable to modulate the biological function of a cell-surface receptor ligand by interfering with the binding of said ligand to said receptor. This embodiment relates to those FGFR ligands that (i) may be the receptor molecules independent from FGFR, and/or (ii) may use an alternative receptor when the FGFR signaling is inhibited, and/or (iii) may have additional biological functions that are not associated with any downstream signaling.

Preferred embodiments for such ligands comprising the epitope of the invention are described above.

Fragments of the polypeptides comprising the binding site of the invention can be used to raise antibodies useful in the invention. It is preferred to use for raising the above described antibodies the peptide fragments having the sequences set forth in SEQ ID NOS: 1-146, or fragments or variants, or homologues said sequences, or fragments or variants of said homologues. In general, the peptides can be coupled to a carrier protein, such as KLH, as described in Ausubel et al., supra, mixed with an adjuvant, and injected into a host mammal. Such polypeptides or peptide fragments can be produced by recombinant techniques as described the above or synthesized (see, for example, "Solid Phase Peptide Synthesis," supra; Ausubel et al., supra). Also the carrier could be PPD. Antibodies can be purified by peptide antigen affinity chromatography.

Thus, the invention concerns a method for the production of antibodies comprising administering to an animal a peptide fragment comprising at least one sequence selected from the sequences set forth in SEQ ID NOS: 1-146.

In particular, various host animals can be immunized by injection with the above peptide fragments. Host animals include rabbits, mice, guinea pigs, rats, and chickens. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Potentially useful human adjuvants include BCG (bacille Calmette-Guerin) and *Corynebacterium parvum*. Immunizations may also be carried out by the injection of DNA encoding an FGFR-ligand or fragments thereof corresponding to the binding site. Polyclonal antibodies are heterogeneous populations of antibody molecules that are contained in the sera of the immunized animals.

Antibodies within the invention therefore include polyclonal antibodies and, in addition, monoclonal antibodies, humanized or chimeric antibodies, single chain antibodies, Fab' fragments, F(ab')$_2$ fragments, and molecules produced using a Fab expression library, and antibodies or fragments produced by phage display techniques.

Monoclonal antibodies, which are homogeneous populations of antibodies to a particular antigen, can be prepared using the peptide fragments comprising the above described binding site and standard hybridoma technology (see, for example, Kohler et al., *Nature* 256:495, 1975; Kohler et al., *Eur. J. Immunol.* 6:511, 1976; Kohler et al., *Eur. J. Immunol.* 6:292, 1976; Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al., *Nature* 256:495, 1975, and U.S. Pat. No. 4,376,110; the human B-cell hybridoma technique (Kosbor et al., *Immunology Today* 4:72, 1983; Cole et al., *Proc. Natl. Acad. Sci. USA* 80:2026, 1983), and the EBV-hybridoma technique (Cole et al., "Monoclonal Antibodies and Cancer Therapy," Alan R. Liss, Inc., pp. 77-96, 1983). Such antibodies can be of any immunoglobulin class including IgG, IgM, IgE, IgA, IgD and any subclass thereof. (In the case of chickens, the immunoglobulin class can also be IgY.) The hybridoma producing the mAb of this invention may be cultivated in vitro or in vivo. The ability to produce high titers of mAbs in vivo makes this the presently preferred method of production, but in some cases, in vitro production will be preferred to avoid introducing cancer cells into live animals, for example, in cases where the presence of normal immunoglobulins coming from the acitis fluids are unwanted, or in cases involving ethical considerations.

Once produced, polyclonal, monoclonal, or phage-derived antibodies are tested for specific recognition of the above described epitope by Western blot or immunoprecipitation in samples containing the polypeptides comprising the binding site or fragments thereof, e.g., as described in Ausubel et al., supra. Antibodies that specifically recognise and bind to a FGFR ligand are useful in the invention. For example, such antibodies can be used in an immunoassay to monitor the level of expression a FGFR ligand in a sample collected from an individual.

In some cases it may be desirable to minimize the potential problems of low affinity or specificity of antisera. In such circumstances, two or three fusions can be generated for each protein, and each fusion can be injected into at least two animals. Antisera can be raised by injections in a series, preferably including at least three booster injections. Spleen cells from the immunised animals may be used for generating monoclonal antibodies.

An antibody capable of binding to an epitope as defined above may be used for determining a substance comprising an epitope comprising at least one of the sequences set forth in SEQ ID NOS: 1-146, or fragments, or variants, or homologues of said sequences, or fragments or variants of said homologues in a sample. The sample may be any sample comprising the substance, for example a solution of the substance or a biological sample. The substance comprising an epitope may be of natural or synthetic origin. The examples of such a substance include, but not limited a cell comprising a compound comprising an epitope, a compound comprising an epitope, a compound consisting of an epitope. The cell comprising a compound comprising an epitope may be for example a cell expressing a ligand of a cell surface receptor of the invention. Examples of such ligands are described above. The compound comprising the epitope may be any compound described above.

The above antibodies may for example be used in the detection of an FGFR ligand in a biological sample. The antibody may also be used in a screening assay for measuring the activity of FGFR, for example as a part of a diagnostic assay. Depending on the detection technique the antibody may be coupled to a compound comprising a detectable marker. The markers or labels may be selected from any markers and labels known in the art. The antibody may also be used for determining the concentration of a substance comprising an epitope or epitope in a solution of said substance or said epitope. A wide spectrum of detection and labelling techniques is available now in the art and the techniques may therefore be selected depending on skills of the artisan practising the antibodies or on the purpose of using thereof.

In addition, techniques developed for the production of "chimeric antibodies" (Morrison et al., *Proc. Natl. Acad. Sci. USA,* 81:6851, 1984; Neuberger et al., *Nature,* 312:604, 1984; Takeda et al., *Nature,* 314.452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778, 4,946,778, and 4,704,692) can be adapted to produce single chain antibodies against an FGFR-ligand or a fragment thereof. Single chain antibodies are formed by linking the heavy and light chain fragments of the Fv region via an amino acid bridge, resulting in a single chain polypeptide.

Antibody fragments that recognise and bind to specific epitopes can be generated by known techniques. For example, such fragments include but are not limited to $F(ab')_2$ fragments that can be produced by pepsin digestion of the antibody molecule, and Fab' fragments that can be generated by reducing the disulfide bridges of $F(ab')_2$ fragments. Alternatively, Fab' expression libraries can be constructed (Huse et al., *Science,* 246:1275, 1989) to allow rapid and easy identification of monoclonal Fab' fragments with the desired specificity.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., Nature Genetics 7:13-21, 1994; see also U.S. Pat. Nos. 5,545,806 and 5,569,825, both of which are hereby incorporated by reference).

Production of Polypeptides and Peptide Fragments

Polypeptides and peptide fragments of the invention can be provided by any suitable conventional method known in the art. The peptide fragments and polypeptides of the invention can be for example chemically synthesized (for example, see Creighton, "Proteins: Structures and Molecular Principles," W.H. Freeman & Co., NY, 1983), or, perhaps more advantageously, produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 1984).

Recombinant Molecules

The methods and the assay described above all include a step of providing at least two interacting proteins.

The two interacting proteins of the methods and the assay of the invention are preferably recombinant proteins. Therefore, the invention in additional embodiment encompasses expression vectors that contain the coding DNA sequences for the interacting proteins and genetically engineered host cells that contain any of the foregoing expression vectors and thereby express the nucleic acid molecules of the invention in the host cell.

Preferred embodiments for the expression vectors are: (a) expression vectors that contain any of the foregoing FGFRs, including FGFR1, FGFR2, FGFR3 and FGFR4, or FGFR-ligand related coding sequences, said FGFR-ligand being selected from the preferred polypeptides of the invention described above, and/or their complements (that is, "antisense" sequence); (b) expression vectors that contain any of the foregoing FGFRs or FGFR-ligand related coding sequences comprising the above mutation operatively associated with a regulatory element (examples of which are given below) that directs the expression of the coding sequences; (c) expression vectors containing, in addition to sequences encoding mutated FGFRs or FGFR-ligands, nucleic acid sequences that are unrelated to nucleic acid sequences encoding the FGFRs or FGFR-ligands, such as molecules encoding a reporter or marker.

Recombinant nucleic acid molecule may contain a sequence encoding mutated FGFRs or FGFR-ligands, soluble FGFRs or FGFR-ligands, truncated FGFRs or FGFR-ligands, or functional domains of FGFRs, such as for example Ig 2 or Ig 3 domain of FGFR1, or the domains of a FGFR ligand, such as for example the domains of NCAM, for example the Ig-like or F3 type domains. The full-length mutated polypeptides, domains of FGFRs or FGFR-ligands, or fragments thereof may be fused to additional polypeptides, as described below.

The regulatory elements referred to above include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast-mating factors.

Similarly, the nucleic acid can form part of a hybrid gene encoding additional polypeptide sequences, for example, sequences that function as a marker or reporter. Examples of marker or reporter genes include—lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding-galactosidase), green fluorescent protein (GFP), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter. Generally, the hybrid polypeptide will include a first portion and a second portion; the first portion being, for example, a portion of the FGFR1 or NCAM amino acid sequence and the second portion being, for example, the reporter described above or an immunoglobulin heavy chain.

The expression systems that may be used for purposes of the invention include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, *Saccharomyces* and *Pichia*) transformed with recombinant yeast expression vectors containing the nucleic acid molecules encoding FGFR1 or the nucleic acid sequence encoding NCAM; insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing FGFR nucleotide sequences; or mammalian cell systems (for example, COS, CHO, BHK, 293, VERO, HeLa, MDCK, WI38, and NIH 3T3 cells) harbouring recombinant expression constructs containing promoters derived from the genome of mammalian cells (for example, the metallothionein promoter) or from mammalian viruses (for example, the adenovirus late promoter and the vaccinia virus 7.5K promoter).

In bacterial systems, a number of expression vectors may be advantageously selected depending upon the use intended for the gene product being expressed. Such vectors include, but are not limited to, the *E. coli* expression vector pUR278 (Ruther et al., *EMBO J.* 2:1791, 1983), in which the coding sequence of the insert may be ligated individually into the vector in frame with the lacZ coding region so that a fusion protein is produced; pIN vectors (Inouye and Inouye, *Nucleic Acids Res.* 13:3101-3109, 1985; Van Heeke and Schuster, *J. Biol. Chem.* 264:5503-5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) can be used as a vector to express foreign genes. The virus grows in *Spodoptera frugiperda* cells. The coding sequence of the insert may be cloned individually into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (for example, see Smith et al., *J. Virol.* 46:584, 1983; Smith, U.S. Pat. No. 4,215,051).

In mammalian host cells, a number of viral-based expression systems may be utilized. In cases where an adenovirus is used as an expression vector, the nucleic acid molecule of the invention may be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (for example, region E1 or E3) will result in a recombinant virus that is viable and capable of expressing a FGFR gene product in infected hosts (for example, see Logan and Shenk, *Proc. Natl. Acad. Sci. USA* 81:3655-3659, 1984). Specific initiation signals may also be required for efficient translation of inserted nucleic acid molecules. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol* 153:516-544, 1987).

In addition, a host cell strain may be chosen, which modulates the expression of the inserted sequences, or modifies and processes the gene product in the specific fashion desired. Such modifications (for example, glycosylation) and processing (for example, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. The mammalian cell types listed above are among those that could serve as suitable host cells.

For long-term, high-yield production of recombinant proteins, stable expression is preferred. For example, cell lines, which stably express the FGFR sequences or any FGFR ligand sequences described above may be engineered. Rather than using expression vectors which contain viral origins of replication, host cells can be transformed with DNA controlled by appropriate expression control elements (for example, promoter, enhancer sequences, transcription terminators, polyadenylation sites, etc.), and a selectable marker. Following the introduction of the foreign DNA, engineered cells may be allowed to grow for 1-2 days in an enriched media, and then switched to a selective media. The selectable marker in the recombinant plasmid confers resistance to the selection and allows cells to stably integrate the plasmid into their chromosomes and grow to form foci which in turn can be cloned and expanded into cell lines. Such engineered cell lines may be particularly useful in the screening assay and evaluation of candidate compounds that affect the interaction between FGFR and an FGFR ligand.

A number of selection systems can be used. For example, the herpes simplex virus thymidine kinase (Wigler, et al., *Cell* 11: 223, 1977), hypoxanthine-guanine phosphoribosyltransferase (Szybalska and Szybalski, *Proc. Natl. Acad. Sci. USA* 48:2026, 1962), and adenine phosphoribosyltransferase (Lowy, et al., *Cell* 22:817, 1980) genes can be employed in tk⁻, hgprt⁻ or aprt⁻ cells, respectively. Also, anti-metabolite resistance can be used as the basis of selection for the following genes: dhfr, which confers resistance to methotrexate (Wigler et al., *Proc. Natl. Aced. Sci. USA* 77:3567, 1980; O'Hare et al., *Proc. Natl. Acad. Sci. USA* 78:1527, 1981); gpt, which confers resistance to mycophenolic acid (Mulligan and Berg, *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1984).

Alternatively, any fusion protein may be readily purified by utilizing an antibody specific for the fusion protein being expressed. For example, a system described by Janknecht et al. allows for the ready purification of non-denatured fusion proteins expressed in human cell lines (*Proc. Natl. Acad. Sci. USA* 88: 8972-8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

It is presumed that molecules of one group of the recombinant proteins of the invention comprise the described above binding site, and molecules of another group of the recombinant proteins comprise a site for recognition of said binding site.

Medicament

Activation of cell-surface receptors upon the ligand binding is strictly regulated in a healthy organism. Mutations, abnormal expression or processing of a receptor or the receptor ligands lead to abnormalities in activity of the receptor and therefore lead to dysfunction of the receptor. The dysfunction of the receptor is in turn a reason for dysfunction of the cells which use the receptor for maintenance of various cellular processes. The latter is a manifestation of a disease. FGFRs are expressed by a wide variety of cell species during embryonic development and in the adult. Dysfunction of these receptors has been associated with a number of diseases.

Accordingly, it is an objective of the invention to provide a compound capable of modulation of the activity of FGFRs, said compound being concerned by the invention as a medicament for the treatment of diseases, wherein modulation of the activity of FGFRs may be considered as an essential condition for the curing.

Thus, the medicament of the invention is in one embodiment for the treatment of 1) normal, degenerated or damaged NCAM presenting cells, and/or
2) diseases and conditions of the central and peripheral nervous system, or of the muscles or of various organs, and/or
3) diseases or conditions of the central and peripheral nervous system, such as postoperative nerve damage, traumatic nerve damage, impaired myelination of nerve fibers, postischaemic damage, e.g. resulting from a stroke, Parkinson's disease, Alzheimer's disease, Huntington's disease, dementias such as multiinfarct dementia, sclerosis, nerve degeneration associated with diabetes mellitus, disorders affecting the circadian clock or neuro-muscular transmission, and schizophrenia, mood disorders, such as manic depression; for treatment of diseases or conditions of the muscles including conditions with impaired function of neuro-muscular connections, such as after organ transplantation, or such as genetic or traumatic atrophic muscle disorders; or for treatment of diseases or conditions of various organs, such as degenerative conditions of the gonads, of the pancreas such as diabetes mellitus type I and II, of the kidney such as nephrosis and of the heart, liver and bowel, and/or
4) postoperative nerve damage, traumatic nerve damage, impaired myelination of nerve fibers, postischaemic, e.g. resulting from a stroke, Parkinson's disease, Alzheimer's disease, Huntington's disease, dementias such as multiinfarct dementia, sclerosis, nerve degeneration associated with diabetes mellitus, disorders affecting the circadian clock or neuro-muscular transmission, and schizophrenia, mood disorders, such as manic depression, and/or
5) cancer disease, wherein the cancer is any type of solid tumors requiring neoangiogenesis.

In another embodiment the medicament of the invention is for the manufacture of a medicament for 1) promotion of wound-healing, and/or
2) prevention of cell death of heart muscle cells, such as after acute myocardial infarction, or after angiogenesis, and/or
3) revascularsation, and/or
4) stimulation of the ability to learn and/or of the short and/or long-term memory.

In one embodiment the medicament of the invention comprises at least one the amino acid sequences set forth in SEQ ID NOS: 2-146, or fragments or variants, or homologues said sequences, or fragments or variants of said homologues. In another embodiment the medicament of the invention comprises an antibody capable of binding to an epitope comprising the binding site of the invention, or a fragment, or a variant of said antibody.

The medicament of the invention comprises an effective amount of one or more of the compounds as defined above, or a composition as defined above in combination with pharmaceutically acceptable additives. Such medicament may suitably be formulated for oral, percutaneous, intramuscular, intravenous, intracranial, intrathecal, intracerebroventricular, intranasal or pulmonal administration.

Strategies in formulation development of medicaments and compositions based on the compounds of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules, nanoparticles or the like.

The preparation may suitably be administered by injection, optionally at the site, where the active ingredient is to exert its effect. Additional formulations which are suitable for other modes of administration include suppositories, nasal, pulmonal and, in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10-95% of the active ingredient(s), preferably 25-70%.

Other formulations are such suitable for nasal and pulmonal administration, e.g. inhalators and aerosols.

The active compound may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred μg active ingredient per administration with a preferred range of from about 0.1 μg to 5000 μg per kilo body weight. Using monomeric forms of the compounds, the suitable dosages are often in the range of from 0.1 μg to 5000 μg per kilo body weight, such as in the range of about 0.1 μg to 3000 μg per kilo body weight, and especially in the range of from about 0.1 μg to 1000 μg per kilo body weight. Using multimeric forms of the compounds, the suitable dosages are often in the range of from 0.1 μg to 1000 μg per kilo body weight, such as in the range of from about 0.1 μg to 750 μg per kilo body weight, and especially in the range of from about 0.1 μg to 500 μg per kilo body weight such as in the range of from about 0.1 μg to 250 μg per kilo body weight. In particular when administering nasally smaller dosages are used than when administering by other routes. Administration may be performed once or may be followed by subsequent administrations. The dosage will also depend on the route of administration and will vary with the age and weight of the subject to be treated. A preferred dosage of multimeric forms would be in the interval 1 mg to 70 mg per 70 kg body weight.

For most indications a localised or substantially localised application is preferred.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promote delivery of the active substance to its target.

In many instances, it will be necessary to administrate the formulation multiple times. Administration may be a continuous infusion, such as intraventricular infusion or administration in more doses such as more times a day, daily, more times a week, weekly, etc. It is preferred that administration of the medicament is initiated before or shortly after the individual has been subjected to the factor(s) that may lead to cell death. Preferably the medicament is administered within 8 hours from the factor onset, such as within 5 hours from the factor onset. Many of the compounds exhibit a long term effect whereby administration of the compounds may be conducted with long intervals, such as 1 week or 2 weeks.

In connection with the use in nerve guides, the administration may be continuous or in small portions based upon controlled release of the active compound(s). Furthermore, precursors may be used to control the rate of release and/or site of release. Other kinds of implants and well as oral administration may similarly be based upon controlled release and/or the use of precursors.

Treatment

Treatment by the use of the compounds/compositions according to the invention is in one embodiment useful for inducing differentiation, modulating proliferation, stimulate regeneration, neuronal plasticity and survival of cells being implanted or transplanted. This is particularly useful when using compounds having a long term effect.

In further embodiment the treatment may be for stimulation of survival of cells which are at risk of dying due to a variety of factors, such as traumas and injuries, acute diseases, chronic diseases and/or disorders, in particular degenerative diseases normally leading to cell death, other external factors, such as medical and/or surgical treatments and/or diagnostic methods that may cause formation of free radicals or otherwise have cytotoxic effects, such as X-rays and chemotherapy. In relation to chemotherapy the FGFR binding compounds according to the invention are useful in cancer treatment of all cancer cells presenting FGFRs.

Thus, the treatment comprises treatment and/or prophylaxis of cell death in relation to diseases or conditions of the central and peripheral nervous system, such as postoperative nerve damage, traumatic nerve damage, e.g. resulting from spinal cord injury, impaired myelination of nerve fibers, postischaemic damage, e.g. resulting from a stroke, multiinfarct dementia, multiple sclerosis, nerve degeneration associated with diabetes mellitus, neuro-muscular degeneration, schizophrenia, Alzheimer's disease, Parkinson's disease, or Huntington's disease.

Also, in relation to diseases or conditions of the muscles including conditions with impaired function of neuro-muscular connections, such as genetic or traumatic atrophic muscle disorders; or for the treatment of diseases or conditions of various organs, such as degenerative conditions of the gonads, of the pancreas, such as diabetes mellitus type I and II, of the kidney, such as nephrosis the compounds according to the invention may be used for inducing differentiation, modulating proliferation, stimulate regeneration, neuronal plasticity and survival, i.e. stimulating survival.

Furthermore, the compound and/or pharmaceutical composition may be for preventing cell death of heart muscle cells, such as after acute myocardial infarction, in order to induce angiogenesis. Furthermore, in one embodiment the compound and/or pharmaceutical composition is for the stimulation of the survival of heart muscle cells, such as survival after acute myocardial infarction. In another aspect the compound and/or pharmaceutical composition is for revascularisation, such as after injuries.

It is also within the scope of the invention to use the compound and/or pharmaceutical composition for the promotion of wound-healing. The present compounds are capable of stimulating angiogenesis and thereby promote the wound healing process.

The invention further discloses the use of the compound and/or pharmaceutical composition in the treatment of cancer. Regulation of activation of FGFR is important for tumor agiogenesis, proliferation and spreading.

In yet a further embodiment the use of the compound and/or pharmaceutical composition is for the stimulation of the ability to learn and/or of the short and/or long term memory, as FGFR activity is important for differentiation of neural cells.

In particular the compound and/or pharmaceutical composition of the invention may be used in the treatment of clinical conditions, such as Neoplasms such as malignant neoplasms, benign neoplasms, carcinoma in situ and neoplasms of uncertain behavior, diseases of endocrine glands, such as diabetes mellitus, psychoses, such as senile and presenile organic psychotic conditions, alcoholic psychoses, drug psychoses, transient organic psychotic conditions, Alzheimer's disease, cerebral lipidoses, epilepsy, general paresis [syphilis], hepatolenticular degeneration, Huntington's chorea, Jakob-Creutzfeldt disease, multiple sclerosis, Pick's disease of the brain, syphilis, Schizophrenic disorders, affective psychoses, neurotic disorders, personality disorders, including character neurosis, nonpsychotic personality disorder associated with organic brain syndromes, paranoid personality disorder, fanatic personality, paranoid personality (disorder), paranoid traits, sexual deviations and disorders, mental retardation, disease in the nervesystem and sense organs, cognitive anomalies, inflammatory disease of the central nervous system, such as meningitis, encephalitis, Cerebral degenerations such as Alzheimer's disease, Pick's disease, senile degeneration of brain, communicating hydrocephalus, obstructive hydrocephalus, Parkinson's disease including other extra pyramidal disease and abnormal movement disorders, spinocerebellar disease, cerebellar ataxia, Marie's, Sanger-Brown, Dyssynergia cerebellaris myoclonica, primary cerebellar degeneration, such as spinal muscular atrophy, familial, juvenile, adult spinal muscular atrophy, motor neuron disease, amyotrophic lateral sclerosis, motor neuron disease, progressive bulbar palsy, pseudobulbar palsy, primary lateral sclerosis, other anterior horn cell diseases, anterior horn cell disease, unspecified, other diseases of spinal cord, syringomyelia and syringobulbia, vascular myelopathies, acute infarction of spinal cord (embolic) (nonembolic), arterial thrombosis of spinal cord, edema of spinal cord, subacute necrotic myelopathy, subacute combined degeneration of spinal cord in diseases classified elsewhere, myelopathy, drug-induced, radiation-induced myelitis, disorders of the autonomic nervous system, disorders of peripheral autonomic, sympathetic, parasympathetic, or vegetative system, familial dysautonomia [Riley-Day syndrome], idiopathic peripheral autonomic neuropathy, carotid sinus syncope or syndrome, cervical sympathetic dystrophy or paralysis. peripheral autonomic neuropathy in disorders classified elsewhere, amyloidosis, diseases of the peripheral nerve system, brachial plexus lesions, cervical rib syndrome, costoclavicular syndrome, scalenus anterior syndrome, thoracic outlet syndrome, brachial neuritis or radiculitis, including in newborn. Inflammatory and toxic neuropathy, including acute infective polyneuritis, Guillain-Barre syndrome, Postinfectious polyneuritis, polyneuropathy in collagen vascular disease, disorders affecting multiple structures of eye, purulent endophthalmitis, diseases of the ear and mastoid process, chronic rheumatic heart disease, ischaemic heart disease, arrhythmia, diseases in the pulmonary system, abnormality of organs and soft tissues in newborn, including in the nerve system, complications of the administration of anesthetic or other sedation in labor and delivery, diseases in the skin including infection, insufficient circulation problem, injuries, including after surgery, crushing injury, burns. Injuries to nerves and spinal cord, including division of nerve, lesion in continuity (with or without open wound), traumatic neuroma (with or without open wound), traumatic transient paralysis (with or without open wound), accidental puncture or laceration during medical procedure, injury to optic nerve and pathways, optic nerve injury, second cranial nerve, injury to optic chiasm, injury to optic pathways, injury to visual cortex, unspecified blindness, injury to other cranial nerve(s), injury to other and unspecified nerves. Poisoning by drugs, medicinal and biological substances, genetic or traumatic atrophic muscle disorders; or for the treatment of diseases or conditions of various organs, such as degenerative conditions of the gonads, of the pancreas, such as diabetes mellitus type I and II, of the kidney, such as nephrosis.

A further aspect of the invention is a process of producing a pharmaceutical composition, comprising mixing an effective amount of one or more of the compounds of the invention, or a pharmaceutical composition according to the invention with one or more pharmaceutically acceptable additives or carriers, and administer an effective amount of at least one of said compound, or said pharmaceutical composition to a subject.

In one embodiment of the process as mentioned above, the compounds are used in combination with a prosthetic device, wherein the device is a prosthetic nerve guide. Thus, in a further aspect, the present invention relates to a prosthetic nerve guide, characterised in that it comprises one or more of the compounds or the pharmaceutical composition as defined above. Nerve guides are known in the art.

The invention relates to the use a pharmaceutical composition comprising the compound of invention for the treatment or prophylaxis of any of the diseases and conditions mentioned above.

In yet a further aspect the invention relates to a method of treating a disease or condition as discussed above by administering a compound as defined herein.

EXAMPLES

Production of Recombinant Proteins

The NCAM F3 modules 1, 2 (without expression of exons a, AAG), and FGFR1 Ig modules 2, 3 were produced using rat NCAM cDNA and mouse FGFR1 (IIIC iso-form) cDNA. The F3 module 1 and the combined F3 modules 1, 2 consist of AGHHHHHH (SEQ ID NO:173) and amino acids 507-611 and 507-705 of NCAM (swissprot p13596), respectively. The F3 module 2 consists of AG and amino acids 612-705 of NCAM (swissprot p13596), and is sequentially numbered from 1 to 96, A being numbered 1. The FGFR Ig module 2 consists of AGHHHHHH (SEQ ID NO:173) and amino acids 140-251 of FGFR (swissprot p16092). The FGFR Ig module 3 and the combined Ig modules 2, 3 consist of RSHHHHHH (SEQ ID NO:174) and amino acids 249-365 and 141-365 of FGFR (swissprot p16092), respectively. The F3 modules and the FGFR Ig module 2 were expressed in a KM71 strain of yeast P. pastoris (Invitrogen, USA) as described (Thomsen et al., 1996). The FGFR Ig module 3 and modules 2, 3 were expressed in *Drosophila* S2 cells (Invitrogen, USA) according to the manufacturer's instructions. All the proteins were purified by affinity chromatography using $Ni^{2+}$-NTA resin (Qiagen, USA) and/or ion exchange chromatography and gel filtration. $^{15}$N-labelled F3 module 2 was produced as described (Thomsen et al., 1996). The NCAM Ig modules 1, 2 and 3 (RV and amino acids 20-308 of rat NCAM, swissprot p13596) was produced as described (Soroka et al., 2002).

NMR Analysis: the Structure Calculations of the NCAM F3 Module 2 and Identification of the Residues Involved in Binding with FGFR and ATP The following samples were used for the structure determination of the NCAM F3 module 2: 2 mM module in $H_2O$ or $D_2O$ and 1 mM $^{15}$N-labelled module in $H_2O$. The buffer was 30 mM NaCl, 10 mM sodium phosphate buffer, pH 7.27. The following NMR spectra were recorded and used for assignment: TOCSY in $H_2O$ or $D_2O$ (45 and 70 ms mixing time), NOESY in $H_2O$ or $D_2O$ (80 and 200 ms mixing time), DQF-COSY, $^{15}$N-HSQC, $^{15}$N-TOCSY-HSQC (70 ms mixing time), and $^{15}$N-NOESY-HSQC (125 ms mixing time) (Bodenhausen and Ruben, 1980; Braunsweiler and Ernst, 1983; Kumar et al., 1981; Piantini et al., 1982; Zhang et al., 1994). The NMR experiments were performed on a Bruker AMX-600 MHz and Varian Unity Inova 500, 750 and 800 MHz spectrometers. All spectra were recorded at 298 K. The assignment of the $^1$H and $^{15}$N resonances were performed using the program PRONTO (Kjaer et al., 1994).

Structure Calculation

A distance geometry/simulated annealing protocol using the X-PLOR program was used for structure calculation. The NOE restraints were derived from 80/200 ms NOESY and 125 ms $^{15}$N-NOESY-HSQC spectra with upper bounds of 2.7, 3.3 and 6.0 Å increased by 0.5 Å if the restraint included a methyl group. 40 φ angles restraints with bounds of −120±40° and −57±40°(derived from the $^3J_{HNH\alpha}$ coupling constants) and 4 $\chi^1$ angles were applied. After inspection of hydrogen bond energies, 80 hydrogen bond restraints were applied as NOE restraints with upper bounds of 2 Å and 3 Å for the NH—O and N—O distances, respectively. Of 96 structures calculated, 96 were accepted by X-PLOR, discriminating any structure with an NOE restraint violation >0.5 Å or an angle violation >5°. The structures were examined with MOLMOL, PROCHECK_NMR and WHATCHECK programs. 78 structures had the absolute values of the Z-scores for the $2^{nd}$ generation packing quality, the Ramachandran plot, the $\chi_1/\chi_2$ plot and the backbone conformation less than 3.0. From these 78 structures, 30 structures with the absolute values of the Z-scores less than 2.4 were chosen to represent the structure of the F3 module 2.

Determination of the Structure of the NCAM F3 Module 2 by NMR

Figure 1:
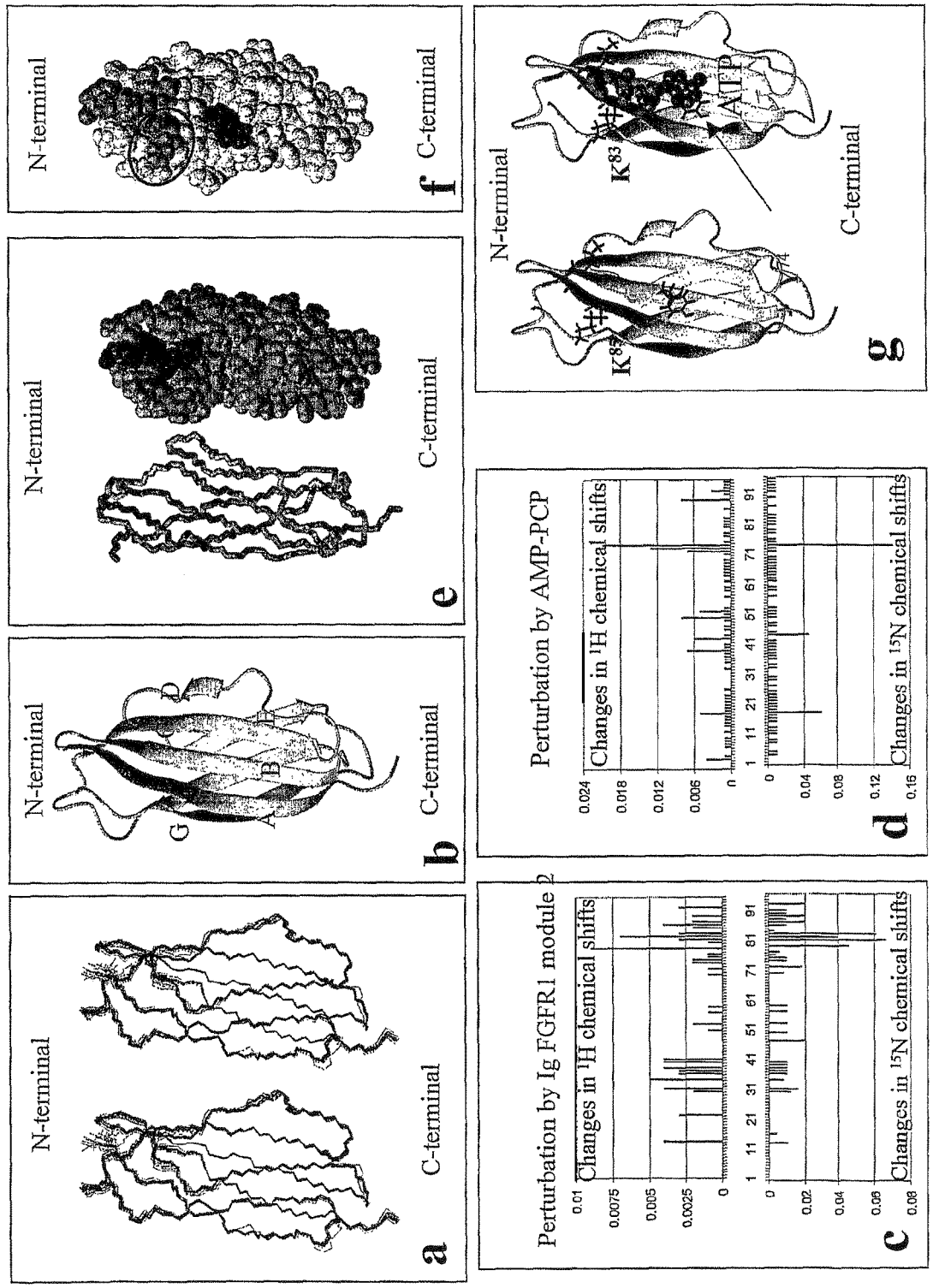
FIG. 1 shows the structure of the NCAM F3 module 2 and demonstrates the regions of the module involved in interaction with the FGFR1 Ig module 3 or AMP-PCP. a) Stereo view of an overlay of the backbone atoms of 30 superimposed structures. b) Ribbon representation of the structure. The N-terminal is located at the top of the picture. c and d) Changes in the chemical shifts of $^1$H and $^{15}$N atoms of 0.05 mM $^{15}$N labeled sample of the NCAM F3 module 2 after addition of 1 mM unlabeled sample of the FGFR1 Ig module 3 (c) or 5 mM AMP-PCP (d). The chemical shifts were determined from the $^{15}$N-HSQC spectra. The data are presented as averages from two independent experiments. e) Mapping of the residues of the NCAM F3 module 2 perturbed by the FGFR Ig module 3 ($N^{79}$, $Q^{81}$, $G^{82}$, $K^{83}$, black) onto the structure of the module. f) Mapping of the residues of the NCAM F3 module 2 perturbed by AMP-PCP, $Y^{74}$ and $V^{75}$ (black), and the residues of the ATP binding Walker motif A, $A^{77}$ENQQGKS$^{84}$ (SEQ ID NO:147) (grey) and $K^{85}$ (dark grey, out-lined) to the structure of the module; all other residues are colored light grey. g) Arrangement of the complex of the NCAM F3 module 2 with ATP. $K^{83}$, $K^{85}$ and $Y^{74}$ are indicated on the ribbon representation of the backbone atoms.

An overlay of 30 superimposed structures for the backbone atoms is shown in FIG. 1A (accession number 1LWR, Protein Data Bank). A ribbon representation of the structure labeling the 7 β-strands is shown in FIG. 1B. A summary of the structural statistics is given in Table 1.

The structure consists of 7 antiparallel β-strands arranged in a sandwich of two β sheets, one containing three strands (ABE) and the other four strands (GFCD). Both of the β sheets have a right-handed twist. The triple-stranded β sheet consists of residues $K^7$-$G^{13}$ (A), $S^{18}$-$I^{24}$ (B), $H^{59}$-$S^{63}$ (E), and the four-stranded β sheet consists of residues $I^{33}$-$A^{42}$ (C), $I^{51}$, $A^{52}$ (D), $E^{70}$-$N^{79}$ (F) and $G^{52}$-$R^{92}$ (G). There are two wide type β-bulges (Chan et al., 1993) involving residues $K^{85}$, $A^{86}$ and $V^{76}$ (G and F β-stands), and residues $A^{77}$ and $H^{35}$, $Y^{36}$ (F and C β-strands). The two β-bulges contribute to the right-handed twist conformation of the four-stranded β-sheet. Analysis of the characteristic β-sheet inter-strand NOEs shows unambiguously that this module has the fibronectin type III fold.

Identification of the Residues of the NCAM F3 Module 2 Interacting with FGFR and ATP In the $^{15}$N-HSQC spectrum of an $^{15}$N-labeled protein, a signal for each amino acid with both a nitrogen and proton can be observed. The changes in the chemical shifts of the signals provide a method for the identification of residues in a protein that are perturbed by the binding of another molecule. To a 50 μM $^{15}$N-labeled sample of the NCAM F3 module 2, 1 mM unlabeled FGFR Ig modules 2 or 3, or 5 mM AMP-PCP (a non-hydrolysable analogue of ATP) were added. No significant changes of the chemical shifts were found in the presence of the Ig module 2 (data not shown). The recorded changes of the chemical shifts in the presence of the Ig module 3 or AMP-PCP are shown in FIG. 1C,D. The residues of the F3 module that exhibited perturbation by the Ig module 3 were $N^{79}$, $Q^{81}$, $G^{82}$ and $K^{83}$ (FIG. 1C). The changes of the chemical shifts of these residues demonstrate that the presence of the Ig module 3 close to the F3 module 2 alters the chemical environment at the perturbed residues of the F3 module, indicating that the perturbed residues are either a part or in the vicinity of the binding site for the interaction between the two modules. These residues are located in the turn region between the F and G β-strands, and as can be seen from FIG. 2E, they are close to the N-terminus of the module and, thus, close to the C-terminus of the F3 module 1 in the NCAM molecule. Since the recombinant protein consisting of the combined F3 modules 1, 2 was found to bind to FGFR with a much higher affinity than any of the two individual F3 modules, it is possible that the perturbed residues at the N-terminus of the F3 module 2 together with residues at the C-terminus of the F3 module 1 form a single binding site which is destroyed when the F3 modules are separated, thus greatly reducing their affinity to FGFR compared to the double module protein.

The residues of the F3 module perturbed by AMP-PCP were $Y^{74}$ and $V^{75}$. The side chain of $Y^{74}$ is exposed on the surface of the module and located in the close vicinity of the nucleotide binding motif: $A^{77}$ENQQGKS$^{84}$ (SEQ ID NO:147) and $K^{85}$ (FIG. 1E). Both $K^{83}$ and $K^{85}$ are exposed on the surface of the module, and presumably the positively charged side chains of $K^{83}$ and $K^{85}$ interact with the negatively charged triphosphate moiety of ATP, whereas the side chain of $Y^{74}$ is involved in a hydro-phobic interaction with the adenosine moiety of ATP. A possible arrangement of the complex of ATP and the F3 module 2 is depicted in FIG. 1G.

The residues perturbed by the FGFR Ig module 3 ($N^{79}$, $Q^{81}$, $G^{82}$ and $K^{83}$) are also a part of the nucleotide binding motif, indicating that the ATP binding site and the FGFR binding site are overlapping.

Thus, these data indicate that $N^{79}$, $Q^{81}$, $G^{82}$ and $K^{83}$ of the NCAM F3 module 2 are located in a site binding to FGFR, and that the FGFR binding site overlaps the ATP binding site.

SPR Analysis of Interaction between FGFR and NCAM

Binding analysis was performed using a BIAcoreX instrument (Biosensor AB) at 25° C. using 10 mM sodium phosphate pH 7.4, 150 mM NaCl as running buffer. The flow-rate was 5 μl/min. Data were analysed by non-linear curve-fitting using the manufacture's software. The FGFR Ig modules 2, 3 were immobilized on a sensor chip CM5 using amine coupling kit (Biosensor AB) as follows: 1) the two halves of the chip (designated Fc1 and Fc2) were activated by 20 μl activation solution; 2) the protein was immobilized on Fc1 using 12 μl 20 μg/ml protein in 10 mM sodium phosphate buffer pH 6.0; 3) Fc1 and Fc2 were blocked by 35 μl blocking solution. Binding of various compounds to the immobilized FGFR modules was studied as follows: A compound was injected simultaneously into Fc1 (with the immobilized FGFR modules) and Fc2 (with nothing immobilized). The curve representing unspecific binding of the compound to the surface of Fc2 was subtracted from the curve representing binding of the protein to the immobilized FGFR modules and the surface of Fc1. The resulting curve was used for analysis. For ATP competition experiments, the specified compounds were pre-incubated for 10 min with ATP at a specified concentration. The Ki of ATP for the interaction between the NCAM F3 modules 1, 2 and the FGFR modules 2, 3 was estimated as previously described (Kiselyov et al, 1997): The initial binding rates of 30 μM F3 modules, $V_0$, and 30 μM F3 modules preincubated with ATP at a specified concentration, $V_{ATP}$, were determined. The % inhibition, $I_\%$, was calculated using the formula: $I_\% = (1 - V_{ATP}/V_0) \times 100$. $I_\%$ was plotted against ATP concentration and Ki was calculated by non-linear fitting of the theoretical curve to the experimental data.

Demonstration of a Direct Interaction Between NCAM and FGFR

Figure 2:
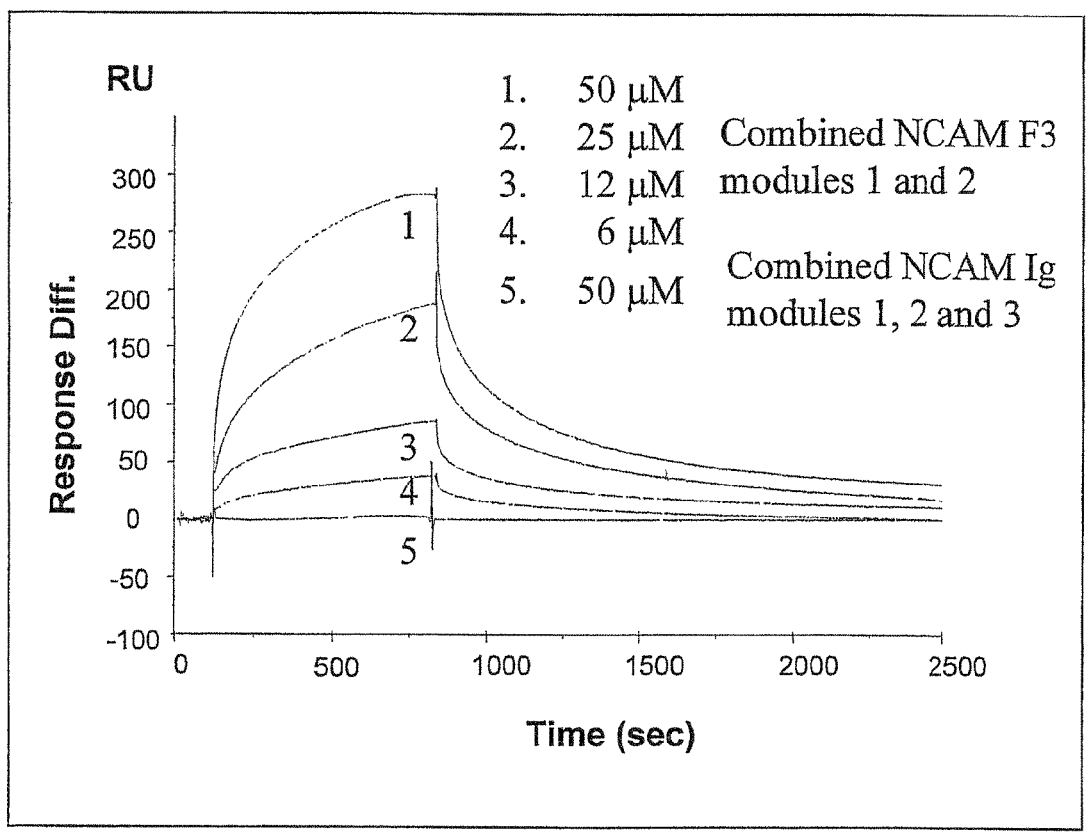
FIG. 2 demonstrates the binding of the combined NCAM F3 modules 1 and 2 to the combined FGFR1 Ig modules 2 and 3 studied by means of surface plasmon resonance (SPR) analysis. The binding is given as a response difference (Resp. Diff.) between the binding to the sensor chip with the immobilized FGFR modules and a blank sensor chip (unspecific binding). Four independent experiments were performed using two different preparations of all proteins used.

From FIG. 2 it appears that a protein consisting of the NCAM F3 modules 1, 2 binds to an immobilized protein comprising the FGFR modules 2, 3, whereas a control protein consisting of the NCAM Ig modules 1, 2 and 3 does not bind to the FGFR fragment. The dissociation constant (Kd) and the coefficients of association and dissociation were: 9.97±0.37 μM, 889±332 $M^{-1}s^{-1}$ and 5.56±0.07×10$^{-3}$ s$^{-1}$ (mean±standard deviation), respectively.

Thus, these data show that the NCAM F3 modules bind directly to FGFR

Binding of NCAM to FGFR can be Inhibited by ATP

Figure 3:
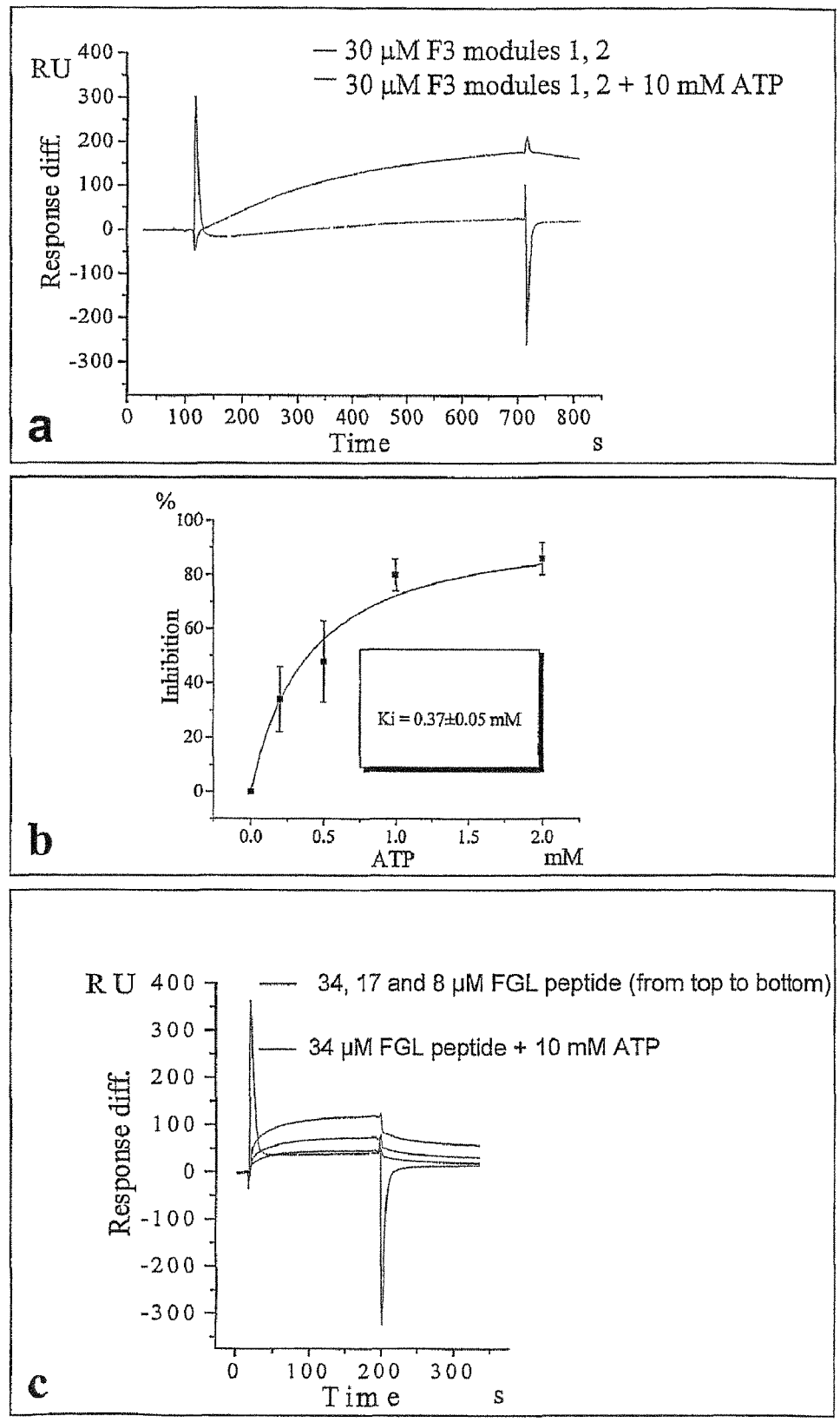
FIG. 3 demonstrates the inhibiting effect of ATP on binding between the FGFR Ig modules 2, 3 and the NCAM F3 modules 1, 2 or the dendrimeric FG loop peptide (SEQ ID NO: 1). The binding was studied by SPR analysis. Approx. 2000 resonance units (RU) of the FGFR modules were immobilized on the sensor chip. Three independent experiments were performed. A) Binding of 30 μM F3 modules 1, 2 to the FGFR modules in the presence or absence of 10 mM ATP. B) A plot of % inhibition by ATP of the binding between 30 μM F3 modules 1, 2 and the immobilized FGFR modules versus the ATP concentration used for inhibition, and the calculated Ki value. C) Binding of the dendrimeric FG loop peptide (34, 17 and 8 μM concentrations) to the immobilized FGFR modules and binding of 34 μM peptide in the presence of 10 mM ATP.

As the NCAM sites binding to FGFR and ATP overlap, then ATP might be expected to interfere with the NCAM-FGFR binding. To test this assumption, SPR analysis was used. As can be seen from FIG. 3A, adding 10 mM ATP to 30 μM NCAM F3 modules 1, 2 completely inhibited binding of the F3 modules to the FGFR Ig modules 2, 3. To determine the inhibition constant (Ki), the inhibition effect was measured at various ATP concentrations (FIG. 3B). The calculated Ki was 0.37±0.05 mM. Since the NMR experiments indicate that the turn region between the F and G β-strands of the F3 module 2 is involved in binding to FGFR, it was of interest to test if a peptide fragment spanning these residues could bind to FGFR. Moreover, another peptide fragment located in the F3 module 1 was of interest to test, as the turn region between the E and F strands of this module may constitute an N-terminal part of the binding site in NCAM interacting with the Ig2-Ig3 module of FGFR. For this purpose, a peptide corresponding to residues $E^{72}$-$A^{86}$ of the F3 module 2 (SEQ ID NO: 1) (termed the FG loop peptide) and a peptide corresponding to residues $T^{573}$-$R^{586}$ of the F3 module 1 (SEQ ID NO: 9) (termed the EF loop peptide). However, binding of monomeric forms of these peptides cannot be detected by SPR. Therefore, there were synthesized dendrimeric versions of the peptides in which four peptide sequences of one type (such as SEQ ID NO: 1 or SEQ ID NO: 9) were connected to a three-lysine backbone through their C-termini. This made it possible for the peptide to bind to several molecules of FGFR simultaneously, thus greatly increasing the apparent affinity of the peptides, and, at the same time, increasing the sensitivity of the SPR analysis four fold (since the molecular weight of each peptide was increased four times).

Figure 4:
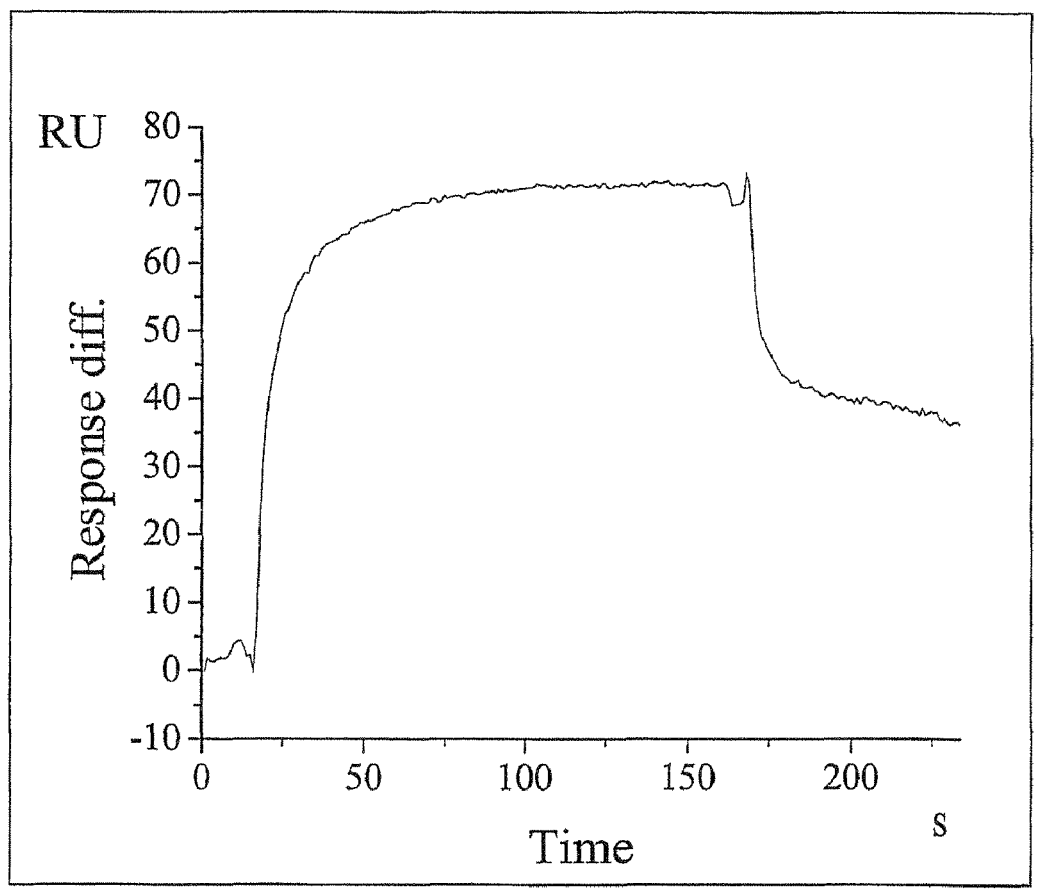
FIG. 4 demonstrates the binding between the dendrimeric EF loop peptide (SEQ ID NO: 9) and the FGFR Ig modules 2, 3 recorded by SPR. The binding is given as a response difference (Resp. Diff.) between the binding to the sensor chip with the immobilized FGFR modules and a blank sensor chip (unspecific binding). Four independent experiments were performed using two different preparations of all proteins used.

As appears from FIG. 3C, the dendrimeric FG loop peptide binds to FGFR with an apparent Kd of 2.58±2.06 μM (the coefficients of association and dissociation being 2.07±1.08× 10$^3$ $M^{-1}s^{-1}$ and 3.97±2.29×10$^{-3}$ s$^{-1}$, respectively). Since binding of the F3 modules 1, 2 to FGFR could be inhibited by ATP and since the peptide contains the entire nucleotide binding motif of NCAM. It was also tested if ATP could interfere with binding of the peptide to FGFR. Indeed, adding 10 mM ATP to 34 μM peptide inhibited the binding by approx. 70% (FIG. 3C). FIG. 4 demonstrates the real-time binding of the dendromeric form of the EF loop peptide to FGFR.

These experiments demonstrate that NCAM binding to FGFR can be inhibited by ATP and support the notion that the turn regions between the F and G β-strands of the F3 module 2 and the E and F β-strands of the F3 module I are involved in binding to FGFR, and that NCAM sites for FGFR and ATP overlap.

Assays for Determination of FGFR1 Phosphorylation and NCAM Immunoprecipitation

Activation of FGFR by the NCAM F3 Module 2 and the FG Loop Peptide

Since the NCAM F3 module 2 and the dendrimeric FG loop peptide bind to FGFR, they may be also expected to induce FGFR activation in living cells. To test this assumption, two assays have been used.

Assay 1: TREX-293 cells (Invitrogen) were stably transfected with human FGFR1 having a C-terminal StrepII-tag (IBA biotech), using the Flp-In system (Invitrogen). For the study of phosphorylation: ~2×10$^7$ cells were starved overnight before stimulation for 20 min with the specified compounds. Cells were lysed in PBS with 1% NP-40 and phosphatase inhibitors cocktail set II (Calbiochem). The cleared cell lysates were incubated with 50 μl agarose-coupled anti-phosphotyrosine antibodies (4G10-AC, Upstate Biotechnologies) for 3 hrs at 4° C. Care was taken to calibrate the amount of cells employed, so that considerable increases in phosphorylated FGFR could be detected. The bound protein was washed, eluted using 150 mM phenyl phosphate (Sigma), precipitated by 12% trichloroacetic acid, washed in cold acetone and dissolved in SDS-PAGE sample buffer. Immunoblotting was performed using antibodies against the recombinant StrepII-tag (IBA biotech). For immunoprecipitation: ~1×10$^7$ cells were transiently transfected with the 180 kDa NCAM isoform or a control vector. Cells were incubated for 24 h and then starved overnight. After lysis, FGFR was purified on a StrepTactin Minicolumn (IBA Biotech) according to the manufacturer's instructions, and analyzed by immunoblotting with polyclonal antibodies against human NCAM.

Figure 5:
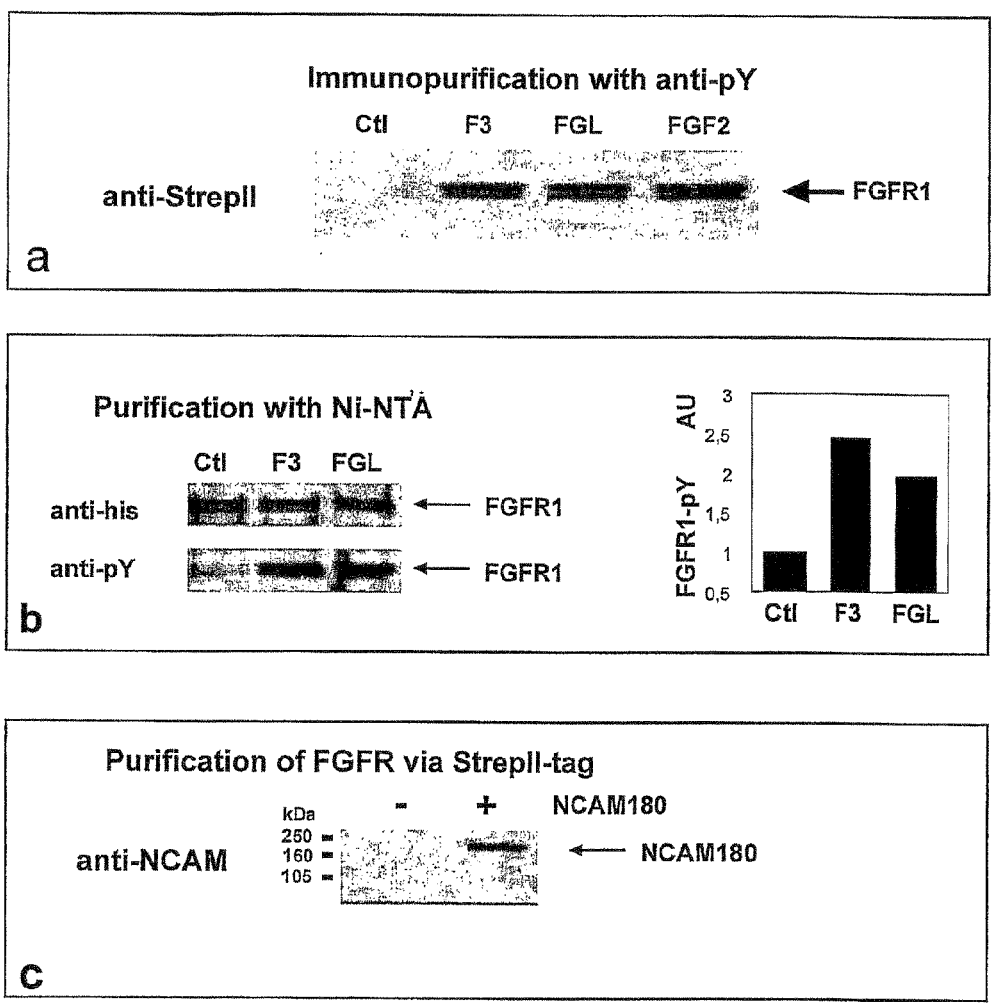
FIG. 5 shows the effect of the NCAM F3 module 2 and the FG loop peptide on phosphorylation of FGFR and demonstrates the immunoprecipitation of NCAM by FGFR. A) TREX-293 cells, stably transfected with FGFR containing a C-terminal StrepII-tag, were stimulated for 20 min with either 10 ng/ml FGF2, 5 μM F3 module 2 or 2.5 μM dendrimeric FG loop peptide. After stimulation, FGFR was immunopurified using anti-phosphotyrosine antibodies and then analyzed by immunoblotting using antibodies against the StrepII-tag. B) HEK293 cells, transiently transfected with a His-tagged version of FGFR1, were stimulated for 20 min with either 5 μM F3 module 2 or 25 μM FG loop peptide. The total amount of FGFR1 and the amount of FGFR phosphorylation was estimated by immunoblotting using anti-pentahis (anti-H is) and anti-phosphotyrosine (anti-pY) antibodies, respectively. Quantification of FGFR phosphorylation was performed by densitometric analysis of the band intensity. Phosphorylation was estimated relative to the control (untreated cells), which has been normalized to 1.0. Error bar represents one standard error of the mean. P<0.05 by paired t-test when comparing treated cells with controls (the t-test was performed on six independent sets of non-normalized data). Ctl stands for the control, F3—F3 module 2, FGL—FG loop peptide. C) TREX-293 cells, stably transfected with FGFR containing a C-terminal StrepII-tag, were transiently transfected with a control vector or NCAM. FGFR was purified from the cell lysate via the StrepII-tag and analyzed by immunoblotting using antibodies against NCAM.

As appears from FIG. 5A, both 5 μM F3 module and 2.5 μM dendrimeric FG loop peptide substantially increase FGFR phosphorylation compared to the non-stimulated cells.

Assay 2: The cDNA for the rat FGFR1 (IIIC isoform) was cloned by RT-PCR using RNA isolated from the rat PC12 cell line and inserted into a pcDNA3.1(+) plasmid (invitrogen), which allows expression of FGFR1 fused to the N-terminal of hexahistidine. ~8×10$^5$ HEK293 cells were cultured for 24 h in 60 mm plates in full medium (DMEM 1965 supplemented with 10% FCS, 100 U/ml penicillin, 100 μg/ml streptomycin and 58.4 g/l Glutamax) and then transfected with 0.2 μg plasmid (with FGFR) using the LipofectAMIN PLUS™ reagent kit according to the manufacturer's instructions (Gibco BRL). Cells were grown for another 24 hrs in full medium, and then shifted to starvation media (DMEM 1965) overnight. FGFR transfected cells were stimulated for 20 min with the specified compounds, lysed in 8M urea, 1 mM orthovanadate (in PBS) and purified from the lysate via the His-tag as follows: The lysate was loaded on Ni$^{2+}$/NTA-sepharose (Qiagen), washed with lysis buffer plus 10 mM imidazole, and the FGFR was eluted with lysis buffer plus 250 mM imidazole. The purified FGFR was analysed by immunoblotting using anti-pentahis (Qiagen) or anti-phosphotyrosine (PY20, Transduction Laboratories) antibodies. The bands were visualised by chemilumiscense and the band density was measured using a GeneGnome apparatus (SynGene).

From FIG. 5B, it appears that addition of 5 μM F3 module 2 or 25 μM monomeric FG loop peptide increase FGFR phosphorylation by approx. 150% and 100%, respectively, compared to control cells.

Co-Immunoprecipitation of NCAM and FGFR

Since the binding between the NCAM and FGFR fragments could be demonstrated in vitro by SPR and NMR analyses it was of interest to confirm that native NCAM binds to FGFR in the living cells. Therefore, TREX-293 cells, stably transfected with FGFR containing a C-terminal StrepII-tag, were transiently transfected with the 180 kDa NCAM isoform. After lysing the cells, FGFR was affinity purified via the StrepII-tag and analyzed by immunoblotting using antibodies against NCAM. As appears from FIG. 5C, NCAM is indeed precipitated by FGFR, thus supporting our SPR and NMR experiments.

Stimulation of Neurite Length of Hippocampal Neurons by the NCAM F3 Module 2, FG Loop (FGL-Peptide, SEQ ID NO: 1), EF Loop Peptide (EFL-Peptide, SEQ ID NO: 9) and a Peptide Derived from the Axonal-Associated Cell Adhesion Molecule.

Dissociated neurons from embryonic rat hippocampus (embryonic day 19), prepared as described (Skladchikova et al., 1999), were grown on Permanox plastic (Nunc) for 24 h at a density of 6000 cells/cm$^2$, at 37° C., 5% $CO_2$ in Neurobasal medium containing 20 mM Hepes, 100 U/ml penicillin, 100 μg/ml streptomycin, 0.4% BSA supplemented with B27 (Gibco BRL) and the below specified compounds. After 24 h, cells were fixed with paraformaldehyde, stained with Coomassie Brilliant Blue R250 and the length of neurites was measured as described (Skladchikova et al, 1999).

Figure 6:
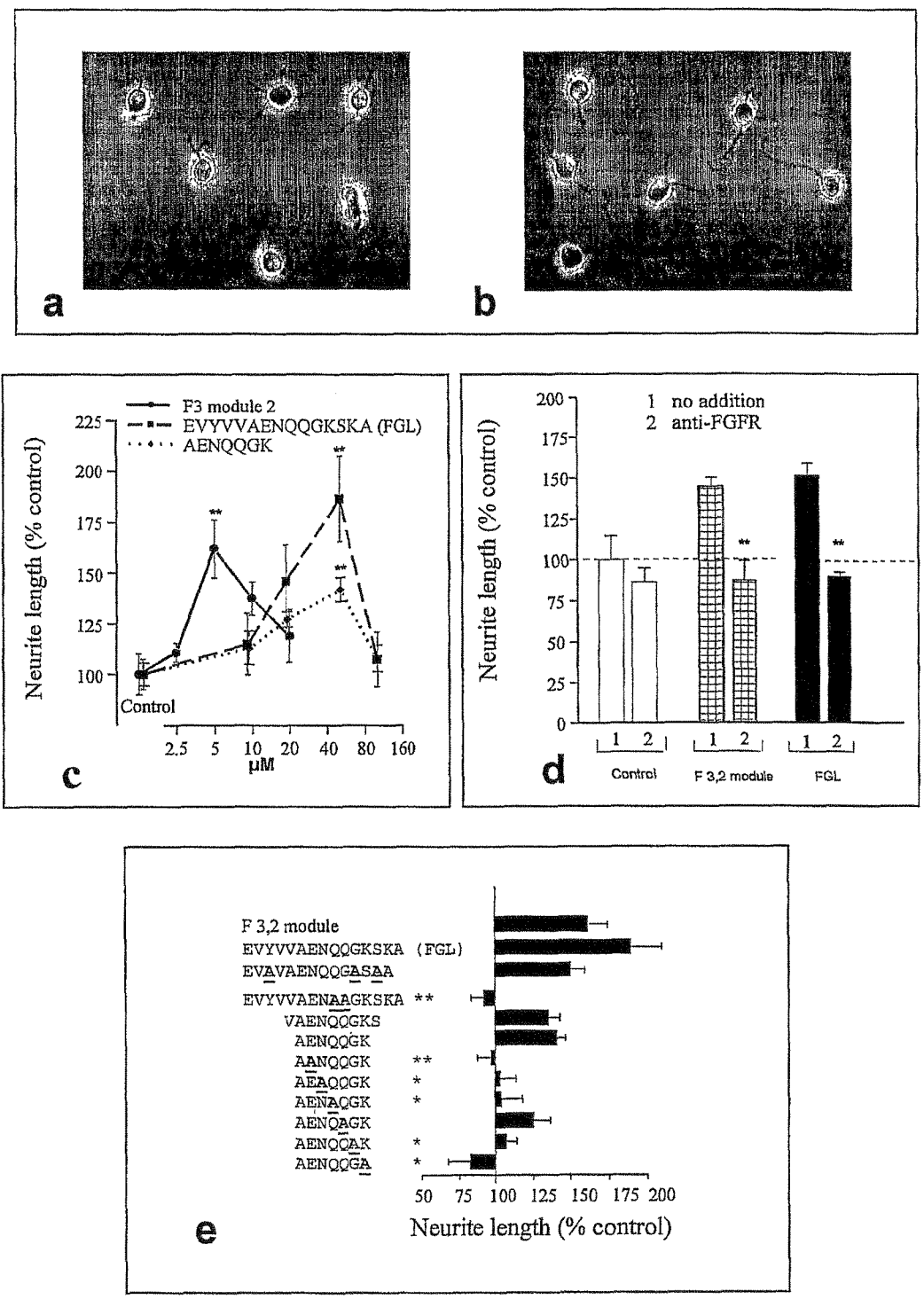
FIG. 6 shows the effect of the NCAM F3 module 2 and its FGFR binding part (the FG loop peptide (SEQ ID NO: 1)) on neurite outgrowth from hippocampal neurons. a) Phase contrast micrograph of control (untreated) neurons. b) Phase contrast micrograph of neurons treated with 5 μM F3 module. c) Neurite length versus the concentration of the F3 module, the FG-loop peptide (SEQ ID NO:1) and a truncated version of the peptide (SEQ ID NO:151). d) Effect of an anti-FGFR antibody on neurite outgrowth induced by 5 μM F3 module or 50 μM FG loop peptide. e) Effect of substitutions of the various amino acids with Ala in the FG loop peptide or truncated versions of the peptide on neurite outgrowth from hippocampal neurons. The enumerated sequences in the table are, in order, SEQ ID NOs:1, 148, 149, and 150-157. The concentration of the various peptides was in all cases 50 μM. Four independent experiments were performed. Error bar represents one standard error of the mean. * and ** stand for statistical significance of p<0.05 and p<0.01, respectively (by t-test).
Figure 7:
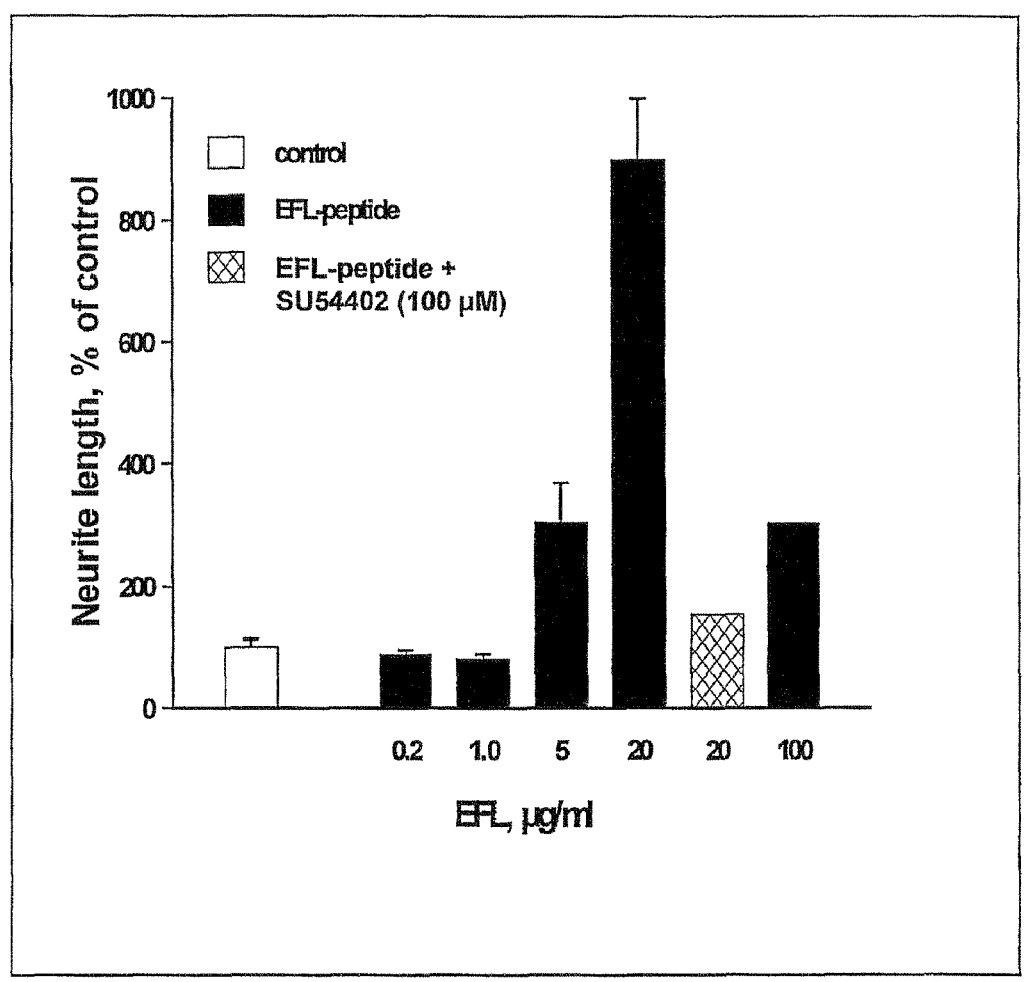
FIG. 7 shows the effect of the EF loop peptide (EFL-peptide) (SEQ ID NO: 9) on neurite outgrowth from hippocampal neurons. SU5402 is a specific inhibitor of FGFR1.

As can be seen from FIG. 6A,B, 5 μM F3 module 2 substantially increased the length of neurites compared to the non-stimulated neurons. The effect was quantified in a dose-response study (FIG. 6C) demonstrating that the F3 module, the FG loop peptide and a truncated version of the peptide ($A^{77}$-$K^{83}$) all induced neurite outgrowth with a bell-shaped curve typical of growth factor induced neuritogenesis (Hatten et al., 1988). The potency of the peptides was lower than that of the module, since a 10 times higher concentration was required for maximum effect, and the truncated form was less efficient than the extended form. The stimulatory effect of the F3 module and the FG loop peptide could be completely abrogated by an inhibitor of NCAM-stimulated neurite outgrowth, an antibody against FGFR (Williams et al., 1994) (FIG. 6D), further supporting the notion that the module and the FG loop peptide interact with FGFR. The EF loop peptide of the F3 module 2 was also capable to stimulate the neurite outgrowth significantly. As it appears from FIG. 7 the neurite outgrowth stimulation by the peptide was specifically blocked by an inhibitor of FGFR1, SU54402.

To determine the functionally important amino acids of the FG loop peptide, it was analyzed by truncations and Ala substitutions of various amino acids. Two truncated versions (from the N- and C-terminal) of the FG loop peptide were produced: the nonamer $V^{76}$-$S^{84}$ and the heptamer $Ala^{77}$-$K^{83}$. Both of the truncated peptides retained approximately 50% of the stimulatory effect of the entire FG loop peptide (FIG. 6E), indicating that the turn region between the F and G β-strands is important for the NCAM-FGFR interaction. As can be seen from FIG. 6E, substitution of any amino acid in the heptameric peptide with Ala resulted in a decrease of the neuritogenic potency and a complete loss of function was achieved if $E^7$, $N^{79}$, $Q^{80}$, $G^{82}$, $K^{83}$ were substituted, indicating that these residues are important for interaction with FGFR. Substitution of both $Q^{80}$ and $Q^{81}$ from the turn region of the FG loop with Ala in the entire FG loop peptide also completely inactivated the peptide (FIG. 6E). These findings corroborate the NMR experiments showing that $N^{79}$, $Q^{81}$, $G^{82}$ and $K^{83}$ were perturbed in the F3 module 2 by binding to the FGFR Ig module 3. However, when the residues which seem to be important for interaction with ATP ($Y^{74}$, $K^{83}$ and $K^{85}$) were substituted with Ala in the FG loop peptide, the peptide retained about 60% of the stimulatory effect of the non-mutated peptide (FIG. 6E).

Figure 8:
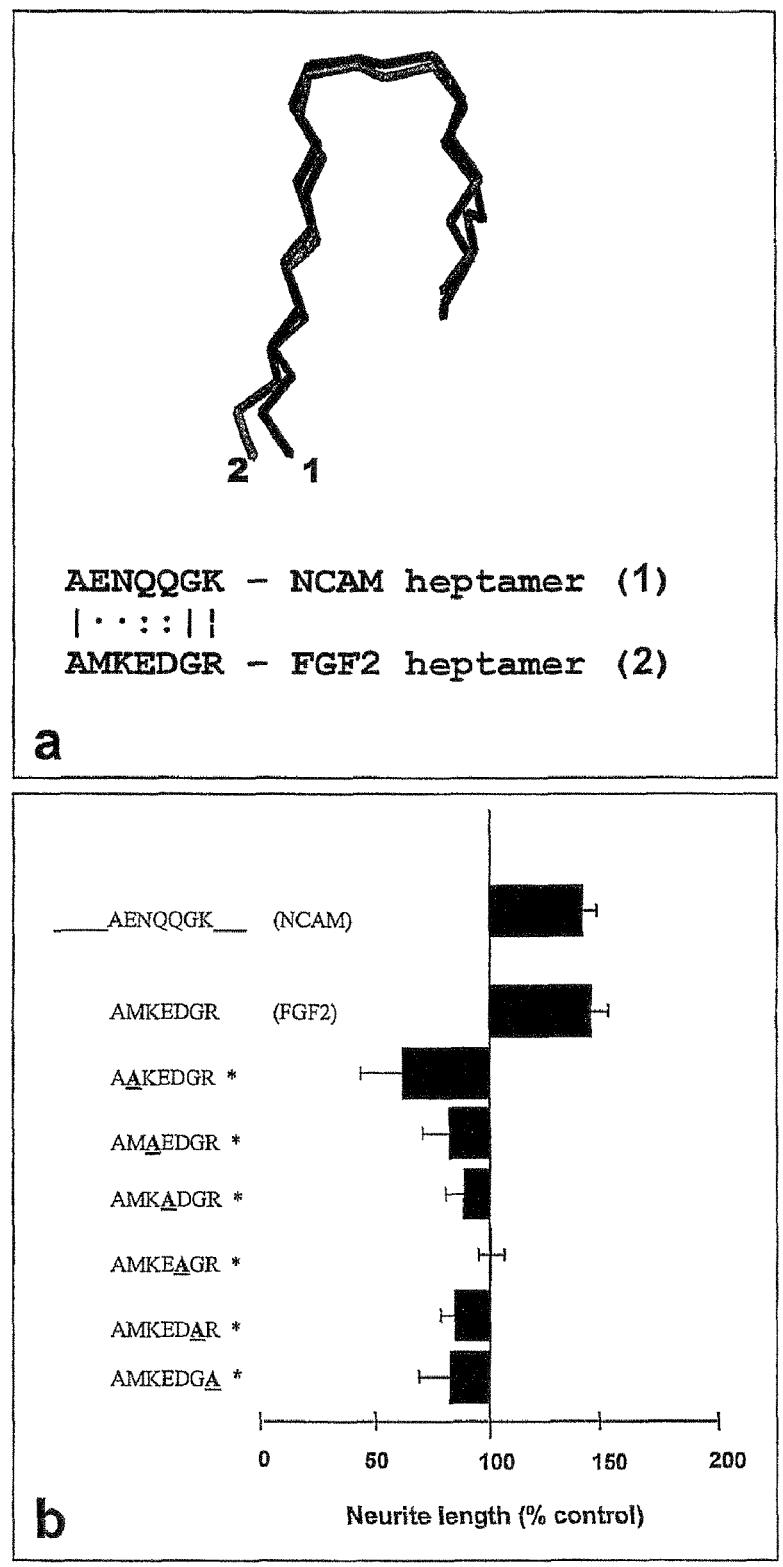
FIG. 8 displays a sequential, structural and functional similarity between peptides (SEQ ID Nos: 151 and 158) derived from the FGFR binding part of NCAM and FGF2. a) Sequential alignment of the peptides (SEQ ID Nos: 151 and 158), in which the signs |, |, :, ● indicate the level of similarity in decreasing order from strong to low similarity; and structural alignment of the backbone atoms of the peptides from NCAM (1) and FGF2 (2). b) Effect of the NCAM derived peptide (SEQ ID NO:151), the FGF2 derived peptide (SEQ ID NO:158), and various Ala substituted forms (SEQ ID Nos: 159-164) on neurite outgrowth from hippocampal neurons including a comparison to the corresponding NCAM derived peptide. Four independent experiments were performed. Error bar represents one standard error of the mean. * stands for statistical significance of p<0.05 (by t-test).

Furthermore, the structure of the heptameric peptide in the F3 module was compared to the known structure of a natural ligand of FGFR, FGF2 (PDB code: 4FGF, Eriksson et al., 1993), and it was found that the peptide exhibited a striking structure and sequence similarity to a loop region in FGF2, $A^{42}$-$R^{41}$ (FIG. 8A). The conformations of the backbone atoms of the two peptides are virtually identical, with the side chains also having similar conformations. The only exception is $R^{48}$ (in FGF2) whose side chain has a somewhat different conformation from that of $K^{83}$. As can be seen from FIG. 8B, the peptide derived from FGF2 induced neurite outgrowth to the same extent as the similar NCAM peptide, and substitution of any amino acid with Ala resulted in a complete loss of function. The close sequence and structure similarity between the FG loop of the NCAM F3 module 2 and a part of FGF2 further corroborate the present contention that the former is directly interacting with FGFR.

Figure 9:
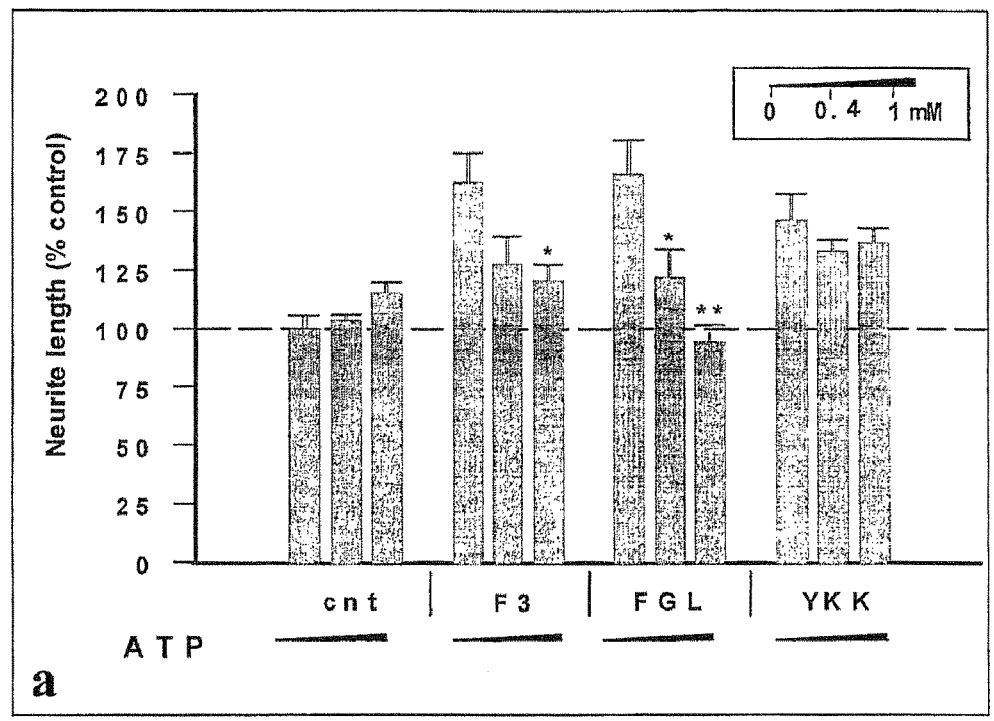
FIG. 9 exhibits the effect of ATP (a) and AMP-PCP (b) on the potency of the NCAM F3 module 2, the monomeric FG loop peptide and a modified version of the peptide to stimulate neurite outgrowth from hippocampal neurons. Neurons were stimulated with either 5 μM second F3 module or 50 μM peptide in the presence of various concentrations of ATP or AMP-PCP (0, 0.4, 1.0 mM). cnt stands for control, F3—the F3 module, FGL—the FG loop peptide, and YKK—the FG loop peptide in which $Y^{74}$, $K^{83}$ and $K^{85}$ were substituted with alanine. Four independent experiments were performed. Error bar represents one standard error of the mean. * and ** stand for statistical significance of p<0.05 and p<0.01, respectively (by t-test).
Figure 9:
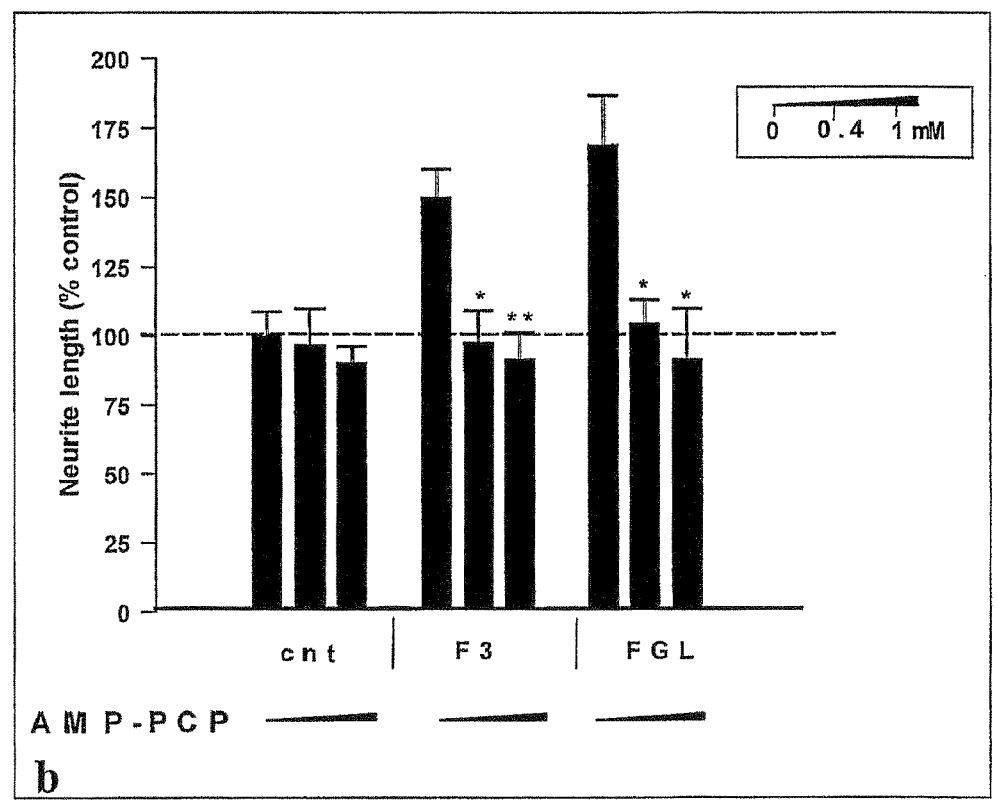

Since ATP can inhibit the NCAM-FGFR binding and interfere with the FGFR activation by the F3 module 2 and, it may consequently affect the neuritogenic activity of the module. To test this assumption, neurons were stimulated with the below described compounds in the presence of ATP or AMP-PCP. As can be seen from FIG. 9, both ATP and AMP-PCP substantially reduced the neuritogenic effect induced by the F3 module 2 and the FG loop peptide. A complete inhibition of the effect of both the F3 module and the FG loop peptide was achieved when AMP-PCP was added, whereas only the effect of the FG loop peptide was completely inhibited when ATP was added, indicating that ATP is a less potent inhibitor than its non-hydrolysable analogue. Most significantly, when the amino acid residues of the FG loop peptide presumed to be of importance for ATP binding ($Y^{74}$, $K^{83}$ and $K^{85}$) were substituted with Ala, the peptide retained its neuritogenic potency, but the stimulatory effect of the peptide could no longer be inhibited by ATP (FIG. 9), supporting the notion that ATP binding regulates the interaction between the F3 module and FGFR.

These results shows that activation of FGFR in neurons by the NCAM F3 module 2, the FG loop and EF loop peptides induce neuritogenesis and that this effect can be inhibited by ATP or a ATP analogue.

To investigate a neuritogenic potency of other FGL-like peptides, which according to invention constitute at least a part of the binding site of the FGFR in a FGFR ligand, a peptide consisting of the sequence derived from the axonal-associated cell adhesion molecule [NCBI: NP_031544.1] was used in the assay described above. The selected peptide was an 11-amino acid fragment of the sequence set forth in SEQ ID NO: 5 having two amino acids truncated from the C-terminus. FIG. 11 demonstrates that likewise the FG-loop and EF-loop peptides the peptide was capable of stimulation of neurite outgrowth of hippocampal neurons. The maximal effect was observed at concentration of the peptide of about 0.3 µg/ml.

Epitope Specific Antibodies

Antibody specifically recognising an epitope comprising SEQ ID NO: 1 (FGL-peptide) were raised in rabbits according the standard procedure (Gill B M, Barbosa J A, Dinh T Q, Garrod S, O'Connor D T: Chromogranin B: isolation from pheochromocytoma, N-terminal sequence, tissue distribution and secretory vesicle processing. Regul Peptides 33:223-35, 1991). Synthetic FGL-peptide was coupled to a carrier protein, KLH (Keyhole Limpets Hemocyanin). The peptide was mixed with Freunds incomplete adjuvant and the mixture was injected into rabbits. 208 µg peptide was used per immunisation (per rabbit).

Figure 10:
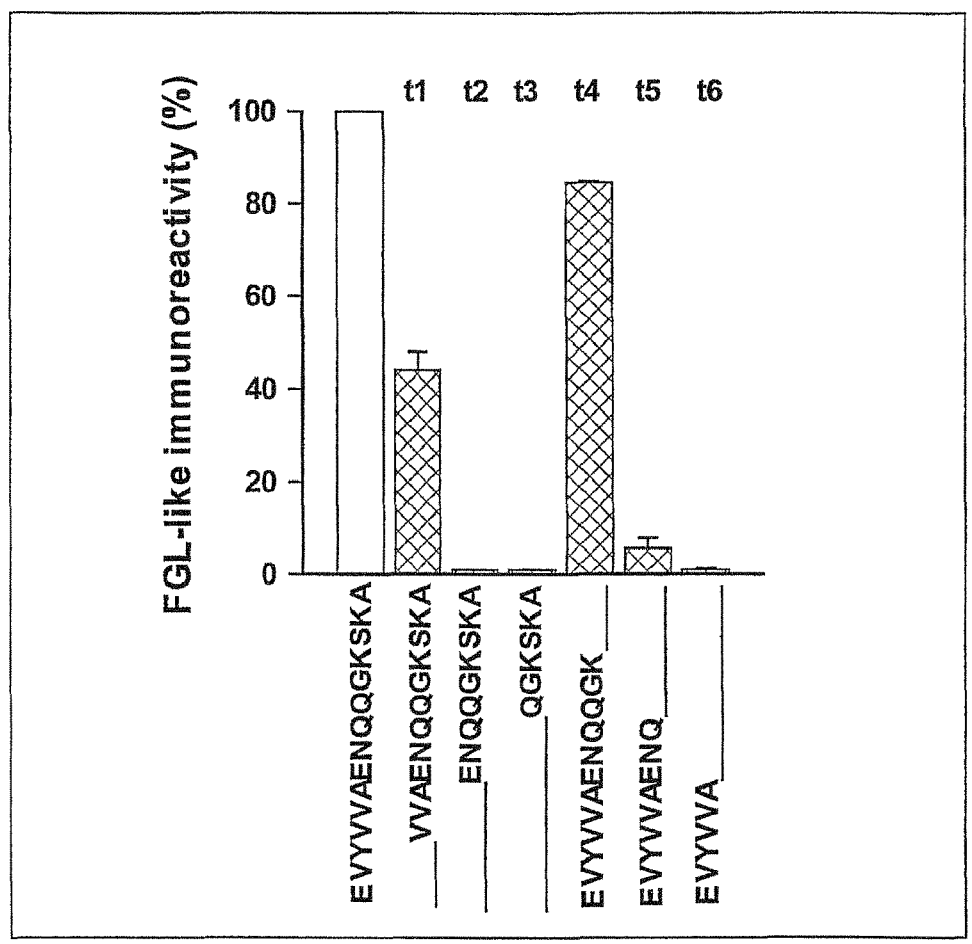
FIG. 10 shows immunoreactivity of the intact FGL-peptide (SEQ ID NO: 1) (open bar) and various truncated variants thereof (t1-t6, SEQ ID NOs:165-170, cross-hatched bars)

Antibodies (serum) were tested for specificity by competitive ELISA using a series FGL-peptide truncated variants according to the protocol described in R. J. Jenny, T. L. Messier, L. A. Ouellette, and W. R. Church, Methods Enzymol. 222, 400 (1993). The results of the test are presented in FIG. 10. 100% immunoreactivity was ob-served only with the intact FGL-peptide consisting of SEQ ID NO: 1. However, two truncated variants of the FGL peptide comprising the motif VVAENQQGK (SEQ ID NO:172) did demonstrate a decreased, but distinct immunoreactivity: peptide t4 lacking the three C-terminal amino acids of full-length FGL-peptide (80% immunoreactivity), and peptide t1 lacking the three N-terminal amino acids of full-length FGL-peptide (40% immunoreactivity).

The invention claimed is:

1. An isolated, non-naturally occurring polypeptide, 6 to 16 amino acids in length, comprising an amino acid sequence that is identical to SEQ ID NO:9, or identical to a fragment, at least 6 contiguous amino acids in length, of SEQ ID NO:9, said polypeptide being capable of interacting with a functional cell-surface fibroblast growth factor receptor.

2. An isolated, non-naturally occurring compound comprising a polypeptide according to claim 1, said compound being capable of interacting with a functional cell-surface fibroblast growth factor receptor.

3. The polypeptide of claim 1 that comprises SEQ ID NO:9.

4. The polypeptide of claim 1 that consists of SEQ ID NO:9.

5. The polypeptide of claim 1 wherein said fragment comprises at least 7 contiguous amino acids of SEQ ID NO:9.

6. The polypeptide of claim 1 wherein said fragment comprises at least 8 contiguous amino acids of SEQ ID NO:9.

7. The polypeptide of claim 1 wherein said fragment comprises at least 9 contiguous amino acids of SEQ ID NO:9.

8. The polypeptide of claim 1 wherein said fragment comprises at least 10 contiguous amino acids of SEQ ID NO:9.

9. The polypeptide of claim 1 wherein said fragment comprises at least 11 contiguous amino acids of SEQ ID NO:9.

10. The polypeptide of claim 1 wherein said fragment comprises at least 12 contiguous amino acids of SEQ ID NO:9.

11. The polypeptide of claim 1 wherein said fragment comprises at least 13 contiguous amino acids of SEQ ID NO:9.

12. The polypeptide of claim 1, in soluble form.

13. A method of modulating the interaction between a functional cell-surface fibroblast growth factor receptor, and a polypeptide having a binding site to said receptor, said method comprising
   i) providing a compound according to claim 2 that is capable of binding with the receptor at the binding site of the receptor for the polypeptide;
   ii) presenting the compound of step (i) to the receptor and the polypeptide and thereby modulating the interaction between a functional cell-surface fibroblast growth factor receptor and a polypeptide having a binding site to said receptor.

14. The method according to claim 13, wherein the cell-surface receptor is selected from the family of fibroblast growth factor receptors (FGFRs) comprising FGFR1, FGFR2, FGFR3 and FGFR4.

15. The method according to claim 13, wherein the receptor is FGFR1.

16. The method according to claim 13, wherein the polypeptide is Neural Cell Adhesion Molecule (NCAM).

17. The method according to claim 13, wherein the compound is a peptide.

18. An isolated, non-naturally occurring compound which is
   (I) a peptide that is
      (a) SEQ ID NO:9, or
      (b) a fragment, at least 6 contiguous amino acids in length, of SEQ ID NO:9,
   (II) a multimer comprising a plurality of peptides, each of which is a peptide according to (I) above.

19. The compound of claim 18 wherein the multimer is a dendrimer.

20. A method of modulating the interaction between a functional cell-surface fibroblast growth factor receptor, and a polypeptide having a binding site to said receptor, said method comprising
   i) providing a compound according to claim 18 that is capable of binding with the receptor at the binding site of the receptor for the polypeptide;
   ii) presenting the compound of step (i) to the receptor and the polypeptide and thereby modulating the interaction between a functional cell-surface fibroblast growth factor receptor and a polypeptide having a binding site to said receptor.

* * * * *

SEQUENCE LISTING

```
<160> NUMBER OF SEQ ID NOS: 174

<210> SEQ ID NO 1
<211> LENGTH: 15
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif

<400> SEQUENCE: 1

Glu Val Tyr Val Val Ala Glu Asn Gln Gln Gly Lys Ser Lys Ala
1               5                   10                  15

<210> SEQ ID NO 2
<211> LENGTH: 16
<212> TYPE: PRT
<213> ORGANISM: Artificial sequence
<220> FEATURE:
<223> OTHER INFORMATION: Interleukin-6 receptor beta chain [Swiss-Prot:
      Q00560]: FGFR binding motif

<400> SEQUENCE: 2

Asn Ile Glu Val Trp Val Glu Ala Glu Asn Ala Leu Gly Lys Lys Val
1               5                   10                  15

<210> SEQ ID NO 3
<211> LENGTH: 14
<212> TYPE: PRT
<213> ORGANISM: Artificial sequence
<220> FEATURE:
<223> OTHER INFORMATION: Heparan sulfate proteoglycan perlecan
      [Swiss-Prot: P98160]: FGFR binding motif

<400> SEQUENCE: 3

Ala Thr Asn Arg Gln Gly Lys Val Lys Ala Phe Ala His Leu
1               5                   10

<210> SEQ ID NO 4
<211> LENGTH: 16
```

```
<212> TYPE: PRT
<213> ORGANISM: Artificial sequence
<220> FEATURE:
<223> OTHER INFORMATION: Disintegrin and metalloprotease domain 8
      (ADAM-8) [Swiss-Prot: Q05910]: FGFR binding motif

<400> SEQUENCE: 4

Arg Tyr Val Glu Leu Tyr Val Val Ala Asp Ser Gln Glu Phe Gln Lys
1               5                   10                  15

<210> SEQ ID NO 5
<211> LENGTH: 13
<212> TYPE: PRT
<213> ORGANISM: Artificial sequence
<220> FEATURE:
<223> OTHER INFORMATION: Axonal-associated cell adhesion molecule
      [NCBI: NP_446331]: FGFR binding motif

<400> SEQUENCE: 5

Val Ala Glu Asn Ser Arg Gly Lys Asn Val Ala Lys Gly
1               5                   10

<210> SEQ ID NO 6
<211> LENGTH: 14
<212> TYPE: PRT
<213> ORGANISM: Artificial sequence
<220> FEATURE:
<223> OTHER INFORMATION: Myelin-associated glycoprotein (MAG)
      [Swiss-Prot: P20917]: FGFR binding motif

<400> SEQUENCE: 6

Gly Glu Tyr Trp Cys Val Ala Glu Asn Gln Tyr Gly Gln Arg
1               5                   10

<210> SEQ ID NO 7
<211> LENGTH: 14
<212> TYPE: PRT
<213> ORGANISM: Artificial sequence
<220> FEATURE:
<223> OTHER INFORMATION: FIII,1 domain of NCAM [Swiss-Prot: P13591]:
      FGFR binding motif

<400> SEQUENCE: 7

Arg Leu Ala Ala Leu Asn Gly Lys Gly Leu Gly Glu Ile Ser
1               5                   10

<210> SEQ ID NO 8
<211> LENGTH: 16
<212> TYPE: PRT
<213> ORGANISM: Artificial sequence
<220> FEATURE:
<223> OTHER INFORMATION: Neuronal nicotinic acetylcholine receptor alpha
      3 subunit (CHRNA3) [Swiss-Prot: Q8VHH6/P04757:/Q8R4G9/P32297]:
      FGFR binding motif

<400> SEQUENCE: 8

Lys Tyr Ile Ala Glu Asn Met Lys Ala Gln Asn Val Ala Lys Glu Ile
1               5                   10                  15

<210> SEQ ID NO 9
<211> LENGTH: 14
<212> TYPE: PRT
<213> ORGANISM: Artificial sequence
<220> FEATURE:
<223> OTHER INFORMATION: FIII,1 domain of NCAM (Swiss-Prot: P13591):
      FGFR binding motif

<400> SEQUENCE: 9

Thr Ile Met Gly Leu Lys Pro Glu Thr Arg Tyr Ala Val Arg
```

<210> SEQ ID NO 10
<211> LENGTH: 14
<212> TYPE: PRT
<213> ORGANISM: Artificial sequence
<220> FEATURE:
<223> OTHER INFORMATION: Granulocyte colony stimulating factor receptor
      precursor (G-CSF-R; CD114 antigen)[Swiss-Prot: Q99062]: FGFR
      binding motif

<400> SEQUENCE: 10

Lys Gly Leu Gly Glu Ile Ser Ala Ala Thr Glu Phe Lys Thr
1               5                   10

<210> SEQ ID NO 11
<211> LENGTH: 13
<212> TYPE: PRT
<213> ORGANISM: Artificial sequence
<220> FEATURE:
<223> OTHER INFORMATION: NCAM Fn III, 1 [Swiss-Prot: P13591]: FGFR
      binding motif

<400> SEQUENCE: 11

Asn Met Gly Ile Trp Val Gln Ala Glu Asn Ala Leu Gly
1               5                   10

<210> SEQ ID NO 12
<211> LENGTH: 10
<212> TYPE: PRT
<213> ORGANISM: Artificial sequence
<220> FEATURE:
<223> OTHER INFORMATION: Granulocyte colony stimulating factor receptor
      precursor (G-CSF-R; CD114 antigen) [Swiss-Prot: P40223]: FGFR
      binding motif

<400> SEQUENCE: 12

Ile Trp Val Gln Ala Glu Asn Met Leu Gly
1               5                   10

<210> SEQ ID NO 13
<211> LENGTH: 11
<212> TYPE: PRT
<213> ORGANISM: Artificial sequence
<220> FEATURE:
<223> OTHER INFORMATION: Cytokine-like factor-1 precursor (CLF-1)
      [Swiss-Prot: O75462]: FGFR binding motif

<400> SEQUENCE: 13

Glu Ile Trp Val Glu Ala Thr Asn Arg Leu Gly
1               5                   10

<210> SEQ ID NO 14
<211> LENGTH: 10
<212> TYPE: PRT
<213> ORGANISM: Artificial sequence
<220> FEATURE:
<223> OTHER INFORMATION: Interleukin-23 receptor (IL-23R) [Q8NFQ9]: FGFR
      binding motif

<400> SEQUENCE: 14

Val Trp Val Gln Ala Ala Asn Ala Leu Gly
1               5                   10

<210> SEQ ID NO 15
<211> LENGTH: 13
<212> TYPE: PRT
<213> ORGANISM: Artificial sequence
<220> FEATURE:

-continued

<223> OTHER INFORMATION: Complement factor 1 q, alpha polypeptide (C1QA)
     [Swiss-Prot: Q9DCM6]: FGFR binding motif

<400> SEQUENCE: 15

Glu Val Trp Ile Glu Lys Asp Pro Ala Lys Gly Arg Ile
1               5                   10

<210> SEQ ID NO 16
<211> LENGTH: 14
<212> TYPE: PRT
<213> ORGANISM: Artificial sequence
<220> FEATURE:
<223> OTHER INFORMATION: Fasciclin II precursor (FAS2) [Swiss-Prot:
     P22648]: FGFR binding motif

<400> SEQUENCE: 16

Ala Thr Asn Lys Gly Gly Glu Val Lys Lys Asn Gly His Leu
1               5                   10

<210> SEQ ID NO 17
<211> LENGTH: 16
<212> TYPE: PRT
<213> ORGANISM: Artificial sequence
<220> FEATURE:
<223> OTHER INFORMATION: ADAM-19 precursor (EC 3.4.24.-) [Swiss-Prot:
     Q9H013/O35674]: FGFR binding motif

<400> SEQUENCE: 17

Lys Tyr Val Glu Leu Tyr Leu Val Ala Asp Tyr Leu Glu Phe Gln Lys
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: ADAM-8 precursor (EC 3.4.24.-) [Swiss-Prot:
     P78325]: FGFR binding motif

<400> SEQUENCE: 18

Arg Tyr Val Glu Leu Tyr Val Val Val Asp Asn Ala Glu Phe Gln
1               5                   10                  15

<210> SEQ ID NO 19
<211> LENGTH: 16
<212> TYPE: PRT
<213> ORGANISM: Artificial sequence
<220> FEATURE:
<223> OTHER INFORMATION: ADAM-12 precursor (EC 3.4.24.-) [Swiss-Prot:
     O43184; Q61824]: FGFR binding motif

<400> SEQUENCE: 19

Lys Tyr Val Glu Leu Val Ile Val Ala Asp Asn Arg Glu Phe Gln Arg
1               5                   10                  15

<210> SEQ ID NO 20
<211> LENGTH: 16
<212> TYPE: PRT
<213> ORGANISM: Artificial sequence
<220> FEATURE:
<223> OTHER INFORMATION: Metalloproteinase-disintegrin domain containing
     protein TECADAM [AF163291] : FGFR binding motif

<400> SEQUENCE: 20

Lys Tyr Ile Glu Tyr Tyr Val Val Leu Asp Asn Gly Glu Phe Lys Lys
1               5                   10                  15

<210> SEQ ID NO 21

-continued

```
<211> LENGTH: 14
<212> TYPE: PRT
<213> ORGANISM: Artificial sequence
<220> FEATURE:
<223> OTHER INFORMATION: ADAM-33 precursor (EC 3.4.24.-) [Swiss-Prot:
      Q9BZ11/Q923W9]: FGFR binding motif

<400> SEQUENCE: 21

Arg Tyr Leu Glu Leu Tyr Ile Val Ala Asp His Thr Leu Phe
1               5                   10

<210> SEQ ID NO 22
<211> LENGTH: 15
<212> TYPE: PRT
<213> ORGANISM: Artificial sequence
<220> FEATURE:
<223> OTHER INFORMATION: ADAM-1A Fertilin alpha [Swiss-Prot: Q8R533]:
      FGFR binding motif

<400> SEQUENCE: 22

Lys Tyr Val Glu Met Phe Val Val Val Asn His Gln Arg Phe Gln
1               5                   10                  15

<210> SEQ ID NO 23
<211> LENGTH: 14
<212> TYPE: PRT
<213> ORGANISM: Artificial sequence
<220> FEATURE:
<223> OTHER INFORMATION: ADAM-9 [Swiss-Prot: Q13433; Q61072]: FGFR
      binding motif

<400> SEQUENCE: 23

Arg Tyr Val Glu Leu Phe Ile Val Val Asp Lys Glu Arg Tyr
1               5                   10

<210> SEQ ID NO 24
<211> LENGTH: 16
<212> TYPE: PRT
<213> ORGANISM: Artificial sequence
<220> FEATURE:
<223> OTHER INFORMATION: ADAM-7 precursor [Swiss-Prot: Q9H2U9]: FGFR
      binding motif

<400> SEQUENCE: 24

Lys Tyr Val Glu Leu Phe Ile Val Ala Asp Asp Thr Val Tyr Arg Arg
1               5                   10                  15

<210> SEQ ID NO 25
<211> LENGTH: 16
<212> TYPE: PRT
<213> ORGANISM: Artificial sequence
<220> FEATURE:
<223> OTHER INFORMATION: ADAM-7 precursor [Swiss-Prot: O35227; Q63180]:
      FGFR binding motif

<400> SEQUENCE: 25

Lys Phe Ile Glu Leu Phe Val Val Ala Asp Glu Tyr Val Tyr Arg Arg
1               5                   10                  15

<210> SEQ ID NO 26
<211> LENGTH: 16
<212> TYPE: PRT
<213> ORGANISM: Artificial sequence
<220> FEATURE:
<223> OTHER INFORMATION: ADAM-15 precursor [Swiss-Prot: Q9QYV0; O88839]:
      FGFR binding motif

<400> SEQUENCE: 26

Lys Ile Val Glu Lys Val Ile Val Ala Asp Asn Ser Glu Val Arg Lys
```

<210> SEQ ID NO 27
<211> LENGTH: 14
<212> TYPE: PRT
<213> ORGANISM: Artificial sequence
<220> FEATURE:
<223> OTHER INFORMATION: ADAM-15 precursor [Swiss-Prot: Q13444]: FGFR binding motif

<400> SEQUENCE: 27

Val Glu Leu Val Ile Val Ala Asp His Ser Glu Ala Gln Lys
1               5                   10

<210> SEQ ID NO 28
<211> LENGTH: 13
<212> TYPE: PRT
<213> ORGANISM: Artificial sequence
<220> FEATURE:
<223> OTHER INFORMATION: Neural cell adhesion protein BIG-2 precursor [Swiss-Prot: Q62845]: FGFR binding motif

<400> SEQUENCE: 28

Val Ala Glu Asn Ser Arg Gly Lys Asn Ile Ala Lys Gly
1               5                   10

<210> SEQ ID NO 29
<211> LENGTH: 13
<212> TYPE: PRT
<213> ORGANISM: Artificial sequence
<220> FEATURE:
<223> OTHER INFORMATION: Neuronal glycoprotein CNTN3 [Swiss-Prot: Q07409]: FGFR binding motif

<400> SEQUENCE: 29

Ile Ala Glu Asn Ser Arg Gly Lys Asn Val Ala Arg Gly
1               5                   10

<210> SEQ ID NO 30
<211> LENGTH: 12
<212> TYPE: PRT
<213> ORGANISM: Artificial sequence
<220> FEATURE:
<223> OTHER INFORMATION: NB-2(HNB-2/NB-2), a neural cell recognition molecule of the contactin/F3 subgroup [Swiss-Prot: O94779/P97527]: FGFR binding motif

<400> SEQUENCE: 30

Ala Glu Asn Ser Arg Gly Lys Asn Ser Phe Arg Gly
1               5                   10

<210> SEQ ID NO 31
<211> LENGTH: 13
<212> TYPE: PRT
<213> ORGANISM: Artificial sequence
<220> FEATURE:
<223> OTHER INFORMATION: HNB-3/NB-3 [Swiss-Prot: Q9UQ52/P97528/Q9JMB8]: FGFR binding motif

<400> SEQUENCE: 31

Ile Ala Ser Asn Leu Arg Gly Arg Asn Leu Ala Lys Gly
1               5                   10

<210> SEQ ID NO 32
<211> LENGTH: 13
<212> TYPE: PRT
<213> ORGANISM: Artificial sequence
<220> FEATURE:
<223> OTHER INFORMATION: Putative fat-like cadherin precursor (Drosiphila) [Swiss-Prot: Q9VW71]: FGFR binding motif

<400> SEQUENCE: 32

Ile Pro Glu Asn Ser Leu Gly Lys Thr Tyr Ala Lys Gly
1               5                   10

<210> SEQ ID NO 33
<211> LENGTH: 12
<212> TYPE: PRT
<213> ORGANISM: Artificial sequence
<220> FEATURE:
<223> OTHER INFORMATION: Neuronal nicotinic acetylcholine receptor alpha
      3 subunit (CHRNA3) [Swiss-Prot: Q8VHH6/P04757/Q8R4G9/P32297]: FGFR
      binding motif

<400> SEQUENCE: 33

Ile Ala Glu Asn Met Lys Ala Gln Asn Glu Ala Lys
1               5                   10

<210> SEQ ID NO 34
<211> LENGTH: 16
<212> TYPE: PRT
<213> ORGANISM: Artificial sequence
<220> FEATURE:
<223> OTHER INFORMATION: Neuronal acetylcholine receptor protein,
      alpha-6 chain precursor (CHRNA6) [Swiss-prot:Q15825]: FGFR binding
      motif

<400> SEQUENCE: 34

Gln Phe Ile Ala Glu Asn Met Lys Ser His Asn Glu Thr Lys Glu Val
1               5                   10                  15

<210> SEQ ID NO 35
<211> LENGTH: 13
<212> TYPE: PRT
<213> ORGANISM: Artificial sequence
<220> FEATURE:
<223> OTHER INFORMATION: ROBO-1 [O44924]: FGFR binding motif

<400> SEQUENCE: 35

Gly Glu Tyr Trp Cys Val Ala Lys Asn Arg Val Gly Gln
1               5                   10

<210> SEQ ID NO 36
<211> LENGTH: 13
<212> TYPE: PRT
<213> ORGANISM: Artificial sequence
<220> FEATURE:
<223> OTHER INFORMATION: ROBO-1 [AF041082; Q9Y6N7]: FGFR binding motif

<400> SEQUENCE: 36

Gly Ser Tyr Thr Cys Val Ala Glu Asn Met Val Gly Lys
1               5                   10

<210> SEQ ID NO 37
<211> LENGTH: 14
<212> TYPE: PRT
<213> ORGANISM: Artificial sequence
<220> FEATURE:
<223> OTHER INFORMATION: ROBO-1 [AF041082; Q9Y6N7]: FGFR binding motif

<400> SEQUENCE: 37

Gly Lys Tyr Val Cys Val Gly Thr Asn Met Val Gly Glu Arg
1               5                   10

<210> SEQ ID NO 38
<211> LENGTH: 11
<212> TYPE: PRT

-continued

<213> ORGANISM: Artificial sequence
<220> FEATURE:
<223> OTHER INFORMATION: FGFR2 [Q96KM2; P21802]: FGFR binding motif

<400> SEQUENCE: 38

Asn Tyr Thr Cys Val Val Glu Asn Glu Tyr Gly
1               5                   10

<210> SEQ ID NO 39
<211> LENGTH: 12
<212> TYPE: PRT
<213> ORGANISM: Artificial sequence
<220> FEATURE:
<223> OTHER INFORMATION: FGFR2 [Q63241]: FGFR binding site

<400> SEQUENCE: 39

Gly Glu Tyr Thr Cys Leu Ala Gly Asn Ser Ile Gly
1               5                   10

<210> SEQ ID NO 40
<211> LENGTH: 11
<212> TYPE: PRT
<213> ORGANISM: Artificial sequence
<220> FEATURE:
<223> OTHER INFORMATION: Fc receptor-like protein 1[Q96KM2] / fragment
      of IFGP1 [Q96PJ6]: FGFR binding motif

<400> SEQUENCE: 40

Gln Tyr Tyr Cys Val Ala Glu Asn Gly Tyr Gly
1               5                   10

<210> SEQ ID NO 41
<211> LENGTH: 13
<212> TYPE: PRT
<213> ORGANISM: Artificial sequence
<220> FEATURE:
<223> OTHER INFORMATION: Junctional adhesion molecule (JAM-1)
      [Q9JKD5/O88792]: FGFR binding motif

<400> SEQUENCE: 41

Gly Glu Tyr Tyr Gln Glu Ala Glu Gln Asn Gly Tyr Gly
1               5                   10

<210> SEQ ID NO 42
<211> LENGTH: 12
<212> TYPE: PRT
<213> ORGANISM: Artificial sequence
<220> FEATURE:
<223> OTHER INFORMATION: FGFR2 [Q96KM2; P21802]: FGFR binding motif

<400> SEQUENCE: 42

Gly Asn Tyr Thr Cys Leu Val Glu Asn Glu Tyr Gly
1               5                   10

<210> SEQ ID NO 43
<211> LENGTH: 12
<212> TYPE: PRT
<213> ORGANISM: Artificial sequence
<220> FEATURE:
<223> OTHER INFORMATION: Contactin precursor (Neural adhesion molecule
      F3) [Q63198; /P1260; Q12860]: FGFR binding motif

<400> SEQUENCE: 43

Gly Met Tyr Gln Cys Leu Ala Glu Asn Ala Tyr Gly
1               5                   10

<210> SEQ ID NO 44
<211> LENGTH: 11

```
<212> TYPE: PRT
<213> ORGANISM: Artificial sequence
<220> FEATURE:
<223> OTHER INFORMATION: Contactin precursor (Neural adhesion molecule
      F3/F11) [Q28106]: FGFR binding motif

<400> SEQUENCE: 44

Gly Met Tyr Gln Cys Ala Glu Asn Thr His Gly
1               5                   10

<210> SEQ ID NO 45
<211> LENGTH: 12
<212> TYPE: PRT
<213> ORGANISM: Artificial sequence
<220> FEATURE:
<223> OTHER INFORMATION: Contactin precursor (Neural adhesion molecule
      F3/F11) [Q28106]: FGFR binding motif

<400> SEQUENCE: 45

Gly Ile Tyr Tyr Cys Leu Ala Ser Asn Asn Tyr Gly
1               5                   10

<210> SEQ ID NO 46
<211> LENGTH: 12
<212> TYPE: PRT
<213> ORGANISM: Artificial sequence
<220> FEATURE:
<223> OTHER INFORMATION: IFGP2 [Q96PJ5]: FGFR binding motif

<400> SEQUENCE: 46

Gly Gly Tyr Tyr Cys Thr Ala Asp Asn Ser Tyr Gly
1               5                   10

<210> SEQ ID NO 47
<211> LENGTH: 12
<212> TYPE: PRT
<213> ORGANISM: Artificial sequence
<220> FEATURE:
<223> OTHER INFORMATION: Neurofascin precursor [Q90924]: FGFR binding
      motif

<400> SEQUENCE: 47

Gly Glu Tyr Gln Cys Phe Ala Arg Asn Asp Tyr Gly
1               5                   10

<210> SEQ ID NO 48
<211> LENGTH: 12
<212> TYPE: PRT
<213> ORGANISM: Artificial sequence
<220> FEATURE:
<223> OTHER INFORMATION: Neurofascin [Q90924]: FGFR binding motif

<400> SEQUENCE: 48

Gly Glu Tyr Phe Cys Leu Ala Ser Asn Lys Met Gly
1               5                   10

<210> SEQ ID NO 49
<211> LENGTH: 12
<212> TYPE: PRT
<213> ORGANISM: Artificial sequence
<220> FEATURE:
<223> OTHER INFORMATION: Neurofascin 155 Da isoform [Q91Z60]: FGFR
      binding motif

<400> SEQUENCE: 49

Gly Glu Tyr Gln Cys Phe Ala Arg Asn Lys Phe Gly
1               5                   10
```

```
<210> SEQ ID NO 50
<211> LENGTH: 12
<212> TYPE: PRT
<213> ORGANISM: Artificial sequence
<220> FEATURE:
<223> OTHER INFORMATION: Neurofascin 155 Da isoform [Q91Z60]: FGFR
      binding motif

<400> SEQUENCE: 50

Gly Glu Tyr Phe Cys Leu Ala Ser Asn Lys Met Gly
1               5                   10

<210> SEQ ID NO 51
<211> LENGTH: 12
<212> TYPE: PRT
<213> ORGANISM: Artificial sequence
<220> FEATURE:
<223> OTHER INFORMATION: Macrophage scavenger receptor 2 (MSR2)
      [Q91YK7]: FGFR binding motif

<400> SEQUENCE: 51

Gly Gly Tyr Tyr Cys Thr Ala Asp Asn Asn Tyr Gly
1               5                   10

<210> SEQ ID NO 52
<211> LENGTH: 14
<212> TYPE: PRT
<213> ORGANISM: Artificial sequence
<220> FEATURE:
<223> OTHER INFORMATION: Macrophage scavenger receptor 2 (MSR2)
      [Q91YK7]: FGFR binding motif

<400> SEQUENCE: 52

Gly Asn Tyr Ser Cys Glu Ala Glu Asn Ala Trp Gly Thr Lys
1               5                   10

<210> SEQ ID NO 53
<211> LENGTH: 12
<212> TYPE: PRT
<213> ORGANISM: Artificial sequence
<220> FEATURE:
<223> OTHER INFORMATION: Neural cell adhesion molecule L1[Q9QYQ7;
      Q9QY38; P11627; Q05695; P32004]: FGFR binding motif

<400> SEQUENCE: 53

Gly Glu Tyr Thr Cys Leu Ala Glu Asn Ser Leu Gly
1               5                   10

<210> SEQ ID NO 54
<211> LENGTH: 13
<212> TYPE: PRT
<213> ORGANISM: Artificial sequence
<220> FEATURE:
<223> OTHER INFORMATION: Neural-glial cell adhesion molecule Ng-CAM
      [Q03696]: FGFR binding motif

<400> SEQUENCE: 54

Gly Glu Tyr Glu Cys Val Ala Glu Asn Gly Arg Leu Gly
1               5                   10

<210> SEQ ID NO 55
<211> LENGTH: 13
<212> TYPE: PRT
<213> ORGANISM: Artificial sequence
<220> FEATURE:
<223> OTHER INFORMATION: FGFR3 [Q95M13; AF487554; Q99052]: FGFR binding
      motif

<400> SEQUENCE: 55
```

```
Gly Asn Tyr Thr Cys Val Val Glu Asn Lys Phe Gly Arg
1               5                   10

<210> SEQ ID NO 56
<211> LENGTH: 12
<212> TYPE: PRT
<213> ORGANISM: Artificial sequence
<220> FEATURE:
<223> OTHER INFORMATION: FGFR3 [Q95M13; Q99052]: FGFR binding motif

<400> SEQUENCE: 56

Gly Glu Tyr Thr Cys Leu Ala Gly Asn Ser Ile Gly
1               5                   10

<210> SEQ ID NO 57
<211> LENGTH: 12
<212> TYPE: PRT
<213> ORGANISM: Artificial sequence
<220> FEATURE:
<223> OTHER INFORMATION: Neural cell adhesion molecule 2 (NCAM2)
      [P36335]: FGFR binding motif

<400> SEQUENCE: 57

Gly Glu Tyr Phe Cys Val Ala Ser Asn Pro Ile Gly
1               5                   10

<210> SEQ ID NO 58
<211> LENGTH: 12
<212> TYPE: PRT
<213> ORGANISM: Artificial sequence
<220> FEATURE:
<223> OTHER INFORMATION: Neural cell adhesion molecule 2 (NCAM2)
      [P36335]: FGFR binding motif

<400> SEQUENCE: 58

Glu Tyr Thr Cys Ile Ala Asn Asn Gln Ala Gly Glu
1               5                   10

<210> SEQ ID NO 59
<211> LENGTH: 13
<212> TYPE: PRT
<213> ORGANISM: Artificial sequence
<220> FEATURE:
<223> OTHER INFORMATION: Axonin-1 (TAG-1) [Q02246;P22063; P28685]: FGFR
      binding motif

<400> SEQUENCE: 59

Gly Met Tyr Gln Cys Val Ala Glu Asn Lys His Leu Gly
1               5                   10

<210> SEQ ID NO 60
<211> LENGTH: 13
<212> TYPE: PRT
<213> ORGANISM: Artificial sequence
<220> FEATURE:
<223> OTHER INFORMATION: Neural cell adhesion molecule NCAM-140 AND
      ncam-140 [P13595]: FGFR binding motif

<400> SEQUENCE: 60

Gly Glu Tyr Met Cys Thr Ala Ser Asn Thr Ile Gly Gln
1               5                   10

<210> SEQ ID NO 61
<211> LENGTH: 13
<212> TYPE: PRT
<213> ORGANISM: Artificial sequence
<220> FEATURE:
<223> OTHER INFORMATION: Neural cell adhesion molecule NCAM-140 AND
      ncam-140 [P13595]: FGFR binding motif
```

```
<400> SEQUENCE: 61

Glu Tyr Val Cys Ile Ala Glu Asn Lys Ala Gly Glu Gln
1               5                   10

<210> SEQ ID NO 62
<211> LENGTH: 13
<212> TYPE: PRT
<213> ORGANISM: Artificial sequence
<220> FEATURE:
<223> OTHER INFORMATION: Neurotrophin receptor tyrosin kinase type 2
      (NTRKT) [Q8WXJ5]: FGFR binding motif

<400> SEQUENCE: 62

Gly Asp Tyr Thr Leu Ile Ala Lys Asn Glu Tyr Gly Lys
1               5                   10

<210> SEQ ID NO 63
<211> LENGTH: 12
<212> TYPE: PRT
<213> ORGANISM: Artificial sequence
<220> FEATURE:
<223> OTHER INFORMATION: Colorectal cancer suppressor DCC [P43146]: FGFR
      binding motif

<400> SEQUENCE: 63

Gly Phe Tyr Gln Cys Val Ala Glu Asn Glu Ala Gly
1               5                   10

<210> SEQ ID NO 64
<211> LENGTH: 14
<212> TYPE: PRT
<213> ORGANISM: Artificial sequence
<220> FEATURE:
<223> OTHER INFORMATION: Tyrosine phosphatase LAR (ptprf) [Q9EQ17;
      Q64604; P23468]: FGFR binding motif

<400> SEQUENCE: 64

Gly Lys Tyr Glu Cys Val Ala Thr Asn Ser Ala Gly Thr Arg
1               5                   10

<210> SEQ ID NO 65
<211> LENGTH: 12
<212> TYPE: PRT
<213> ORGANISM: Artificial sequence
<220> FEATURE:
<223> OTHER INFORMATION: Platelet-derived growth factor receptor beta
      (PDGFRB) [Q8R406; Q05030]: FGFR binding motif

<400> SEQUENCE: 65

Gly Glu Tyr Phe Cys Val Tyr Asn Asn Ser Leu Gly
1               5                   10

<210> SEQ ID NO 66
<211> LENGTH: 13
<212> TYPE: PRT
<213> ORGANISM: Artificial sequence
<220> FEATURE:
<223> OTHER INFORMATION: Intercellular adhesion molecule-5 (ICAM-5,
      telencephalin) [Q8TAM9; Q60625]: FGFR binding motif

<400> SEQUENCE: 66

Gly Glu Tyr Glu Cys Ala Ala Thr Asn Ala His Gly Arg
1               5                   10

<210> SEQ ID NO 67
<211> LENGTH: 13
<212> TYPE: PRT
```

```
<213> ORGANISM: Artificial sequence
<220> FEATURE:
<223> OTHER INFORMATION: B-cell receptor CD22 precursor (Leu-14;
      B-lymphocyte cell adhesion molecule) [P20273]: FGFR binding motif

<400> SEQUENCE: 67

Gly Ala Tyr Trp Cys Gln Gly Thr Asn Ser Val Gly Lys
1               5                   10

<210> SEQ ID NO 68
<211> LENGTH: 12
<212> TYPE: PRT
<213> ORGANISM: Artificial sequence
<220> FEATURE:
<223> OTHER INFORMATION: B-cell receptor CD22 precursor (Leu-14;
      B-lymphocyte cell adhesion molecule) [P20273]: FGFR binding motif

<400> SEQUENCE: 68

Gly Thr Tyr Ser Cys Val Ala Glu Asn Ile Leu Gly
1               5                   10

<210> SEQ ID NO 69
<211> LENGTH: 14
<212> TYPE: PRT
<213> ORGANISM: Artificial sequence
<220> FEATURE:
<223> OTHER INFORMATION: NCAM-2 [Swiss-Prot: O15394; O35136]: FGFR
      binding motif

<400> SEQUENCE: 69

Arg Val Ala Ala Val Asn Gly Lys Gly Gln Gly Asp Tyr Ser
1               5                   10

<210> SEQ ID NO 70
<211> LENGTH: 14
<212> TYPE: PRT
<213> ORGANISM: Artificial sequence
<220> FEATURE:
<223> OTHER INFORMATION: HCF-2 (Host cell factor 2) [Swiss-Prot:
      Q9Y5Z7]: FGFR binding motif: FGFR binding motif

<400> SEQUENCE: 70

Arg Val Ala Ala Ile Asn Gly Cys Gly Ile Gly Pro Phe Ser
1               5                   10

<210> SEQ ID NO 71
<211> LENGTH: 9
<212> TYPE: PRT
<213> ORGANISM: Artificial sequence
<220> FEATURE:
<223> OTHER INFORMATION: ICLN (Chloride channel regulator, inducer)
      [Swiss-Prot: P97506; Q9NRD2; Q61189; P54105]: FGFR binding motif

<400> SEQUENCE: 71

Ala Val Leu Asn Gly Lys Gly Leu Gly
1               5

<210> SEQ ID NO 72
<211> LENGTH: 11
<212> TYPE: PRT
<213> ORGANISM: Artificial sequence
<220> FEATURE:
<223> OTHER INFORMATION: Galectin-12 [Swiss-Prot: Q91VD1; Q9JKX2;
      Q9NZ03]: FGFR binding motif

<400> SEQUENCE: 72

Ala Leu Asn Gly Gln Gly Leu Gly Ala Thr Ser
1               5                   10
```

```
<210> SEQ ID NO 73
<211> LENGTH: 12
<212> TYPE: PRT
<213> ORGANISM: Artificial sequence
<220> FEATURE:
<223> OTHER INFORMATION: Human receptor-like protein tyrosine
      phosphatase leukocyte common antigen-related molecule (PTPRF)
      [Swiss-Prot: P10586]: FGFR binding motif

<400> SEQUENCE: 73

Arg Leu Ala Ala Lys Asn Arg Ala Gly Leu Gly Glu
1               5                   10

<210> SEQ ID NO 74
<211> LENGTH: 13
<212> TYPE: PRT
<213> ORGANISM: Artificial sequence
<220> FEATURE:
<223> OTHER INFORMATION: Natural resistance-associated macrophage
      protein 1(NRAMP-1, SLC11A1) [Swiss-Prot: O77741]: FGFR binding
      motif

<400> SEQUENCE: 74

Arg Leu Gly Val Val Thr Gly Lys Asp Leu Gly Glu Ile
1               5                   10

<210> SEQ ID NO 75
<211> LENGTH: 14
<212> TYPE: PRT
<213> ORGANISM: Artificial sequence
<220> FEATURE:
<223> OTHER INFORMATION: NCAM2 (180 kDa isoform precursor) [Swiss-Prot:
      P36335]: FGFR binding motif

<400> SEQUENCE: 75

Thr Val Thr Gly Leu Lys Pro Glu Thr Ser Tyr Met Val Lys
1               5                   10

<210> SEQ ID NO 76
<211> LENGTH: 13
<212> TYPE: PRT
<213> ORGANISM: Artificial sequence
<220> FEATURE:
<223> OTHER INFORMATION: Nephrin [Swiss-Prot: Q925S5; Q9JIX2; Q9ET59;
      Q9R044; Q9QZS7]: FGFR binding motif

<400> SEQUENCE: 76

Thr Leu Thr Gly Leu Lys Pro Ser Thr Arg Tyr Arg Ile
1               5                   10

<210> SEQ ID NO 77
<211> LENGTH: 13
<212> TYPE: PRT
<213> ORGANISM: Artificial sequence
<220> FEATURE:
<223> OTHER INFORMATION: Nephrin [Swiss-Prot: O60500]: FGFR binding
      motif

<400> SEQUENCE: 77

Thr Leu Thr Gly Leu Gln Pro Ser Thr Arg Tyr Arg Val
1               5                   10

<210> SEQ ID NO 78
<211> LENGTH: 14
<212> TYPE: PRT
<213> ORGANISM: Artificial sequence
<220> FEATURE:
<223> OTHER INFORMATION: Tyrosine phosphatase LAR (PTPRF) [Swiss-Prot:
      Q9EQ17]: FGFR binding motif
```

<400> SEQUENCE: 78

Thr Leu Leu Gly Leu Lys Pro Asp Thr Thr Tyr Asp Ile Lys
1               5                   10

<210> SEQ ID NO 79
<211> LENGTH: 14
<212> TYPE: PRT
<213> ORGANISM: Artificial sequence
<220> FEATURE:
<223> OTHER INFORMATION: Leukocyte common antigen-related phosphatase
      ptp2 precursor (LAR-PTP2) [Swiss-Prot: Q64605]: FGFR binding motif

<400> SEQUENCE: 79

Thr Leu Gln Gly Leu Arg Pro Glu Thr Ala Tyr Glu Leu Arg
1               5                   10

<210> SEQ ID NO 80
<211> LENGTH: 14
<212> TYPE: PRT
<213> ORGANISM: Artificial sequence
<220> FEATURE:
<223> OTHER INFORMATION: Protein-tyrosine phosphatase, receptor-type, S
      precursor (EC 3.1.3.48) (Protein-tyrosine phosphatase sigma)
      (RPTP-sigma) [Swiss-Prot: Q64699]: FGFR binding motif

<400> SEQUENCE: 80

Thr Leu Arg Gly Leu Arg Pro Glu Thr Ala Tyr Glu Leu Arg
1               5                   10

<210> SEQ ID NO 81
<211> LENGTH: 14
<212> TYPE: PRT
<213> ORGANISM: Artificial sequence
<220> FEATURE:
<223> OTHER INFORMATION: Tyrosine-protein kinase receptor Tie-1
      precursor (TIE1.) (EC 2.7.1.112) [Swiss-Prot: Q06805; P35590]:
      FGFR binding motif

<400> SEQUENCE: 81

Thr Leu Met Asn Leu Arg Pro Lys Thr Gly Tyr Ser Val Arg
1               5                   10

<210> SEQ ID NO 82
<211> LENGTH: 11
<212> TYPE: PRT
<213> ORGANISM: Artificial sequence
<220> FEATURE:
<223> OTHER INFORMATION: Ephrin type-A receptor 8 precursor to (EPHA8..)
      (EC 2.7.1.112)(Tyrosine-protein kinase receptor EEK) (EPH-and
      ELK-related kinase)]: [Swiss-Prot: O09127; O09127; P29322]; FGFR
      binding motif

<400> SEQUENCE: 82

Thr Val Ser Gly Leu Lys Pro Gly Thr Arg Tyr
1               5                   10

<210> SEQ ID NO 83
<211> LENGTH: 11
<212> TYPE: PRT
<213> ORGANISM: Artificial sequence
<220> FEATURE:
<223> OTHER INFORMATION: Ephrin type-A receptor 3 precursor
      (EC 2.7.1.112) (Tyrosine-protein kinase receptor ETK1) (CEK4)
      (EPHA3..) [tn: P29318]: FGFR binding motif

<400> SEQUENCE: 83

Thr Ile Ser Gly Leu Lys Pro Asp Thr Thr Tyr
1               5                   10

-continued

<210> SEQ ID NO 84
<211> LENGTH: 11
<212> TYPE: PRT
<213> ORGANISM: Artificial sequence
<220> FEATURE:
<223> OTHER INFORMATION: Protein-tyrosine phosphatase receptor-type S
      precursor (EC 3.1.3.48) (Protein-tyrosine phosphatase sigma,
      PTPRS) [Swiss-Prot: Q13332]: FGFR binding motif

<400> SEQUENCE: 84

Thr Leu Gln Gly Leu Lys Pro Asp Thr Ala Tyr
1               5                   10

<210> SEQ ID NO 85
<211> LENGTH: 12
<212> TYPE: PRT
<213> ORGANISM: Artificial sequence
<220> FEATURE:
<223> OTHER INFORMATION: Insulin receptor [Swiss-Prot: Q9PWN6]: FGFR
      binding motif

<400> SEQUENCE: 85

Leu Arg Gly Leu Lys Pro Trp Thr Gln Tyr Ala Val
1               5                   10

<210> SEQ ID NO 86
<211> LENGTH: 13
<212> TYPE: PRT
<213> ORGANISM: Artificial sequence
<220> FEATURE:
<223> OTHER INFORMATION: Type VII collagen [Swiss-Prot: Q63870]: FGFR
      binding motif

<400> SEQUENCE: 86

Ile Asp Gly Leu Glu Pro Asp Thr Glu Tyr Ile Val Arg
1               5                   10

<210> SEQ ID NO 87
<211> LENGTH: 12
<212> TYPE: PRT
<213> ORGANISM: Artificial sequence
<220> FEATURE:
<223> OTHER INFORMATION: Insulin-like growth factor-1 receptor precursor
      [Swiss-Prot: O73798]: FGFR binding motif

<400> SEQUENCE: 87

Leu Gln Gly Leu Lys Pro Trp Thr Gln Tyr Ala Ile
1               5                   10

<210> SEQ ID NO 88
<211> LENGTH: 14
<212> TYPE: PRT
<213> ORGANISM: Artificial sequence
<220> FEATURE:
<223> OTHER INFORMATION: Fibronectin [Swiss-Prot: Q95KV4; Q95KV5;
      P07589; Q28377; U42594; O95609]: FGFR binding motif

<400> SEQUENCE: 88

Thr Ile Thr Gly Leu Glu Pro Gly Thr Glu Tyr Thr Ile Gln
1               5                   10

<210> SEQ ID NO 89
<211> LENGTH: 10
<212> TYPE: PRT
<213> ORGANISM: Artificial sequence
<220> FEATURE:
<223> OTHER INFORMATION: Insulin-like growth factor I receptor (IGF I
      receptor beta-subunit, IGF I receptor alpha-subunit) [Swiss-Prot:

Q9QVW4; P08069; P24062; Q60751; P15127; P15208]: FGFR binding motif

<400> SEQUENCE: 89

Gly Leu Lys Pro Trp Thr Gln Tyr Ala Val
1               5                   10

<210> SEQ ID NO 90
<211> LENGTH: 13
<212> TYPE: PRT
<213> ORGANISM: Artificial sequence
<220> FEATURE:
<223> OTHER INFORMATION: Insulin receptor-related protein precursor
      (EC 2.7.1.112) (IRR) (IR-related receptor) [Swiss-Prot: P14616]:
      FGFR binding motif

<400> SEQUENCE: 90

Thr Leu Ala Ser Leu Lys Pro Trp Thr Gln Tyr Ala Val
1               5                   10

<210> SEQ ID NO 91
<211> LENGTH: 12
<212> TYPE: PRT
<213> ORGANISM: Artificial sequence
<220> FEATURE:
<223> OTHER INFORMATION: Tenascin-R (restrictin) [Swiss-Prot: Q15568;
      O00531]: FGFR binding motif

<400> SEQUENCE: 91

Leu Met Gly Leu Gln Pro Ala Thr Glu Tyr Ile Val
1               5                   10

<210> SEQ ID NO 92
<211> LENGTH: 14
<212> TYPE: PRT
<213> ORGANISM: Artificial sequence
<220> FEATURE:
<223> OTHER INFORMATION: Neogenin precursor (NEO1..) [Swiss-Prot:
      Q92859; P97603; Q90610; P97798]: FGFR binding motif

<400> SEQUENCE: 92

Lys Gly Met Gly Pro Met Ser Glu Ala Val Gln Phe Arg Thr
1               5                   10

<210> SEQ ID NO 93
<211> LENGTH: 14
<212> TYPE: PRT
<213> ORGANISM: Artificial sequence
<220> FEATURE:
<223> OTHER INFORMATION: Protein tyrosine phosphatase receptor type D
      (PTPRD, BA175E13.1) [Swiss-Prot: Q8WX65; Q9IAJ1; P23468; Q64487]:
      FGFR binding motif

<400> SEQUENCE: 93

Thr Leu Thr Gly Leu Lys Pro Asp Thr Thr Tyr Asp Val Lys
1               5                   10

<210> SEQ ID NO 94
<211> LENGTH: 12
<212> TYPE: PRT
<213> ORGANISM: Artificial sequence
<220> FEATURE:
<223> OTHER INFORMATION: Protein tyrosine phosphatase receptor type D
      (PTPRD, BA175E13.1) [Swiss-Prot: Q8WX65; Q9IAJ1; P23468; Q64487]:
      FGFR binding motif

<400> SEQUENCE: 94

Ile Ser Gly Leu Gln Pro Glu Thr Ser Tyr Ser Leu
1               5                   10

```
<210> SEQ ID NO 95
<211> LENGTH: 14
<212> TYPE: PRT
<213> ORGANISM: Artificial sequence
<220> FEATURE:
<223> OTHER INFORMATION: Protein-tyrosine phosphatase receptor-type F
      precursor (EC 3.1.3.48) (LAR protein) (Leukocyte antigen related)
      [Swiss-Prot: Q64604; Q9QW67; P10586]: FGFR binding motif

<400> SEQUENCE: 95

Thr Leu Leu Gly Leu Lys Pro Asp Thr Thr Tyr Asp Ile Lys
1               5                   10

<210> SEQ ID NO 96
<211> LENGTH: 13
<212> TYPE: PRT
<213> ORGANISM: Artificial sequence
<220> FEATURE:
<223> OTHER INFORMATION: Protein-tyrosine phosphatase receptor-type F
      precursor (EC 3.1.3.48) (Leukocyte antigen related) [Swiss-Prot:
      Q64604; Q9QW67; P10586]: FGFR binding motif

<400> SEQUENCE: 96

Thr Ile Ser Gly Leu Thr Pro Glu Thr Thr Tyr Ser Ile
1               5                   10

<210> SEQ ID NO 97
<211> LENGTH: 13
<212> TYPE: PRT
<213> ORGANISM: Artificial sequence
<220> FEATURE:
<223> OTHER INFORMATION: CD22 [Q9R094]: FGFR binding motif

<400> SEQUENCE: 97

Gly Asn Tyr Ser Cys Leu Ala Glu Asn Arg Leu Gly Arg
1               5                   10

<210> SEQ ID NO 98
<211> LENGTH: 12
<212> TYPE: PRT
<213> ORGANISM: Artificial sequence
<220> FEATURE:
<223> OTHER INFORMATION: FGFR-4 [Q91742]: FGFR binding motif

<400> SEQUENCE: 98

Gly Asn Tyr Thr Cys Val Val Glu Asn Arg Val Gly
1               5                   10

<210> SEQ ID NO 99
<211> LENGTH: 12
<212> TYPE: PRT
<213> ORGANISM: Artificial sequence
<220> FEATURE:
<223> OTHER INFORMATION: ICAM-5 [Q8TAM9]: FGFR binding motif

<400> SEQUENCE: 99

Gly Thr Tyr His Cys Val Ala Thr Asn Ala His Gly
1               5                   10

<210> SEQ ID NO 100
<211> LENGTH: 14
<212> TYPE: PRT
<213> ORGANISM: Artificial sequence
<220> FEATURE:
<223> OTHER INFORMATION: FIII,4 domain of L1: FGFR binding motif
      [Swiss-Prot: Q9QY38]

<400> SEQUENCE: 100
```

```
Leu Ser His Asn Gly Val Leu Thr Gly Tyr Leu Leu Ser Tyr
1               5                   10

<210> SEQ ID NO 101
<211> LENGTH: 11
<212> TYPE: PRT
<213> ORGANISM: Artificial sequence
<220> FEATURE:
<223> OTHER INFORMATION: Neuron-glia cell adhesion molecule (Ng-CaM)
      precursor .[Gallus gallus]; [Swiss-Prot: Q90933]: FGFR binding
      motif

<400> SEQUENCE: 101

Asn Gly Val Leu Thr Gly Tyr Val Leu Arg Tyr
1               5                   10

<210> SEQ ID NO 102
<211> LENGTH: 11
<212> TYPE: PRT
<213> ORGANISM: Artificial sequence
<220> FEATURE:
<223> OTHER INFORMATION: Neurofascin precursor. [Gallus gallus];
      [Swiss-Prot: O42414]: FGFR binding motif

<400> SEQUENCE: 102

Asn Gly Val Leu Thr Gly Tyr Asn Leu Arg Tyr
1               5                   10

<210> SEQ ID NO 103
<211> LENGTH: 11
<212> TYPE: PRT
<213> ORGANISM: Artificial sequence
<220> FEATURE:
<223> OTHER INFORMATION: (CALL) Neural cell adhesion molecule. [Homo
      sapiens]. [Swiss-Prot: O00533]: FGFR binding motif

<400> SEQUENCE: 103

Asn Gly Asn Leu Thr Gly Tyr Leu Leu Gln Tyr
1               5                   10

<210> SEQ ID NO 104
<211> LENGTH: 14
<212> TYPE: PRT
<213> ORGANISM: Artificial sequence
<220> FEATURE:
<223> OTHER INFORMATION: f Neuroglian. [Manduca sexta]. [Swiss-Prot:
      P91767]: FGFR binding motif

<400> SEQUENCE: 104

Val Asp Glu Asn Gly Val Leu Thr Gly Tyr Lys Ile Tyr Tyr
1               5                   10

<210> SEQ ID NO 105
<211> LENGTH: 13
<212> TYPE: PRT
<213> ORGANISM: Artificial sequence
<220> FEATURE:
<223> OTHER INFORMATION: Protein-tyrosine phosphotase sigma [Swiss-Prot:
      O75870]; and [Swiss-Prot: Q13332] [Homo sapiens]: FGFR binding
      motif

<400> SEQUENCE: 105

Thr His Asn Gly Ala Leu Val Gly Tyr Ser Val Arg Tyr
1               5                   10

<210> SEQ ID NO 106
<211> LENGTH: 11
<212> TYPE: PRT
```

```
<213> ORGANISM: Artificial sequence
<220> FEATURE:
<223> OTHER INFORMATION: NR-CaM 12 [Rattus sp], [Swiss-Prot: Q9QVN3]:
      FGFR binding motif

<400> SEQUENCE: 106

Asn Gly Ile Leu Thr Glu Tyr Ile Leu Lys Tyr
1               5                   10

<210> SEQ ID NO 107
<211> LENGTH: 11
<212> TYPE: PRT
<213> ORGANISM: Artificial sequence
<220> FEATURE:
<223> OTHER INFORMATION: Neurofascin 155 kDa isoform. [Rattus
      norvegicus], [Swiss-Prot: Q91Z60]: FGFR binding motif

<400> SEQUENCE: 107

Asn Gly Ile Leu Ile Gly Tyr Thr Leu Arg Tyr
1               5                   10

<210> SEQ ID NO 108
<211> LENGTH: 13
<212> TYPE: PRT
<213> ORGANISM: Artificial sequence
<220> FEATURE:
<223> OTHER INFORMATION: Neogenin (Fragment). [Gallus gallus],
      [Swiss-Prot: Q90610]: FGFR binding motif

<400> SEQUENCE: 108

Thr His Ser Gly Gln Ile Thr Gly Tyr Lys Ile Arg Tyr
1               5                   10

<210> SEQ ID NO 109
<211> LENGTH: 11
<212> TYPE: PRT
<213> ORGANISM: Artificial sequence
<220> FEATURE:
<223> OTHER INFORMATION: Neogenin (Fragment). [Gallus gallus],
      [Swiss-Prot: Q90610]: FGFR binding motif

<400> SEQUENCE: 109

Asn Gly Lys Ile Thr Gly Tyr Ile Ile Tyr Tyr
1               5                   10

<210> SEQ ID NO 110
<211> LENGTH: 10
<212> TYPE: PRT
<213> ORGANISM: Artificial sequence
<220> FEATURE:
<223> OTHER INFORMATION: Metalloprotease 1 (pitrilysin family). [Homo
      sapiens] [Swiss-Prot: Q9BSI6]: FGFR binding motif

<400> SEQUENCE: 110

Leu Ser His Asn Gly Ile Phe Thr Leu Tyr
1               5                   10

<210> SEQ ID NO 111
<211> LENGTH: 11
<212> TYPE: PRT
<213> ORGANISM: Artificial sequence
<220> FEATURE:
<223> OTHER INFORMATION: HBRAVO/Nr-CaM. [Homo sapiens]. [Swiss-Prot:
      Q92823; O15179]: FGFR binding motif

<400> SEQUENCE: 111

Asn Gly Ile Leu Thr Glu Tyr Thr Leu Lys Tyr
1               5                   10
```

-continued

```
<210> SEQ ID NO 112
<211> LENGTH: 14
<212> TYPE: PRT
<213> ORGANISM: Artificial sequence
<220> FEATURE:
<223> OTHER INFORMATION: Protein-tyrosine phosphatase kappa precursor
      (EC 3.1.3.48) (R-PTP-kappa). [Homo sapiens]. [Swiss-Prot: Q15262]:
      FGFR binding motif

<400> SEQUENCE: 112

Leu Asp Pro Asn Gly Ile Ile Thr Gln Tyr Glu Ile Ser Tyr
1               5                   10

<210> SEQ ID NO 113
<211> LENGTH: 11
<212> TYPE: PRT
<213> ORGANISM: Artificial sequence
<220> FEATURE:
<223> OTHER INFORMATION: Neogenin precursor (NEO1..). [Homo sapiens and
      Mus musculus] [Swiss-Prot: Q92859; P97798]: FGFR binding motif

<400> SEQUENCE: 113

Asn Gly Lys Ile Thr Gly Tyr Ile Ile Tyr Tyr
1               5                   10

<210> SEQ ID NO 114
<211> LENGTH: 15
<212> TYPE: PRT
<213> ORGANISM: Artificial sequence
<220> FEATURE:
<223> OTHER INFORMATION: Neural cell adhesion L1 (SPLICE ISOFORM 2)
      [Homo sapiens [Swiss-Prot: P32004]; [Mus musculus Swiss-Prot:
      Q9QY38]: FGFR binding motif

<400> SEQUENCE: 114

His Leu Glu Val Gln Ala Phe Asn Gly Arg Gly Ser Gly Pro Ala
1               5                   10                  15

<210> SEQ ID NO 115
<211> LENGTH: 14
<212> TYPE: PRT
<213> ORGANISM: Artificial sequence
<220> FEATURE:
<223> OTHER INFORMATION: NB-2. [Rattus norvegicus] [Swiss-Prot: P97527]:
      FGFR binding motif

<400> SEQUENCE: 115

His Leu Thr Val Arg Ala Tyr Asn Gly Ala Gly Tyr Gly Pro
1               5                   10

<210> SEQ ID NO 116
<211> LENGTH: 15
<212> TYPE: PRT
<213> ORGANISM: Artificial sequence
<220> FEATURE:
<223> OTHER INFORMATION: Neural cell adhesion protein BIG-2 precursor.
      [Rattus norvegicus] [Swiss-Prot: Q62845]: FGFR binding motif

<400> SEQUENCE: 116

His Leu Ser Val Lys Ala Tyr Asn Ser Ala Gly Thr Gly Pro Ser
1               5                   10                  15

<210> SEQ ID NO 117
<211> LENGTH: 15
<212> TYPE: PRT
<213> ORGANISM: Artificial sequence
<220> FEATURE:
<223> OTHER INFORMATION: Axonal-associated cell adhesion molecule. [Homo
      sapiens]. [Swiss-Prot:  Q8TC35]:FGFR binding motif
```

<400> SEQUENCE: 117

His Leu Ala Val Lys Ala Tyr Asn Ser Ala Gly Thr Gly Pro Ser
1               5                   10                  15

<210> SEQ ID NO 118
<211> LENGTH: 14
<212> TYPE: PRT
<213> ORGANISM: Artificial sequence
<220> FEATURE:
<223> OTHER INFORMATION: Contactin A/F3/F11. [Xenopus laevis]
      [Swiss-Prot: O93250]: FGFR binding motif

<400> SEQUENCE: 118

Asn Leu Glu Val Arg Ala Phe Asn Ser Ala Gly Asp Gly Pro
1               5                   10

<210> SEQ ID NO 119
<211> LENGTH: 14
<212> TYPE: PRT
<213> ORGANISM: Artificial sequence
<220> FEATURE:
<223> OTHER INFORMATION: Neural cell adhesion molecule CALL. [Homo
      sapiens] [Swiss-Prot: O00533]: FGFR binding motif

<400> SEQUENCE: 119

His Leu Thr Val Leu Ala Tyr Asn Ser Lys Gly Ala Gly Pro
1               5                   10

<210> SEQ ID NO 120
<211> LENGTH: 13
<212> TYPE: PRT
<213> ORGANISM: Artificial sequence
<220> FEATURE:
<223> OTHER INFORMATION: Neuron-glia cell adhesion molecule (Ng-CaM)
      precursor. [Gallus gallus] [Swiss-Prot: Q909339]: FGFR binding
      motif

<400> SEQUENCE: 120

Leu Arg Val Leu Val Phe Asn Gly Arg Gly Asp Gly Pro
1               5                   10

<210> SEQ ID NO 121
<211> LENGTH: 14
<212> TYPE: PRT
<213> ORGANISM: Artificial sequence
<220> FEATURE:
<223> OTHER INFORMATION: Contactin precursor (Neural cell recognition
      molecule F11). [Gallus gallus] [Swiss-Prot: P14781]: FGFR binding
      motif

<400> SEQUENCE: 121

His Ile Asp Val Ser Ala Phe Asn Ser Ala Gly Tyr Gly Pro
1               5                   10

<210> SEQ ID NO 122
<211> LENGTH: 10
<212> TYPE: PRT
<213> ORGANISM: Artificial sequence
<220> FEATURE:
<223> OTHER INFORMATION: SLIT [Drosophila melanogaster] [Swiss-Prot:
      Q9XYV4]: FGFR binding motif

<400> SEQUENCE: 122

His Leu Ala Val Glu Leu Phe Asn Gly Arg
1               5                   10

<210> SEQ ID NO 123

```
-continued

<211> LENGTH: 14
<212> TYPE: PRT
<213> ORGANISM: Artificial sequence
<220> FEATURE:
<223> OTHER INFORMATION: Galectin-4. [Mus musculus] [Swiss-Prot: Q8K419,
      P38552]: FGFR binding motif

<400> SEQUENCE: 123

Leu Glu Leu Gln Ser Ile Asn Phe Leu Gly Gly Gln Pro Ala
1               5                   10

<210> SEQ ID NO 124
<211> LENGTH: 14
<212> TYPE: PRT
<213> ORGANISM: Artificial sequence
<220> FEATURE:
<223> OTHER INFORMATION: HNB-2. [Homo sapiens] Swiss-Prot: O94779: FGFR
      binding motif

<400> SEQUENCE: 124

His Phe Thr Val Arg Ala Tyr Asn Gly Ala Gly Tyr Gly Pro
1               5                   10

<210> SEQ ID NO 125
<211> LENGTH: 15
<212> TYPE: PRT
<213> ORGANISM: Artificial sequence
<220> FEATURE:
<223> OTHER INFORMATION: The EFL peptide (from the FIII, 3 domain of L1)
      [Swiss-Prot: P32004]: FGFR binding motif

<400> SEQUENCE: 125

His Leu Glu Val Gln Ala Phe Asn Gly Arg Gly Ser Gln Pro Ala
1               5                   10                  15

<210> SEQ ID NO 126
<211> LENGTH: 14
<212> TYPE: PRT
<213> ORGANISM: Artificial sequence
<220> FEATURE:
<223> OTHER INFORMATION: Fragment of Neuroglian (Drosophila)
      [Swiss-prot: P202419]: FGFR binding motif

<400> SEQUENCE: 126

Val Ile Ala Asp Gln Pro Thr Phe Val Lys Tyr Leu Ile Lys
1               5                   10

<210> SEQ ID NO 127
<211> LENGTH: 14
<212> TYPE: PRT
<213> ORGANISM: Artificial sequence
<220> FEATURE:
<223> OTHER INFORMATION: Fragment of Fibronectin (bovine) [Swiss-prot:
      P07589]: FGFR binding motif

<400> SEQUENCE: 127

Thr Ile Lys Gly Leu Arg Pro Gly Val Val Tyr Glu Gly Gln
1               5                   10

<210> SEQ ID NO 128
<211> LENGTH: 14
<212> TYPE: PRT
<213> ORGANISM: Artificial sequence
<220> FEATURE:
<223> OTHER INFORMATION: Tenascin (chick) [Swiss-prot: P10039]: FGFR
      binding motif

<400> SEQUENCE: 128

Thr Leu Thr Glu Leu Ser Pro Ser Thr Gln Tyr Thr Val Lys
```

<210> SEQ ID NO 129
<211> LENGTH: 14
<212> TYPE: PRT
<213> ORGANISM: Artificial sequence
<220> FEATURE:
<223> OTHER INFORMATION: Ephrin type A receptor2 [Swiss-prot: Q8N3Z2]:
      FGFR binding motif

<400> SEQUENCE: 129

Thr Leu Asp Asp Leu Ala Pro Asp Thr Thr Tyr Leu Val Gln
1               5                   10

<210> SEQ ID NO 130
<211> LENGTH: 14
<212> TYPE: PRT
<213> ORGANISM: Artificial sequence
<220> FEATURE:
<223> OTHER INFORMATION: LAR [Swiss-prot Q9VIS8]: FGFR binding motif

<400> SEQUENCE: 130

Thr Val Ser Asp Val Thr Pro His Ala Ile Tyr Thr Val Arg
1               5                   10

<210> SEQ ID NO 131
<211> LENGTH: 14
<212> TYPE: PRT
<213> ORGANISM: Artificial sequence
<220> FEATURE:
<223> OTHER INFORMATION: RTK (Tie-1,hu) [Swiss-prot P35590]: FGFR
      binding motif

<400> SEQUENCE: 131

Ile Ile Arg Gly Leu Asn Ala Ser Thr Arg Tyr Leu Phe Arg
1               5                   10

<210> SEQ ID NO 132
<211> LENGTH: 14
<212> TYPE: PRT
<213> ORGANISM: Artificial sequence
<220> FEATURE:
<223> OTHER INFORMATION: RTK (Tie-1,hu) [Swiss-prot P35590]: FGFR
      binding motif

<400> SEQUENCE: 132

Thr Leu Met Asn Leu Arg Pro Lys Thr Gly Tyr Ser Val Arg
1               5                   10

<210> SEQ ID NO 133
<211> LENGTH: 14
<212> TYPE: PRT
<213> ORGANISM: Artificial sequence
<220> FEATURE:
<223> OTHER INFORMATION: Consensus sequence (conserved domain database):
      FGFR binding motif

<400> SEQUENCE: 133

Thr Leu Thr Gly Leu Lys Pro Gly Thr Glu Tyr Glu Val Arg
1               5                   10

<210> SEQ ID NO 134
<211> LENGTH: 14
<212> TYPE: PRT
<213> ORGANISM: Artificial sequence
<220> FEATURE:
<223> OTHER INFORMATION: The beta-common cytokine receptor of IL-3. Il-5
      and GmCsf [Swiss-prot P32927]: FGFR binding motif

```
<400> SEQUENCE: 134

Gly Pro Glu His Leu Met Pro Ser Ser Thr Tyr Val Ala Arg
1               5                   10

<210> SEQ ID NO 135
<211> LENGTH: 14
<212> TYPE: PRT
<213> ORGANISM: Artificial sequence
<220> FEATURE:
<223> OTHER INFORMATION: Unc-22 (C. Elegance) [Swiss-prot: Q23550]: FGFR
      binding motif

<400> SEQUENCE: 135

Arg Val Thr Gly Leu Thr Pro Lys Lys Thr Tyr Glu Phe Arg
1               5                   10

<210> SEQ ID NO 136
<211> LENGTH: 14
<212> TYPE: PRT
<213> ORGANISM: Artificial sequence
<220> FEATURE:
<223> OTHER INFORMATION: Consensus sequence (conserved domain database):
      FGFR binding motif

<400> SEQUENCE: 136

Thr Leu Thr Gly Leu Lys Pro Gly Thr Glu Tyr Glu Phe Arg
1               5                   10

<210> SEQ ID NO 137
<211> LENGTH: 15
<212> TYPE: PRT
<213> ORGANISM: Artificial sequence
<220> FEATURE:
<223> OTHER INFORMATION: Consensus sequence (conserved domain database):
      FGFR binding motif

<400> SEQUENCE: 137

Glu Val Arg Val Gln Ala Val Asn Gly Gly Asn Gly Pro Pro
1               5                   10              15

<210> SEQ ID NO 138
<211> LENGTH: 12
<212> TYPE: PRT
<213> ORGANISM: Artificial sequence
<220> FEATURE:
<223> OTHER INFORMATION: Drosophila Neuroglian [Swiss-prot: P20241]:
      FGFR binding motif

<400> SEQUENCE: 138

Leu Ile Lys Val Val Ala Ile Asn Asp Arg Gly Glu
1               5                   10

<210> SEQ ID NO 139
<211> LENGTH: 12
<212> TYPE: PRT
<213> ORGANISM: Artificial sequence
<220> FEATURE:
<223> OTHER INFORMATION: Fibronectin (mouse) [Swiss-prot: P11276]: FGFR
      binding motif

<400> SEQUENCE: 139

Val Val Ser Ile Ile Ala Val Asn Gly Arg Glu Glu
1               5                   10

<210> SEQ ID NO 140
<211> LENGTH: 12
<212> TYPE: PRT
<213> ORGANISM: Artificial sequence
```

```
<220> FEATURE:
<223> OTHER INFORMATION: Fibronectin (bovine) [Swiss-prot: P07589]: FGFR
      binding motif

<400> SEQUENCE: 140

Val Val Ser Val Tyr Ala Gln Asn Gln Asn Gly Glu
1               5                   10

<210> SEQ ID NO 141
<211> LENGTH: 12
<212> TYPE: PRT
<213> ORGANISM: Artificial sequence
<220> FEATURE:
<223> OTHER INFORMATION: Tenascine (chick) [Swiss-prot: Q90995]: FGFR
      binding motif

<400> SEQUENCE: 141

Thr Ile Ser Leu Val Ala Glu Lys Gly Arg His Lys
1               5                   10

<210> SEQ ID NO 142
<211> LENGTH: 15
<212> TYPE: PRT
<213> ORGANISM: Artificial sequence
<220> FEATURE:
<223> OTHER INFORMATION: L1 (human, F3,EFL) [Swiss-prot: P32004]: FGFR
      binding motif

<400> SEQUENCE: 142

His Leu Glu Val Gln Ala Phe Asn Gly Arg Gly Ser Gly Pro Ala
1               5                   10                  15

<210> SEQ ID NO 143
<211> LENGTH: 15
<212> TYPE: PRT
<213> ORGANISM: Artificial sequence
<220> FEATURE:
<223> OTHER INFORMATION: L1 (mouse, F3,EFL) [Swiss-prot: P11627]: FGFR
      binding motif

<400> SEQUENCE: 143

His Val Glu Val Gln Ala Phe Asn Gly Arg Gly Leu Gly Pro Ala
1               5                   10                  15

<210> SEQ ID NO 144
<211> LENGTH: 15
<212> TYPE: PRT
<213> ORGANISM: Artificial sequence
<220> FEATURE:
<223> OTHER INFORMATION: L1 (rat, F3,EFL) [Swiss-prot: Q05695]: FGFR
      binding motif

<400> SEQUENCE: 144

His Val Glu Val Gln Ala Phe Asn Gly Arg Gly Leu Gly Pro Ala
1               5                   10                  15

<210> SEQ ID NO 145
<211> LENGTH: 13
<212> TYPE: PRT
<213> ORGANISM: Artificial sequence
<220> FEATURE:
<223> OTHER INFORMATION: Consensus sequence (conserved domain database):
      FGFR binding motif

<400> SEQUENCE: 145

Glu Phe Arg Val Arg Ala Val Asn Gly Ala Gly Glu Gly
1               5                   10
```

```
<210> SEQ ID NO 146
<211> LENGTH: 15
<212> TYPE: PRT
<213> ORGANISM: Artificial sequence
<220> FEATURE:
<223> OTHER INFORMATION: The beta-common cytokine receptor of IL-3. Il-5
      and GmCsf [Swiss-prot: P32927]: FGFR binding motif

<400> SEQUENCE: 146

Val Ala Arg Val Arg Thr Arg Leu Ala Pro Gly Ser Arg Leu Ser
1               5                   10                  15

<210> SEQ ID NO 147
<211> LENGTH: 8
<212> TYPE: PRT
<213> ORGANISM: Artificial sequence
<220> FEATURE:
<223> OTHER INFORMATION: NCAM Fn III, 2 [Swiss-Prot: P13591]: ATP
      binding Walker A motif A

<400> SEQUENCE: 147

Ala Glu Asn Gln Gln Gly Lys Ser
1               5

<210> SEQ ID NO 148
<211> LENGTH: 14
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (Variant)

<400> SEQUENCE: 148

Glu Val Ala Val Ala Glu Asn Gln Gln Gly Ala Ser Ala Ala
1               5                   10

<210> SEQ ID NO 149
<211> LENGTH: 15
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (Variant)

<400> SEQUENCE: 149

Glu Val Tyr Val Val Ala Glu Asn Ala Ala Gly Lys Ser Lys Ala
1               5                   10                  15

<210> SEQ ID NO 150
<211> LENGTH: 9
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (Variant)

<400> SEQUENCE: 150

Val Ala Glu Asn Gln Gln Gly Lys Ser
1               5

<210> SEQ ID NO 151
<211> LENGTH: 7
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (Variant)

<400> SEQUENCE: 151
```

```
Ala Glu Asn Gln Gln Gly Lys
1               5

<210> SEQ ID NO 152
<211> LENGTH: 7
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (Variant)

<400> SEQUENCE: 152

Ala Ala Asn Gln Gln Gly Lys
1               5

<210> SEQ ID NO 153
<211> LENGTH: 7
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (Variant)

<400> SEQUENCE: 153

Ala Glu Ala Gln Gln Gly Lys
1               5

<210> SEQ ID NO 154
<211> LENGTH: 7
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (Variant)

<400> SEQUENCE: 154

Ala Glu Asn Ala Gln Gly Lys
1               5

<210> SEQ ID NO 155
<211> LENGTH: 7
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (Variant)

<400> SEQUENCE: 155

Ala Glu Asn Gln Ala Gly Lys
1               5

<210> SEQ ID NO 156
<211> LENGTH: 7
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (Variant)

<400> SEQUENCE: 156

Ala Glu Asn Gln Gln Ala Lys
1               5

<210> SEQ ID NO 157
<211> LENGTH: 7
<212> TYPE: PRT
<213> ORGANISM: Artificial sequence
<220> FEATURE:
<223> OTHER INFORMATION: NCAM Fn III, 2 [Swiss-Prot: P13591]: FGFR
``` binding motif (Variant)

<400> SEQUENCE: 157

Ala Glu Asn Gln Gln Gly Ala
1               5

<210> SEQ ID NO 158
<211> LENGTH: 7
<212> TYPE: PRT
<213> ORGANISM: Artificial sequence
<220> FEATURE:
<223> OTHER INFORMATION: FGF2

<400> SEQUENCE: 158

Ala Met Lys Glu Asp Gly Arg
1               5

<210> SEQ ID NO 159
<211> LENGTH: 7
<212> TYPE: PRT
<213> ORGANISM: Artificial sequence
<220> FEATURE:
<223> OTHER INFORMATION: FGF2

<400> SEQUENCE: 159

Ala Ala Lys Glu Asp Gly Arg
1               5

<210> SEQ ID NO 160
<211> LENGTH: 7
<212> TYPE: PRT
<213> ORGANISM: Artificial sequence
<220> FEATURE:
<223> OTHER INFORMATION: FGF2

<400> SEQUENCE: 160

Ala Met Ala Glu Asp Gly Arg
1               5

<210> SEQ ID NO 161
<211> LENGTH: 7
<212> TYPE: PRT
<213> ORGANISM: Artificial sequence
<220> FEATURE:
<223> OTHER INFORMATION: FGF2

<400> SEQUENCE: 161

Ala Met Lys Ala Asp Gly Arg
1               5

<210> SEQ ID NO 162
<211> LENGTH: 7
<212> TYPE: PRT
<213> ORGANISM: Artificial sequence
<220> FEATURE:
<223> OTHER INFORMATION: FGF2

<400> SEQUENCE: 162

Ala Met Lys Glu Ala Gly Arg
1               5

<210> SEQ ID NO 163
<211> LENGTH: 7
<212> TYPE: PRT
<213> ORGANISM: Artificial sequence
<220> FEATURE:
<223> OTHER INFORMATION: FGF2

```
<400> SEQUENCE: 163

Ala Met Lys Glu Asp Ala Arg
1               5

<210> SEQ ID NO 164
<211> LENGTH: 7
<212> TYPE: PRT
<213> ORGANISM: Artificial sequence
<220> FEATURE:
<223> OTHER INFORMATION: FGF2

<400> SEQUENCE: 164

Ala Met Lys Glu Asp Gly Ala
1               5

<210> SEQ ID NO 165
<211> LENGTH: 12
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (variant)

<400> SEQUENCE: 165

Val Val Ala Glu Asn Gln Gln Gly Lys Ser Lys Ala
1               5                   10

<210> SEQ ID NO 166
<211> LENGTH: 9
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (variant)

<400> SEQUENCE: 166

Glu Asn Gln Gln Gly Lys Ser Lys Ala
1               5

<210> SEQ ID NO 167
<211> LENGTH: 6
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (variant)

<400> SEQUENCE: 167

Gln Gly Lys Ser Lys Ala
1               5

<210> SEQ ID NO 168
<211> LENGTH: 12
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (variant)

<400> SEQUENCE: 168

Glu Val Tyr Val Val Ala Glu Asn Gln Gln Gly Lys
1               5                   10

<210> SEQ ID NO 169
<211> LENGTH: 9
<212> TYPE: PRT
<213> ORGANISM: Artificial sequence
<220> FEATURE:
```

```
<223> OTHER INFORMATION: NCAM Fn III, 2 [Swiss-Prot: P13591]: FGFR
      binding motif (variant)

<400> SEQUENCE: 169

Glu Val Tyr Val Val Ala Glu Asn Gln
1               5

<210> SEQ ID NO 170
<211> LENGTH: 6
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (variant)

<400> SEQUENCE: 170

Glu Val Tyr Val Val Ala
1               5

<210> SEQ ID NO 171
<211> LENGTH: 11
<212> TYPE: PRT
<213> ORGANISM: Artificial sequence
<220> FEATURE:
<223> OTHER INFORMATION: Axonal-associated cell adhesion molecule [NCBI:
      NP_446331]: FGFR binding motif

<400> SEQUENCE: 171

Val Ala Glu Asn Ser Arg Gly Lys Asn Val Ala
1               5                   10

<210> SEQ ID NO 172
<211> LENGTH: 9
<212> TYPE: PRT
<213> ORGANISM: Artificial sequence
<220> FEATURE:
<223> OTHER INFORMATION: NCAM Fn III, 2 [Swiss-Prot: P13591]: FGFR
      binding motif (Variant)

<400> SEQUENCE: 172

Val Val Ala Glu Asn Gln Gln Gly Lys
1               5

<210> SEQ ID NO 173
<211> LENGTH: 8
<212> TYPE: PRT
<213> ORGANISM: Artificial sequence
<220> FEATURE:
<223> OTHER INFORMATION: NCAM [Swiss-Prot: P13596]

<400> SEQUENCE: 173

Ala Gly His His His His His His
1               5

<210> SEQ ID NO 174
<211> LENGTH: 8
<212> TYPE: PRT
<213> ORGANISM: Artificial sequence
<220> FEATURE:
<223> OTHER INFORMATION: NCAM [Swiss-Prot: P13596]

<400> SEQUENCE: 174

Arg Ser His His His His His His
1               5
```